(12) United States Patent
Wickline et al.

(10) Patent No.: US 9,808,500 B2
(45) Date of Patent: *Nov. 7, 2017

(54) ANTITHROMBOTIC NANOPARTICLE

(71) Applicant: Washington University, St. Louis, MO (US)

(72) Inventors: Samuel A. Wickline, St. Louis, MO (US); Jacob Myerson, St. Louis, MO (US); Rohun Palekar, St. Louis, MO (US); Hua Pan, St. Louis, MO (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/334,108

(22) Filed: Oct. 25, 2016

(65) Prior Publication Data

US 2017/0065669 A1    Mar. 9, 2017

Related U.S. Application Data

(63) Continuation-in-part of application No. 13/516,528, filed as application No. PCT/US2010/061103 on Dec. 17, 2010.

(60) Provisional application No. 62/249,126, filed on Oct. 30, 2015, provisional application No. 61/287,582, filed on Dec. 17, 2009.

(51) Int. Cl.
*A61K 38/10* (2006.01)
*A61K 9/51* (2006.01)
*A61K 45/06* (2006.01)
*A61K 38/06* (2006.01)

(52) U.S. Cl.
CPC ............. *A61K 38/10* (2013.01); *A61K 9/51* (2013.01); *A61K 38/06* (2013.01); *A61K 45/06* (2013.01)

(58) Field of Classification Search
CPC ........ A61K 47/48053; A61K 47/48215; A61K 47/48807
See application file for complete search history.

(56) References Cited

U.S. PATENT DOCUMENTS

| | | |
|---|---|---|
| 3,215,572 A | 11/1965 | Papell |
| 4,297,623 A | 10/1981 | Dupont |
| 5,077,036 A | 12/1991 | Long, Jr. |
| 5,114,703 A | 5/1992 | Wolf et al. |
| 5,171,755 A | 12/1992 | Kaufman et al. |
| 5,260,306 A | 11/1993 | Boardman et al. |
| 5,304,325 A | 4/1994 | Kaufman et al. |
| 5,350,571 A | 9/1994 | Kaufman et al. |
| 5,393,524 A | 2/1995 | Quay |
| 5,403,575 A | 4/1995 | Kaufman et al. |
| 5,534,499 A | 7/1996 | Ansell |
| 5,690,907 A | 11/1997 | Lanza et al. |
| 5,780,010 A | 7/1998 | Lanza et al. |
| 5,820,848 A | 10/1998 | Boni et al. |
| 5,958,371 A | 9/1999 | Lanza et al. |
| 5,989,520 A | 11/1999 | Lanza et al. |
| 6,368,586 B1 | 4/2002 | Jacob et al. |
| 6,413,544 B1 | 7/2002 | Smyth-Templeton et al. |
| 6,491,903 B1 | 12/2002 | Forster et al. |
| 6,579,846 B1 | 6/2003 | Zirnstein et al. |
| 7,022,313 B2 | 4/2006 | O'Connor et al. |
| 9,446,150 B2 | 9/2016 | Lanza et al. |
| 9,468,607 B2 | 10/2016 | Pan et al. |
| 9,498,439 B2 | 11/2016 | Lanza et al. |
| 2002/0034536 A1 | 3/2002 | Perkins et al. |
| 2003/0157179 A1 | 8/2003 | Blum et al. |
| 2003/0185879 A1 | 10/2003 | Boulikas |
| 2004/0142474 A1 | 7/2004 | Mahato et al. |
| 2004/0229945 A1 | 11/2004 | Satchi-Fainaro et al. |
| 2005/0037050 A1 | 2/2005 | Weber |
| 2005/0079131 A1 | 4/2005 | Lanza et al. |
| 2005/0095267 A1* | 5/2005 | Campbell ............... A61F 2/82 424/425 |
| 2006/0008461 A1 | 1/2006 | Yatvin et al. |
| 2006/0015261 A1 | 1/2006 | Mann et al. |
| 2006/0159619 A1 | 7/2006 | Becker et al. |
| 2006/0228299 A1 | 10/2006 | Thorpe et al. |
| 2006/0264397 A1 | 11/2006 | Kucera et al. |
| 2007/0020308 A1 | 1/2007 | Richard et al. |
| 2007/0110777 A1 | 5/2007 | Joabsson et al. |
| 2007/0154539 A1 | 7/2007 | Fountain |
| 2008/0269875 A1 | 10/2008 | Zhao |
| 2008/0286321 A1 | 11/2008 | Reneker et al. |
| 2008/0286372 A1 | 11/2008 | Pacetti et al. |
| 2009/0148383 A1 | 6/2009 | Peter |
| 2009/0163437 A1 | 6/2009 | Rusconi |

(Continued)

FOREIGN PATENT DOCUMENTS

| WO | 9620698 A2 | 7/1996 |
|---|---|---|
| WO | 0174337 A1 | 10/2001 |

(Continued)

OTHER PUBLICATIONS

Bartha, K., et al., "Thrombin Regulates Tissue Factor and Thrombomodulin mRNA Levels and Activities in Human Saphenous Vein Endothelial Cells by Distinct Mechanisms," J. Biol. Chem., Jan. 5, 1993, pp. 421-429, vol. 268, No. 1, The American Society for Biochemistry and Molecular Biology, Inc., USA.

Blankenberg, S. et al., "Adhesion molecules and atherosclerosis," Atherosclerosis, Oct. 2003, pp. 191-203, vol. 170, No. 2, Elsevier.

Bombeli, T. et al., "Apoptotic Vascular Endothelial Cells Become Procoagulant," Blood, Apr. 1, 1997, pp. 2429-2442, vol. 89, No. 7, American Society of Hematology.

Borissoff, J. et al., "Early Atherosclerosis Exhibits an Enhanced Procoagulant State," Circulation, Aug. 24, 2010, pp. 821-830, vol. 122, No. 8, with Supplemental Material, pp. 1-13, American Heart Association, Inc.

Borissoff, J. et al., "Is thrombin a key player in the "coagulation-atherogenesis" maze?," Cardiovascular Res., 2009, pp. 392-403, vol. 82, No. 3.

(Continued)

*Primary Examiner* — Robert Cabral
(74) *Attorney, Agent, or Firm* — Plsinelli PC

(57) ABSTRACT

The present invention encompasses an antithrombotic nanoparticle and use thereof.

12 Claims, 57 Drawing Sheets
(48 of 57 Drawing Sheet(s) Filed in Color)

(56) References Cited

U.S. PATENT DOCUMENTS

| | | |
|---|---|---|
| 2009/0202429 A1 | 8/2009 | Diacovo et al. |
| 2009/0208548 A1 | 8/2009 | Mason et al. |
| 2010/0028994 A1 | 2/2010 | DeSimone et al. |
| 2010/0297007 A1 | 11/2010 | Lanza et al. |
| 2010/0297019 A1 | 11/2010 | Lanza et al. |
| 2013/0064765 A1 | 3/2013 | Myerson et al. |
| 2013/0122100 A1 | 5/2013 | Lanza et al. |
| 2016/0279060 A1 | 9/2016 | Lanza et al. |

FOREIGN PATENT DOCUMENTS

| | | |
|---|---|---|
| WO | 03015831 A1 | 2/2003 |
| WO | WO03015931 A1 * | 2/2003 |
| WO | 2004017907 A2 | 3/2004 |
| WO | 2005014051 A1 | 2/2005 |
| WO | 2006072943 A2 | 7/2006 |
| WO | 2006117720 A2 | 11/2006 |
| WO | 2007034359 A2 | 3/2007 |
| WO | 2007106683 A2 | 9/2007 |
| WO | 2008063157 A2 | 5/2008 |
| WO | 2008109712 A2 | 9/2008 |
| WO | 2009049083 A1 | 4/2009 |
| WO | 2009049089 A1 | 4/2009 |
| WO | 2009151788 A2 | 12/2009 |
| WO | 2011084700 A1 | 7/2011 |
| WO | 2011130674 A1 | 10/2011 |

OTHER PUBLICATIONS

Borissoff, J. et al., "Mechanisms of Disease: The Hemostatic System as a Modulator of Atherosclerosis," N. Engl. J. Med., May 5, 2011, pp. 1746-1760, vol. 364, No. 18, Massachusetts Medical Society.

Bowen-Pope, D. et al., "History of discovery: platelet-derived growth factor," Arterioscler. Thromb. Vasc. Biol., Nov. 2011, pp. 2397-2401, vol. 31, No. 11, American Heart Association, Inc.

Chen, J. et al., "Antithrombin nanoparticles improve kidney reperfusion and protect kidney function after ischemia-reperfusion injury," Am. J. Physiol. Renal Physiol., Jan. 28, 2015, pp. F765-F773, vol. 308, No. 7, The American Physiological Society.

Costopoulus, C. et al., "Novel oral anticoagulants in acute coronary syndrome," Int. J. Cardiol., Sep. 10, 2013, pp. 2449-2455, vol. 167, No. 6, Elsevier Ireland Ltd.

Coughlin, S., "How the protease thrombin talks to cells," PNAS, Sep. 1999, pp. 11023-11027, vol. 96, No. 20.

Davie, E et al., "An Overview of the Structure and Function of Thrombin," Semin. Thromb. Hemost., 2006, pp. 3-15, vol. 32, Supplement 1, Thieme Medical Publishers, Inc., New York.

Eitzman, D. et al., "Hyperlipidemia Promotes Thrombosis After Injury to Atherosclerotic Vessels in Apolipoprotein E-Deficient Mice," Arterioscler. Thromb. Vasc. Biol., Jul. 2000, pp. 1831-1834, vol. 20, No. 7, American Heart Association, Dallas.

Esmon, C., " Crosstalk between inflammation and thrombosis," Maturitas, Apr. 15, 2004, pp. 305-314, vol. 47, No. 4, Elsevier Ireland, Ltd.

Farb, A. et al., "Coronary Plaque Erosion Without Rupture Into a Lipid Core: A Frequent Cause of Coronary Thrombosis in Sudden Coronary Death," Circulation, Apr. 1, 1996, pp. 1354-1363, vol. 93, No. 7.

Gareus, R. et al., "Endothelial Cell-Specific NF-κB Inhibition Protects Mice from Atherosclerosis," Cell Metabolism, Nov. 5, 2008, pp. 372-383, vol. 8, No. 5, Elsevier Inc.

Hajra, L. et al., "The NF-kappaB signal transduction pathway in aortic endothelial cells is primed for activation in regions predisposed to atherosclerotic lesion formation," PNAS, Aug. 1, 2000, pp. 9052-9057, vol. 97, No. 16.

Hansson, G. et al., "Aortic Endothelial Cell Death and Replication in Normal and Lipopolysaccharide-Treated Rats," Am. J. Pathol., Oct. 1985, pp. 123-127, vol. 121, No. 1.

Hara, T. et al., "Rivaroxaban, a novel oral anticoagulant, attenuates atherosclerotic plaque progression and destabilization in ApoE-deficient mice," Atherosclerosis, Oct. 2015, pp. 639-646, vol. 242, No. 2, Elsevier Ireland Ltd.

Jagadeesha, D. et al., "Nox1 transactivation of epidermal growth factor receptor promotes N-cadherin shedding and smooth muscle cell migration," Cardiovascular Res., 2012, pp. 406-413, vol. 93, No. 3, European Society of Cardiology.

Kadoglou, N. et al., "The Beneficial Effects of a Direct Thrombin Inhibitor, Dabigatran Etexilate, on the Development and Stability of Atherosclerotic Lesions in Apolipoprotein E-deficient Mice," Cardiovasc. Drugs Ther., Oct. 2012, pp. 367-374, vol. 26, No. 5, Springer Science+Business Media, LLC.

Kalz, J. et al., "Thrombin generation and atherosclerosis," J. Thromb. Thrombolysis, Jan. 2014, pp. 45-55, vol. 37, No. 1, Springer Science+Business Media, New York.

Kanters, E. et al., "Inhibition of NF-kappaB activation in macrophages increases atherosclerosis in LDL receptor-deficient mice," J. Clin. Invest., Oct. 2003, pp. 1176-1185, vol. 112, No. 8.

Lampka, M. et al., "Circulating endothelial cells in coronary artery disease," Kardiol. Pol., 2010, pp. 1100-1105, vol. 68, No. 10, Via Medica.

Lee, I-O et al., "The Effects of Direct Thrombin Inhibition with Dabigatran on Plaque Formation and Endothelial Function Apolipoprotein E-Deficient Mice," JPET, 2012, pp. 253-257, vol. 343, No. 2.

Ley, K. et al., "VCAM-1 is critical in atherosclerosis," J. Clin. Invest., May 2001, pp. 1209-1210, vol. 107, No. 10.

Libby, P., "Inflammation in Atherosclerosis," Arterioscler. Thromb. Vas. Biol., Sep. 2012, pp. 2045-2051, vol. 32, No. 3, American Heart Association, Inc.

Maganto-Garcia, E. et al., "Mouse Models of Atherosclerosis," Curr. Protoc. Immunol., 2012, pp. 15.24.1-15.24.23, vol. 96, Chapter 15, Unit 24, John Wiley & Sons, Inc.

Malaver, E. et al., "NF-kappaB inhibitors impair platelet activation responses," J. Thromb. Haemost., 2009, pp. 1333-1343, vol. 7, No. 8, International Society on Thrombosis and Haemostasis.

Meyrelles, S. et al., "Endothelial Dysfunction in the Apolipoprotein E-deficient Mouse: insights into the influence of diet, gender and aging," Lipids Health Dis., 2011, p. 1-18, vol. 10, No. 211.

Nylaende, M. et al., "Prothrombotic activity is associated with the anatomical as well as the functional severity of peripheral arterial occlusive disease," Thromb. Haemost., 2006, pp. 702-707, vol. 95, No. 4, Schattauer GmbH, Stuttgart.

Olson, E. et al., "In vivo fluorescence imaging of atherosclerotic plaques with activatable cell-penetrating peptides targeting thrombin activity," Integr. Biol., Jun. 2012, pp. 595-605, vol. 4, No. 6, Royal Society of Chemistry.

Palekar, R. et al., "Inhibition of Thrombin With PPACK-Nanoparticles Restores Disrupted Endothelial Barriers and Attenuates Thrombotic Risk in Experimental Atheroschlerosis," Arterioscler. Thromb. Vasc. Biol., Mar. 2016, pp. 146-455, vol. 36, No. 3, with Supplemental Material, 9 pgs.

Palekar, R. et al., "Quantifying progression and regression of thrombotic risk in experimental atherosclerosis," FASEB J., Apr. 9, 2015, pp. 3100-3109, vol. 29, No. 7.

Pingel, S. et al., "Thrombin inhibition by dabigatran attenuates atherosclerosis in ApoE deficient mice," Arch. Med. Sci., Feb. 2014, pp. 154-160, vol. 10, No. 1, Termedia & Banach.

Rahman, A. et al., "Blocking NF-KB: An Inflammatory Issue," Proc. Am. Thorac. Soc., 2011, pp. 497-503, vol. 8, No. 6.

Steffel, J. et al., "Tissue factor in cardiovascular diseases: molecular mechanisms and clinical implications," Circulation, Feb. 7, 2006, pp. 722-731, vol. 113, No. 5.

Takeya, H. et al., "Synergistic effect of sphingosine 1-phosphate on thrombin-induced tissue factor expression in endothelial cells," Blood, Sep. 1, 2003, pp. 1693-1700, vol. 102, No. 5, The American Society of Hematology.

Tull, S. et al., "PR3 and Elastase Alter PAR1 Signaling and Trigger vWF Release via a Calcium-Independent Mechanism from Glomerular Endothelial Cells," PLoS ONE, Aug. 2012, pp. 1-10, vol. 7, No. 8, e43916.

(56) References Cited

OTHER PUBLICATIONS

Zhang, H. et al., "Quantifying the Evolution of Vascular Barrier Disruption in Advanced Atherosclerosis with Semipermeant Nanoparticle Contrast Agents," PLoS ONE, Oct. 2011, pp. 1-11, vol. 6, No. 10, e26385.
Flaim, "Pharmacokinetics and Side Effects of Perfluorocarbon-Based Blood Substitutes," Artificial Cells, Blood Substitutes, and Immobilization Biotechnology, 1994, pp. 1043-1054, vol. 22, No. 4.
Forrest et al., "Partial Acetylation of Polyethylenimine Enhances In Vitro Gene Delivery," Pharmaceutical Research, 2004, pp. 365-371, vol. 21, No. 2.
Furie et al., "Mehanisms of Thrombus Formation," The New England Journal of Medicine, 2008, pp. 938-949, vol. 359, No. 9.
Garg et al., "Nuclear transcription factor-κB as a target for cancer drug development," Leukemia, 2002, pp. 1053-1068, vol. 16.
Ghigliotti et al., "Prolonged Activation of Prothrombin on the Vascular Wall After Arterial Injury," Arteriosclerosis, Thrombosis, and Vascular Biology, 1998, pp. 250-257, vol. 18.
Gilchrist et al., "Selective Inductive Heating of Lymph Nodes," Annals of Surgery, 1957, pp. 596-606, vol. 146, No. 4.
Glagov et al., "Compensatory Enlargement of Human Atherosclerotic Coronary Arteries," The New England Journal of Medicine, 1987, pp. 1371-1375, vol. 316, No. 22.
Gross et al., "New Antithrombotic Drugs," Clinical Pharmacology & Therapeutics, 2009, pp. 139-146, vol. 86, No. 2.
Grossman et al., "Cytokine Expression and Tumorigenicity of Large Granular Lymphocytic Leukemia Cells From Mice Transgenic for the tax Gene of Human T-Cell Leukemia Virus Type I," Blood, 1997, pp. 783-794, vol. 90, No. 2.
Grossman et al., "Development of leukemia in mice transgenic for the tax gene of human T-cell leukemia virus type I," Proc. Natl. Acad. Sci. USA, 1995, pp. 1057-1061, vol. 92.
Hess et al., "Biological and Chemical Applications of Fluorescence Correlation Spectroscopy: A Review," Biochemistry, 2002, pp. 697-705, vol. 41, No. 3.
Hirano, "The Roles of Proteinase-Activated Receptors in the Vascular Physiology and Pathophysiology," Arteriosclerosis, Thrombosis, and Vascular Biology, 2007, pp. 27-36, vol. 27.
Hirsh et al., "Beyond Unfractionated Heparin and Warfarin: Current and Future Advances," Circulation, 2007, pp. 552-560, vol. 116.
Hofman et al., "Quantification of In-Plane Motion of the Coronary Arteries During the Cardiac Cycle: Implications for Acquisition Window Duration for MR Flow Quantification," Journal of Magnetic Resonance Imaging, 1998, pp. 568-576, vol. 8, No. 3.
Hu et al., "Imaging of Vx-2 rabbit tumors with $\alpha v \beta 3$-integrin-targeted 111In nanoparticles," International Journal of Cancer, 2007, pp. 1951-1957, vol. 120.
International Search Report and Written Opinion dated Dec. 15, 2008 from related International Application No. PCT/US2008/79414; 15 pgs.
International Search Report and Written Opinion dated Dec. 24, 2008 from related International Application No. PCT/US2008/79404; 8 pgs.
International Search Report and Written Opinion dated Apr. 6, 2011 from related International Application No. PCT/US2010/61103; 12 pgs.
International Search Report and Written Opinion dated Jul. 8, 2011 from related International Application No. PCT/US2011/32744; 10 pgs.
Ivey et al., "Thrombin regulates vascular smooth muscle cell proteoglycan synthesis via PAR-1 and multiple downstream signalling pathways," Thrombosis Research, 2008, pp. 288-297, vol. 123.
Kaiser et al., "Pharmacology of Synthetic Thrombin Inhibitors of the Tripeptide Type," Cardiovascular Drug Reviews, 1992, pp. 71-87, vol. 10, No. 1.
Kaneda et al., "Perfluorocarbon Nanoemulsions for Quantitative Molecular Imaging and Targeted Therapeutics," Ann Biomed Eng., 2009, pp. 1922-1933, vol. 37, No. 10.
Karin, "The Beginning of the End: IκB Kinase (IKK) and NF-κB Activation*," The Journal of Biological Chemistry, 1999, pp. 27339-27342, vol. 274, No. 39.
Karin et al., "NF-κB in Cancer: From Innocent Bystander to Major Culprit," Nature Reviews/Cancer, 2002, pp. 301-310, vol. 2.
Karin, "Nuclear factor-κB in cancer development and progression," Nature, 2006, pp. 431-436, vol. 441.
Kettner et al., "D-Phe-Pro-ArgCH2C1-A Selective Affinity Label for Thrombin," Thrombosis Research, 1979, pp. 369-973, vol. 14, No. 6.
Kim et al., "Development of a novel dosage form for intramuscular injection of titrated extract of Centella asiatica in a mixed micellar system," International Journal of Pharmaceutics, 2001, pp. 141-147, vol. 220.
Klocek et al., "Thermodynamics of Melittin Binding to Lipid Bilayers. Aggregation and Pore Formation," Biochemistry, 2009, pp. 2586-2596, vol. 48, No. 12.
Kukreja et al., "The future of drug-eluting stents," Pharmacological Research, 2008, pp. 171-180, vol. 57.
Landfester et al., "Encapsulated magnetite particles for biomedical application," Journal of Physics: Condensed Matter, 2003, pp. S1345-S1361, vol. 15.
Lanza et al., "Targeted Antiproliferative Drug Delivery to Vascular Smooth Muscle Cells With a Magnetic Resonance Imaging Nanoparticle Contrast Agent: Implications for Rational Therapy of Restenosis," Circulation, 2002, pp. 2842-2847, vol. 106.
Lanza et al., "Molecular Imaging of Stretch-Induced Tissue Factor Expression in Carotid Arteries with Intravascular Ultrasound," Investigative Radiology, 2000, pp. 227-234, vol. 35, No. 4.
Lanza et al., "Nanomedicine opportunities for cardiovascular disease with perfluorocarbon nanoparticles," Nanomedicine, 2006, pp. 321-329, vol. 1, No. 3.
Lee, "Anticoagulants in Coronary Artery Disease," Clinical Cardiology, 2008, pp. 615-628, vol. 26.
Liu et al., "Preparation and characterization of biodegradable magnetic carriers by single emulsion-solvent evaporation," Journal of Magnetism and Magnetic Materials, 2007, pp. 84-87, vol. 311.
Liu et al., "Surface Modification and Characterization of Magnetic Polymer Nanospheres Prepared by Miniemulsion Polymerization," Langmuir, 2004, pp. 10278-10282, vol. 20, No. 23.
Lopez-Guerra et al., "NF-κB as a therapeutic target in chronic lymphocytic leukemia," Expert Opin. Ther. Targets, 2010, pp. 275-288, vol. 14, No. 3.
Maclean et al., "Hereditary and Acquired Antithrombin Deficiency: Epidemiology, Pathogenesis and Treatment Options," Drugs, 2007, pp. 1429-1440, vol. 67, No. 10.
Mandal et al., "Encapsulation of Magnetic and Fluorescent Nanoparticles in Emulsion Droplets," Langmuir, 2005, pp. 4175-4179, vol. 21, No. 9.
Marsh et al., "Molecular imaging with targeted perfluorocarbon nanoparticles: Quantification of the concentration dependence of contrast enhancement for binding to sparse cellular epitopes," Ultrasound Med Biol., 2007, pp. 350-958, vol. 33, No. 6.
May et al., "Selective Inhibition of Nf-κB Activation by a Peptide That Blocks the Interaction of NEMO with the IκB Kinase Complex," Science, 2000, pp. 1550-1554, vol. 289.
May et al., "Individualized antithrombotic therapy in high risk patients after coronary stenting. A double-edged sword between thrombosis and bleeding," Journal of Thrombosis and Haemostasis, 2008, pp. 487-493, vol. 99.
Montagne et al., "Preparation and characterization of narrow sized (o/w) magnetic emulsion," Journal of Magnetism and Magnetic Materials, 2002, pp. 302-312, vol. 250.
Moody et al., "Direct magnetic resonance imaging of carotid artery thrombus in acute stroke," The Lancet, 1999, pp. 122-123, vol. 353.
Morales et al., "Contrast agents for MRI based on iron oxide nanoparticles prepared by laser pyrolysis," Journal of Magnetism and Magnetic Materials, 2003, pp. 102-109, vol. 266.
Morawski et al., "Quantitative "Magnetic Resonance Immunohistochemistry" with Ligand-Targeted 19F Nanoparticles," Magnetic Resonance in Medicine, 2004, pp. 1255-1262, vol. 52.

(56) References Cited

OTHER PUBLICATIONS

Mulder et al., "Lipid-based nanoparticles for contrast-enhanced MRI and molecular imaging," NMR in Biomedicine, 2006, pp. 142-164, vol. 19.
Mulder et al., "MR molecular imaging and fluorescence microscopy for identification of activated tumor endothelium using a bimodal lipidic nanoparticle," The FASEB Journal, 2005, pp. 2008-2010, vol. 19.
Myerson et al., "'Thrombin sponge': A potent nanoparticle approach to inhibiting coagulation in acute thrombosis," The FASEB Journal, 2010, p. 574.2, vol. 24, No. 1.
Myerson et al., "Thrombin-inhibiting perfluorocarbon nanoparticles provide a novel strategy for treatment and magnetic resonance imaging of acute thrombosis," Journal of Thrombosis and Haemostasis, 2011, pp. 1292-1300, vol. 9, No. 7.
Su, "Assembly of polydiacetylene vesicles on solid substrates," J. Colloid and Interface Science, 2005, pp. 271-276, vol. 292.
Sun et al., "Persistent activation of NF-κB by the Tax transforming protein of HTLV-1: hijacking cellular IκB kinases," Oncogene, 1999, pp. 6948-6958, vol. 18.
Thorek et al., "Superparamagnetic Iron Oxide Nanoparticle Probes for Molecular Imaging," Annals of Biomedical Engineering, 2006, pp. 23-38, vol. 34, No. 1.
Torreri et al., "Biomolecular interactions by Surface Plasmon Resonance technology," Ann 1st Super Sanita, 2005, pp. 437-441, vol. 41, No. 4.
Tran et al., "Association of Hereditary Heparin Co-Factor II Deficiency With Thrombosis," The LANCET, 1985, pp. 413-414, vol. 2.
Turpie, "The top 4 advances in antithrombotic care in the last year," Thrombosis Research, 2008, pp. S2-S6, vol. 123.
Verweij et al., "Paclitaxel (Taxol) and docetaxel (Taxotere): Not simply two of a kind," Annals of Oncology, 1994, pp. 495-505, vol. 5.
Vicente et al., "Antithrombotic activity of dermatan sulfate in heparin cofactor II-deficient mice," Blood, 2004, pp. 3965-3970, vol. 104, No. 13.
Vyavahare et al., "In vitro and in vivo evaluation of the site-specific administration of D-phenylalanyl-L-prolyl-L-arginyl chloromethyl ketone (PPACK): a powerful thrombin inhibitor," Journal of Controlled Release, 1993, pp. 165-173, vol. 27, No. 2.
Wallentin et al., "Ticagrelor versus Clopidogrel in Patients with Acute Coronary Syndromes," The New England Journal of Medicine, 2009, pp. 1045-1057, vol. 361, No. 11.
Weissmann et al., "Effect of melittin upon cellular and lysosomal membranes," Biochemical Pharmacology, 1969, pp. 1771-1775, vol. 18.
Weitz et al., "Clot-bound Thrombin Is Protected from Inhibition by Heparin-Antithrombin III but Is Susceptible to Inactivation by Antithrombin III-independent Inhibitors," Journal of Clinical Investigation, 1990, pp. 385-391, vol. 86.
Westrick et al., "Murine Models of Vascular Thrombosis," Arteriosclerosis, Thrombosis, and Vascular Biology, 2007, pp. 2079-2093, vol. 27.
Winter et al., "Emerging nanomedicine opportunities with perfluorocarbon nanoparticles," Expert Rev. Med. Devices, 2007, pp. 137-145, vol. 4, No. 2.
Winter et al., "Antiangiogenic Synergism of Integrin-Targeted Fumagillin Nanoparticles and Atorvastatin in Atherosclerosis," JACC: Cardiovascular Imaging, 2008, pp. 624-634, Vol. 1, No. 5.
Winter et al., "Molecular Imaging of Angiogenesis in Early-Stage Atherosclerosis With αvβ3-Integrin-Targeted Nanoparticles," Circulation, 2003, pp. 2270-2274, vol. 108.
Winter et al., "Molecular Imaging of Angiogenesis in Nascent Vx-2 Rabbit Tumors Using a Novel αvβ3-targeted Nanoparticle and 1.5 Tesla Magnetic Resonance Imaging," Cancer Research, 2003, pp. 5838-5843, vol. 63.
Winter et al., "Molecular Imaging by MRI," Current Cardiology Reports, 2006, pp. 65-69, vol. 8.
Winter et al., "Endothelial alphaVbeta3 Integrin-Targeted Fumagillin Nanoparticles Inhibit Angiogenesis in Atherosclerosis," Arterioscler. Thromb. Vasc. Biol., Sep. 2006, pp. 2103-2109, vol. 26.
Xu et al., "Encapsulation of nanosized magnetic iron oxide by polyacrylamide via inverse miniemulsion polymerization," Journal of Magnetism and Magnetic Materials, 2004, pp. 136-143, vol. 277.
Yamaoka et al., "Complementation Cloning of NEMO, a Component of the IκB Kinase Complex Essential for NF-κB Activation," Cell, 1998, pp. 1231-1240, vol. 93.
Yang et al., "Preparation of poly e-caprolactone nanoparticles containing magnetite for magnetic drug carrier," International Journal of Pharmaceutics, 2006, pp. 185-190, vol. 324, No. 2.
Zhou et al. "Suppression of inflammation in a mouse model of rheumatoid arthritis using targeted lipase-labile fumagillin prodrug nanoparticles," Biomaterials, Nov. 1, 2012, pp. 8632-8640, vol. 33, No. 33.
Notice of Allowance dated Feb. 27, 2017 from related U.S. Appl. No. 13/516,528; 9 pgs.
Acharyya et al., "Interplay of IKK/NF-κB signaling in macrophages and myofibers promotes muscle degeneration in Duchenne muscular dystrophy," The Journal of Clinical Investigation, 2007, pp. 889-901, vol. 117, No. 4.
Ambrose et al., "Angiographic Progression of Coronary Artery Disease and the Development of Myocardial Infarction," JACC, 1988, pp. 56-62, vol. 12, No. 1.
Andersson et al., "Heparin cofactor II activity in plasma: Application of an automated assay method to the study of a normal adult population," Scand. J. Haematol., 1986, pp. 96-102, vol. 36.
Angelova et al., "Liposome Electroformation," Faraday Discuss. Chem. Soc., 1986, pp. 303-311, vol. 81.
Ansell et al., "The Pharmacology and Management of the Vitamin K Antagonists," CHEST, 2004, pp. 204S-233S, vol. 126, No. 3.
Bacia et al., "Fluorescence Correlation Spectroscopy," Methods in Molecular Biology, 2007, pp. 73-84, vol. 398.
Baud et al., "Is NF-κB a good target for cancer therapy? Hopes and pitfalls," Nat. Rev. Drug Discov., 2009, pp. 33-40, vol. 8, No. 1.
Benson, "The Present Status of Coronary Arterial Disease," Archives of Pathology & Laboratory Medicine, 1926, pp. 376-916, vol. 2.
Bernal-Mizrachi et al., "The role of NF-κB-1 and NF-κB-2-mediated resistance to apoptosis in lymphomas," PNAS, 2006, pp. 9220-9225, vol. 103, No. 24.
Bertina et al., "Hereditary Heparin Cofactor II Deficiency and the Risk of Development of Thrombosis," J. Thromb. and Haemostasis, 1987, pp. 196-200, vol. 57, No. 2.
Bhoj et al., "Ubiquitylation in innate and adaptive immunity," Nature, 2009, pp. 430-437, vol. 458.
Bibette, "Monodisperse ferrofluid emulsions," Journal of Magnetism and Magnetic Materials, 1993, pp. 37-41, vol. 122.
Bidwell III et al., "Therapeutic peptides for cancer therapy. Part I—peptide inhibitors of signal transduction cascades," Expert Opin. Drug Deliv., 2009, pp. 1033-1047, vol. 6, No. 10.
Bode et al., "The refined 1.9 Å crystal structure of human α-thrombin: interaction with D-Phe-Pro-Arg chloromethylketone and significance of the Tyr-Pro-Pro-Trp insertion segment," The EMBO Journal, 1989, pp. 3467-3475, vol. 8, No. 11.
Bode et al., "The refined 1.9-Å X-ray crystal structure of D-Phe-Pro-Arg chloromethylketone-inhibited human athrombin: Structure analysis, overall structure, electrostatic properties, detailed active-site geometry, and structure-function relationships," Prot. Sci., 1992, pp. 426-471, vol. 1.
Bousser, "Antithrombotic Agents in the Prevention of Ischemic Stroke," Cerebrovascular Diseases, 2009, pp. 12-19, vol. 27 (Suppl. 3).
Bowen, "Particle Size Distribution Measurement from Millimeters to Nanometers and from Rods to Platelets," J. of Dispersion Science and Technology, 2002, pp. 631-662, vol. 23, No. 5.
Boxus et al., "The HTLV-I Tax interactome," Retrovirology, 2008, pp. 76-99, vol. 5.

(56) References Cited

OTHER PUBLICATIONS

Bretschneider et al., "Evidence for functionally active protease-activated receptor-4 (PAR-4) in human vascular smooth muscle cells," British Journal of Pharmacology, 2001, pp. 1441-1446, vol. 132, No. 7.
Bretschneider et al., "Evidence for functionally active protease-activated receptor-3 (PAR-3) in human vascular smooth muscle cells," J. Thrombosis and Haemostasis, 2003, pp. 704-709, vol. 90.
Brown et al., "Incomplete lysis of thrombus in the moderate underlying atherosclerotic lesion during intracoronary infusion of streptokinase for acute myocardial infarction: quantitative angiographic observations," Circulation, 1986, pp. 553-661, vol. 73, No. 4.
Brownlie et al., "PEI-based vesicle-polymer hybrid gene delivery system with improved biocompatibility," Int. J. Pharmaceutics, 2004, pp. 41-52, vol. 274.
Caruthers et al., "Anti-angiogenic perfluorocarbon nanoparticles for diagnosis and treatment of atherosclerosis," WIREs Nanomedicine and Nanobiotechnology, 2009, pp. 311-323, vol. 1.
CAS Registry Record for Fumagillin (CAS # 23110-15-8). Entered STN Nov. 16, 1984, Accessed by Examiner on Mar. 8, 2016, 2 pgs.
CAS Registry Record for Fumagillol (CAS # 108102-51-8). Entered STN May 16, 1987, Accessed by Examiner on Mar. 8, 2016, 2 pgs.
Casscells et al., "Thermal detection of cellular infiltrates in living atherosclerotic plaques: possible implications for plaque rupture and thrombosis," The Lancet, 1996, pp. 1447-1449, vol. 347.
Cerqueira, "Current Status of Radionuclide Tracer Imaging of Thrombi and Atheroma," Seminars in Nuclear Medicine, 1999, pp. 339-351, vol. 29, No. 4.
Charles, "Some Applications of Magnetic Fluids—Use As an Ink and in Microwave Systems," Journal of Magnetism and Magnetic Materials, 1987, pp. 350-358, vol. 65.
Cho et al., "Ability of Surfactant Micelles to Alter the Physical Location and Reactivity of Iron in Oil-in-Water Emulsion," Journal of Agricultural and Food Chemistry, 2002, pp. 5704-5710, vol. 50, No. 20.
Collen et al., "In vivo studies of a synthetic inhibitor of thrombin," J. Lab. Clin. Med., 1982, pp. 76-83, vol. 99, No. 1.
Connors, J., "Antidote for Factor Xa Anticoagulants," The New England Journal of Medicine, Dec. 17, 2015, pp. 2471-2472, vol. 373, No. 25.
Constantinides, "Plaque Fissures in Human Coronary Thrombosis," Journal of Atherosclerosis Research, 1966, pp. 1-17, vol. 6.
Coughlin, "Thrombin signalling and protease-activated receptors," Nature, 2000, pp. 258-264, vol. 407.
Davies, "Anatomic Features in Victims of Sudden Coronary Death, Coronary Artery Pathology," Circulation, Supplement I, 1992, pp. 119-124, vol. 85, No. 1.
Davies et al., "The effect of temperature and oleate adsorption on the growth of maghemite particles," Journal of Magnetism and Magnetic Materials, 1993, pp. 24-28, vol. 122.
de Korte et al., "Characterization of plaque components and vulnerability with intravascular ultrasound ?elastography," Phys. Med, Biol., 2000, pp. 1465-1475, vol. 45.
Deng et al., "Magnetic and conducting Fe3O4-cross-linked polyaniline nanoparticles with core-shell structure," Polymer, 2002, pp. 2179-2184, vol. 43.
Deng et al., "Preparation of magnetic polymeric particles via inverse microemulsion polymerization process," Journal of Magnetism and Magnetic Materials, 2003, pp. 69-78, vol. 257.
Di Cera, "Thrombin," Mol. Aspects Med., 2008, pp. 203-254, vol. 29, No. 4.
Dinisio, M. et al., "Drug Therapy—Direct Thrombin Inhibitors," The New England Journal of Medicine, Sep. 8, 2005, pp. 1028-1040, vol. 353.
Dresco et al., "Preparation and Properties of Magnetite and Polymer Magnetite Nanoparticles," Langmuir, 1999, pp. 1945-1951, vol. 15, No. 6.
Dubertret et al., "In Vivo Imaging of Quantum Dots Encapsulated in Phospholipid Micelles," Science, 2002, pp. 1759-1762, vol. 298.
Duguid, "Thrombosis As a Factor in the Pathogenesis of Coronary Atherosclerosis," J Path Bact., 1946, pp. 207-212, vol. 58.
Duguid, "Thrombosis As a Factor in the Pathogenesis of Aortic Atherosclerosis," J Path Bact., 1948, pp. 57-61, vol. 60.
Extended European Search Report dated Jan. 2, 2014 from related European Patent Application No. EP 08837973.0; 9 pgs.
Extended European Search Report dated May 6, 2014 from related European Patent Application No. 11769698.9; 8 pgs.
Extended European Search Report dated May 27, 2015 from related European Patent Application No. 10842655; 12 pgs.
Fareed et al., "Changing trends in anti-coagulant therapies. Are heparins and oral anti-coagulants challenged?," International Journal of Angiology, 2008, pp. 176-192, vol. 27, No. 3.
Feltin et al., "New Technique for Synthesizing Iron Ferrite Magnetic Nanosized Particles," Langmuir, 1997, pp. 3927-3933, vol. 13, No. 15.
Flacke et al., "Novel MRI Contrast Agent for Molecular Imaging of Fibrin: Implications for Detecting Vulnerable Plaques," Circulation, 2001, pp. 1280-1285, vol. 104.
Myerson, J. et al., "Thrombin-Inhibiting Nanoparticles Rapidly Constitute Versatile and Detectable Anticlotting Surfaces," HHS Public Access Author Manuscript, Nanotechnology, Oct. 3, 2014, 21 pg., vol. 25, No. 39.
Nelson, D. et al., Lehninger Principle of Biochemistry, 2000, Third Edition, Chapter 12, pp. 392-393, Worth Publishers, New York, New York.
Notice of Acceptance dated Apr. 20, 2016 from related Australian Patent Application No. 2010339809; 4 pgs.
Notice of Allowance dated Mar. 1, 2016 from related U.S. Appl. No. 12/682,098; 4 pgs.
Notice of Allowance dated Apr. 11, 2016 from related U.S Appl. No. 13/641,252; 9 pgs.
Office Action dated Jun. 22, 2015 from related U.S. Appl. No. 12/682,098; 27 pgs.
Office Action dated May 9, 2013 from related U.S. Appl. No. 12/682,098; 17 pgs.
Office Action dated Jun. 11, 2012 from related U.S. Appl. No. 12/682,098; 15 pgs.
Office Action dated Jan. 14, 2013 from related U.S. Appl. No. 12/682,094; 16 pgs.
Office Action dated May 7, 2012 from related U.S. Appl. No. 12/682,094; 15 pgs.
Office Action dated Oct. 23, 2013 from related U.S. Appl. No. 13/516,528; 20 pgs.
Office Action dated May 27, 2014 from related U.S. Appl. No. 13/516,528; 7 pgs.
Office Action dated Dec. 9, 2014 from related U.S. Appl. No. 13/516,528; 6 pgs.
Office Action dated Sep. 14, 2015 from related U.S. Appl. No. 13/516,528; 11 pgs.
Office Action dated Apr. 8, 2016 from related U.S. Appl. No. 13/516,528; 10 pgs.
Office Action dated Nov. 3, 2016 from related U.S. Appl. No. 13/516,528; 13 pgs.
Office Action (Advisory) dated Feb. 23, 2015 from related U.S. Appl. No. 13/516,528; 3 pgs.
Office Action dated Sep. 30, 2015 from related U.S. Appl. No. 13/641,252; 20 pgs.
Office Action dated Jun. 26, 2015 from related U.S. Appl. No. 13/641,252; 11 pgs.
Office Action dated Dec. 10, 2015 from related Australian Patent Application No. 2010339809; 3 pgs.
Office Action dated Oct. 18, 2016 from related Canadian Patent Application No. 2,796,435; 3 pgs.
Office Action dated Jul. 20, 2011 from related Chinese Patent Application No. 200880117661.5; 11 pgs.
Office Action dated Jun. 4, 2012 from related Chinese Patent Application No. 200880117661.5; 17 pgs.
Office Action dated Jan. 7, 2013 from related Chinese Patent Application No. 200880117661.5; 13 pgs.

(56) References Cited

OTHER PUBLICATIONS

Office Action dated Jul. 25, 2013 from related Chinese Patent Application No. 200880117661.5; 13 pgs.
Office Action dated Dec. 4, 2013, from related Chinese Patent Application No. 201180029772.2; 13 pgs., with English translation.
Office Action dated Nov. 9, 2016 from related European Patent Application No. 10842655.2; 8 pgs.
Office Action dated Oct. 27, 2016 from related European Patent Application No. 11769698.9; 5 pgs.
Office Action dated Jan. 15, 2015 from related Japanese Patent Application No. 2013-505192; 2 pgs.
Pan, et al., "Water Soluble Nano-Bialys: Preparation of a Vascularly Constrained, Slow Releasing Nano-Carrier for Hydrophilic and Hydrophobic Drugs," American Chemical Society, Frontiers in Chemistry, Biopharmaceuticals & Biotechnology, Western Regional Meeting, Oct. 9-13, 2007, 1 pg.
Pan et al., "Lipid membrane editing with peptide cargo linkers in cells and synthetic nanostructures," FASEB J., Aug. 2010, pp. 2928-2937, vol. 24, No. 8.
Pan et al., "Anti-Angiogenesis Therapy in the Vx2 Rabbit Cancer Model with Lipase-cleavable Sn 2 Taxane Phospholipid Prodrug using [alpha]v[beta]3-Targeted Theranostic Nanoparticles," Theranostics, 2014, pp. 565-578, vol. 4, No. 6.
Partlow et al., "19F magnetic resonance imaging for stem/progenitor cell tracking with multiple unique perfluorocarbon nanobeacons," The FASEB Journal, 2007, pp. 1647-1654, vol. 21.
Pasparakis, "Regulation of tissue homeostasis by NF-κB signalling: implications for inflammatory diseases," Nature Reviews/Immunology, 2009, pp. 778-788, vol. 9.
Peters et al., "Targeting atherosclerosis by using modular, multifunctional micelles," PNAS, 2009, pp. 9815-9819, vol. 106, No. 24.
Petrasek et al., "Precise Measurement of Diffusion Coefficients using Scanning Fluorescence Correlation Spectroscopy," Biophysical Journal, 2008, pp. 1437-1448, vol. 94, No. 4.
Qiu et al., "Novel, Fluorescent, Magnetic, Polysaccharide-Based Microsphere for Orientation, Tracing, and Anticoagulation: Preparation and Characterization," Biomacromolecules, 2005, pp. 1041-1047, vol. 6, No. 2.
Raj et al., "Commercial Applications of Ferrofluids," Journal of Magnetism and Magnetic Materials, 1990, pp. 233-245, vol. 85.
Rhoades et al., "Quantification of α-Synuclein Binding to Lipid Vesicles Using Fluorescence Correlation Spectroscopy," Biophysical Journal, 2006, pp. 4692-4700, vol. 90, No. 12.
Roath, "Biological and biomedical aspects of magnetic fluid technology," Journal of Magnetism and Magnetic Materials, 1993, pp. 329-334, vol. 122.
Roger et al., "Some biomedical applications of ferrofluids," The European Physical Journal Applied Physics, 1999, pp. 321-325, vol. 5.
Rosensweig, "Magnetic Fluids: Tiny ferromagnetic particles suspended in an organic liquid form a new kind of fluid responsive to magnetic fields in queer but useful ways," International Science and Technology, 1966, pp. 48-56.
Rothwarf D. et al., "IKK-Gamma is an essential regulatory subunit of the IκB kinase complex," Nature, 1998, pp. 297-300, vol. 395.
Schwartz et al., "Microemboli and Microvascular Obstruction in Acute Coronary Thrombosis and Sudden Coronary Death," Journal of the American College of Cardiology, 2009, pp. 2167-2173, vol. 54, No. 23.
Sie et al., "Constitutional Heparin Co-Factor II Deficiency Associated with Recurrent Thrombosis," The LANCET, 1985, pp. 414-416, vol. 2.
Smale, "Selective Transcription in Response to an Inflammatory Stimulus," Cell, 2010, pp. 833-844, vol. 140, No. 6.
Soman et al., "Molecularly targeted nanocarriers deliver the cytolytic peptide melittin specifically to tumor cells in mice, reducing tumor growth," The Journal of Clinical Investigation, 2009, pp. 2830-2842, vol. 119, No. 9.
Soman et al., "Synthesis and Characterization of Stable Fluorocarbon Nanostructures as Drug Delivery Vehicles for Cytolytic Peptides," Nano Lett., 2008, pp. 1131-1136, vol. 8, No. 4.
Srivastava et al., "Progress in the Design of Low Molecular Weight Thrombin Inhibitors," Medicinal Research Reviews, 2005, pp. 66-92, vol. 25, No. 1.

\* cited by examiner

ANTITHROMBOTIC NANOPARTICLE

CROSS REFERENCE TO RELATED APPLICATIONS

This application claims the priority of U.S. Provisional Application No. 62/249,126, filed Oct. 30, 2015, and claims the priority of U.S. Ser. No. 13/516,528 filed Oct. 31, 2012, which claims the priority of PCT Application PCT/US2010/61103, filed Dec. 17, 2010, which claims the priority of U.S. Provisional Application No. 61/287,582, filed Dec. 17, 2009, each of which is hereby incorporated by reference in its entirety.

GOVERNMENTAL RIGHTS

This invention was made with government support under grant number HL073646 and HL112303 awarded by the National Institutes of Health. The government has certain rights in the invention.

FIELD OF THE INVENTION

The invention encompasses an antithrombotic nanoparticle, and use thereof.

BACKGROUND OF THE INVENTION

Millions of people die or are disabled each year from acute stroke or heart attack that is caused by the highly localized formation of blood clots resulting in occlusion of the carotid or coronary arteries. In cases where premonitory symptoms or signs of disease indicate the risk of an acute event, a cocktail of various anticoagulants and antiplatelet agents is administered both orally and intravenously to prevent clot progression. Even with aggressive treatment regimens, however, thrombus formation may still proceed unpredictably. Additionally, severe or fatal bleeding problems may arise with the systemically active anticoagulants in use today. Accordingly, there is a need in the art for the development of safer and more effective antithrombotics.

SUMMARY OF THE INVENTION

One aspect of the present invention encompasses an antithrombotic nanoparticle. Generally speaking, the exterior of the nanoparticle comprises at least one high affinity coagulation inhibitor that is substantially retained on the exterior of the nanoparticle after administration of the nanoparticle to a subject, such that the nanoparticle is antithrombotic but does not substantially alter the clotting time of the subject's blood plasma.

Another aspect of the present invention encompasses an antithrombotic nanoparticle. Usually the half-life of the nanoparticle is between about 2 and about 4 hours in a subject, and the exterior of the nanoparticle comprises at least one high affinity coagulation inhibitor that is substantially retained on the exterior of the nanoparticle after administration of the nanoparticle to a subject. Additionally, the second order kinetic constant of the nanoparticle is greater than the second order kinetic constant of the high affinity coagulation inhibitor by itself.

Yet another aspect of the invention encompasses a composition. The composition typically comprises a plurality of platelets, fibrin, and at least one nanoparticle, wherein the exterior of the nanoparticle comprises at least one high affinity coagulation inhibitor that is substantially retained on the exterior of the nanoparticle after in vivo administration of the nanoparticle.

Still another aspect of the invention encompasses a method of decreasing thrombus formation in a subject. The method generally comprises administering a nanoparticle to the subject. The half-life of the nanoparticle is typically between about 2 and about 4 hours in a subject, the exterior of the nanoparticle comprises at least one high affinity coagulation inhibitor that is substantially retained on the exterior of the nanoparticle after administration of the nanoparticle to a subject, and the second order kinetic constant of the nanoparticle is greater than the second order kinetic constant of the high affinity coagulation inhibitor by itself.

A further aspect of the invention encompasses a method of preventing thrombus formation in a subject. The method generally comprises administering a nanoparticle to the subject. The half-life of the nanoparticle is between about 2 and about 4 hours in a subject, the exterior of the nanoparticle comprises at least one high affinity coagulation inhibitor that is substantially retained on the exterior of the nanoparticle after administration of the nanoparticle to a subject, and the second order kinetic constant of the nanoparticle is greater than the second order kinetic constant of the high affinity coagulation inhibitor by itself.

Still a further aspect encompasses a method of imaging a thrombus in a subject. The method typically comprises administering a nanoparticle to the subject. The half-life of the nanoparticle is between about 2 and about 4 hours in a subject, the exterior of the nanoparticle comprises at least one high affinity coagulation inhibitor that is substantially retained on the exterior of the nanoparticle after administration of the nanoparticle to a subject, and the second order kinetic constant of the nanoparticle is greater than the second order kinetic constant of the high affinity coagulation inhibitor by itself.

Other aspects and iterations of the invention are described in more detail below.

BRIEF DESCRIPTION OF THE FIGURES

The application file contains at least one photograph executed in color. Copies of this patent application publication with color photographs will be provided by the Office upon request and payment of the necessary fee.

DETAILED DESCRIPTION OF THE INVENTION

Figure 1A:
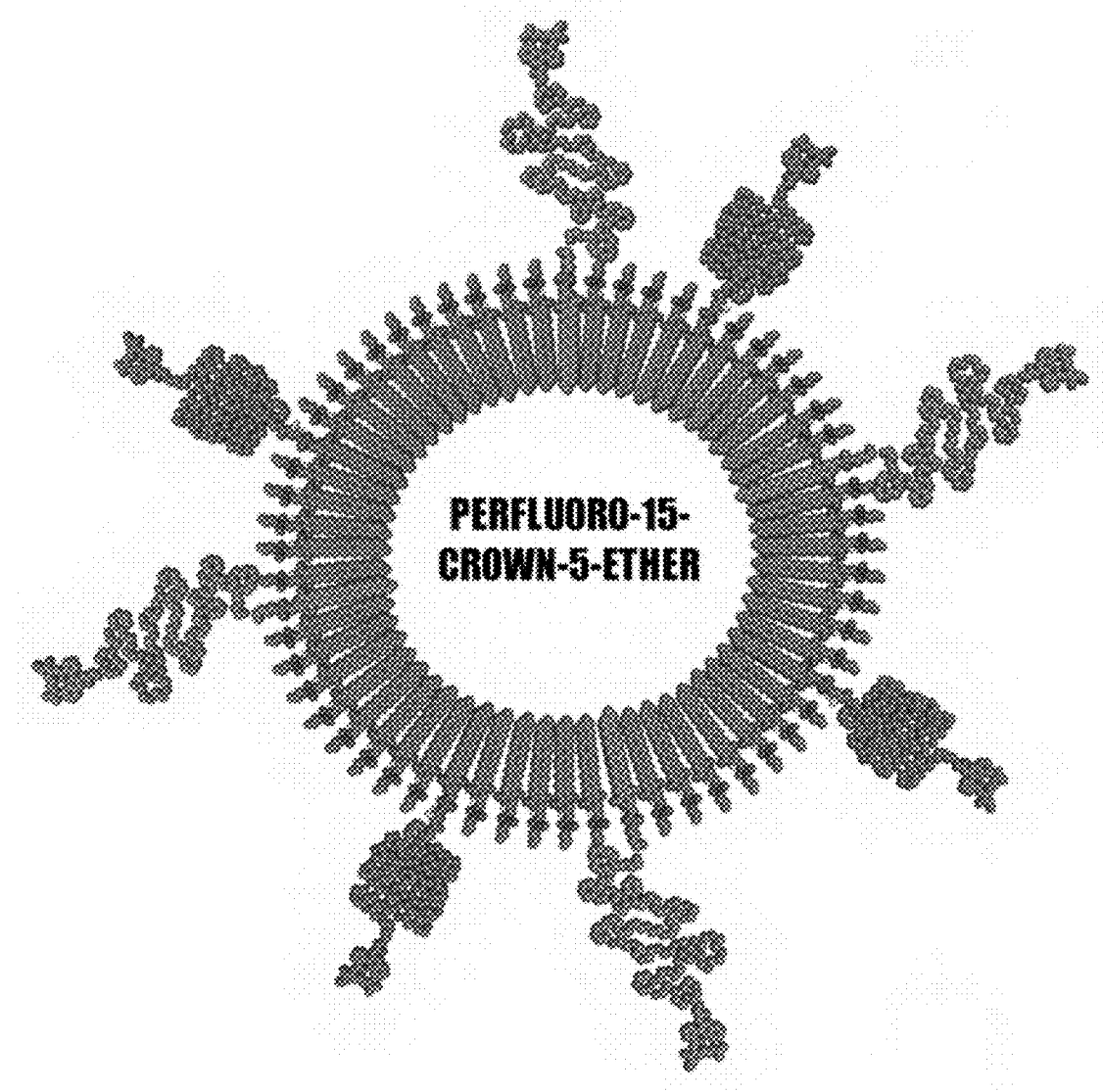
FIG. 1A-D depict various aspects of a PPACK-functionalized PFC-core nanoparticle. (A) depicts a schematic of the PPACK-functionalized PFC-core nanoparticle. The majority of the phospholipid monolayer comprised an egg lecithin L-α-phosphatidylethanolamine layer. 1% of the lipid film was 1,2-distearoyl-sn-glycero-3-phosphoethanolamine-N-[carboxy(polyethylene glycol)-2000], functionalized with PPACK after particle synthesis (B). Particle size (C) was measured before and after addition of PPACK to 1,2-distearoyl-sn-glycero-3-phosphoethanolamine-N-[carboxy (polyethylene glycol)-2000] in the lipid film. The addition of PPACK did not significantly change the mean hydrodynamic particle diameter of 158.0±2.4 nm (top panel). Corresponding to conjugation of positively charged PPACK to carboxy-terminated lipids, the particle zeta potential rose from −35±1.57 mV to −22.3±1.57 mV after functionalization (D).

The present invention provides an antithrombotic nanoparticle. Importantly, the nanoparticle is itself an integral part of the antithrombotic, as opposed to the nanoparticle simply serving as a delivery vehicle for an antithrombotic payload. The invention further provides methods of using an antithrombotic nanoparticle of the invention to prevent or decrease the formation of a thrombus in a subject.

I. Antithrombotic Nanoparticle

One aspect of the present invention encompasses an antithrombotic nanoparticle. Generally speaking, an antithrombotic nanoparticle of the invention comprises a nanoparticle structure and a high affinity coagulation inhibitor. In one embodiment, an antithrombotic nanoparticle may have anticoagulant activity. In another embodiment, an antithrombotic nanoparticle may have antiplatelet activity. In some embodiments, an antithrombotic nanoparticle may have both anticoagulant activity and antiplatelet activity. "Anti-coagulation activity," as used herein, refers to the ability to decrease fibrin based coagulation. In one embodiment, "anti-platelet activity," as used herein, refers to the ability to decrease platelet activation. In another embodiment, "anti-platelet activity" refers to the ability to decrease the density of platelets in a thrombus. In still another embodiment, "anti-platelet activity" refers to both decreasing the activation of platelets and decreasing the density of platelets in a thrombus. Methods of measuring anticoagulant and antiplatelet activity are known in the art. In one embodiment, the methods detailed in the Examples below may be used. In certain embodiments, a nanoparticle of the invention may be a PAR inhibitor.

Advantageously, a nanoparticle of the invention, while being antithrombotic at sites of active thrombus formation in a subject, does not substantially alter the clotting time of the subject's plasma. In this regard, "substantially" means that within about 20 min after intravenous administration of the nanoparticle to a subject, the subject's clotting time, as measured by an antithrombotic assay, such as an APTT assay, is about the same as the clotting time in a non-treated plasma sample.

In certain embodiments, the half-life of the antithrombotic nanoparticle after a single intravenous bolus is between about 2 hours and about 4 hours. As used herein, "half-life" refers to the elimination rate of the nanoparticle. In another embodiment, the half-life is between about 2.5 hours and about 3.5 hours. In yet another embodiment, the half-life is between about 2.75 hours and about 3.25 hours. In still another embodiment, the half-life is about 3 hours. In exemplary embodiments, a nanoparticle of the invention does not substantially alter the clotting time of the subject's plasma and has a half-life between about 2 hours and about 4 hours after a single intravenous bolus.

Generally speaking, a nanoparticle of the invention may have a more desirable kinetic constant than a high affinity coagulation inhibitor by itself. For instance, a nanoparticle of the invention comprising a high affinity coagulation inhibitor may have a greater second order kinetic constant than the second order kinetic constant of the high affinity coagulation inhibitor itself. Methods of calculating kinetic constants are known in the art. For more details, see the examples. In an exemplary embodiment, a nanoparticle of the invention does not substantially alter the clotting time of the subject's plasma, has a half-life between about 2 hours and about 4 hours, and has a greater second order kinetic constant than the high affinity inhibitor itself.

As stated above, in each of the above embodiments, a nanoparticle of the invention comprises a nanoparticle structure and a high affinity coagulation inhibitor. Each is discussed in more detail below.

(a) Nanoparticle Structure

As used herein, "nanoparticle" is used to refer to a nanostructure that is typically between about 5 nM and 400 nM across the largest dimension of the structure. A nanoparticle of the invention may be spherical, but is not required to be spherical. Regardless of the shape of the nanoparticle, the exterior of the nanoparticle should be capable of comprising at least one high affinity coagulation inhibitor.

A nanoparticle comprising an antithrombotic composition of the invention may typically be between about 5 nm and 400 nm across the largest dimension, but in some instances, may be bigger or smaller. In another embodiment, the average size of a plurality of nanoparticles in a composition may typically be between about 5 nm and 400 nm across the largest dimension. In one embodiment, the largest dimension of a nanoparticle of the invention may be between about 100 nm and about 300 nm. In another embodiment, the largest dimension of a nanoparticle may be between about 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 nm.

In certain embodiments, a nanoparticle of the invention may be a perfluorocarbon nanoparticle. Such nanoparticles are known in the art. For instance, see U.S. Pat. Nos. 5,690,907; 5,780,010; 5,989,520 and 5,958,371, each hereby incorporated by reference in their entirety.

Useful perfluorocarbon emulsions are disclosed in U.S. Pat. Nos. 4,927,623, 5,077,036, 5,114,703, 5,171,755, 5,304,325, 5,350,571, 5,393,524, and 5,403,575 and include those in which the perfluorocarbon compound is perfluorodecalin, perfluorooctane, perfluorodichlorooctane, perfluoro-n-octyl bromide, perfluoroheptane, perfluorodecane, perfluorocyclohexane, perfluoromorpholine, perfluorotripropylamine, perfluortributylamine, perfluorodimethylcyclohexane, perfluorotrimethylcyclohexane, perfluorodicyclohexyl ether, perfluoro-n-butyltetrahydrofuran, and compounds that are structurally similar to these compounds and are partially or fully halogenated (including at least some fluorine substituents) or partially or fully perfluorinated including perfluoroalkylated ether, polyether or crown ether. In some embodiments, the perfluorocarbon compound is perfluoro-n-octyl bromide. In other embodiments, the perfluorocarbon compound may be a perfluoroalkylated crown ether.

The coating which comprises lipid/surfactant to form an outer coating on the nanoparticles may include natural or synthetic phospholipids, fatty acids, cholesterols, lysolipids, sphingomyelins, and the like, including lipid conjugated polyethylene glycol. Various commercial anionic, cationic, and nonionic surfactants can also be employed, including Tweens, Spans, Tritons, and the like. Some surfactants are themselves fluorinated, such as perfluorinated alkanoic acids such as perfluorohexanoic and perfluorooctanoic acids, perfluorinated alkyl sulfonamide, alkylene quaternary ammonium salts and the like. In addition, perfluorinated alcohol phosphate esters can be employed. Cationic lipids, including DOTMA, N-[1-(2,3-dioleoyloxy)propyl]-N,N,N-trimethyl-ammonium chloride; DOTAP, 1,2-dioleoyloxy-3-(trimethyl-ammonio)propane; DOTB, 1,2-dioleoyl-3-(4'-trimethyl-ammonio)butanoyl-sn-glycerol, 1,2-diacyl-3-trimethylammonium-propane; 1,2-diacyl-3-dimethylammonium-propane; 1,2-diacyl-sn-glycerol-3-ethyl phosphocholine; and 3.beta.-[N',N'-dimethylaminoethane)-carbamol]cholesterol-HCl, may also be used.

Perfluorocarbon nanoparticles are typically formed by microfluidizing a mixture of the fluorocarbon lipid which forms the core and the lipid/surfactant mixture which forms the outer layer in suspension in aqueous medium to form an emulsion. Sonication or other techniques may be required to obtain a suspension of the lipid/surfactant in the aqueous medium. The components of the outer layer may also be coupled to imaging agents or radionuclides.

Other nanoparticle structures besides perfluorocarbon nanoparticles may be used in the present invention. In one embodiment, the nanoparticle structure comprises a lipid head group. For instance, a nanoparticle structure may be a liposome. Additionally, by way of non-limiting example, nanoparticles described in PCT Application numbers PCT/US2008/079404 and PCT/US2008/079414 may be used. Furthermore, in certain embodiments a colloid substance may be used as a nanoparticle of the invention. Non-limiting examples of other nanoparticle structures may include dendrimers and block di/tri copolymers. In some embodiments, cells or portions of cells may be used as the nanoparticle structure. For instance, in certain embodiments, a red blood cell or a platelet may be used as a nanoparticle structure.

(b) High Affinity Coagulation Inhibitor

Typically, the exterior of the nanoparticle comprises at least one high affinity coagulation inhibitor. As used herein, "exterior" refers to the surface of the nanoparticle that contacts blood plasma when the nanoparticle is administered to a subject. Generally speaking, the high affinity coagulation inhibitor is substantially retained on the exterior of the nanoparticle after in vivo administration of the nanoparticle to a subject. Stated another way, the high affinity coagulation inhibitor is substantially not released from the exterior of the nanoparticle after in vivo administration of the nanoparticle to a subject. A high affinity coagulation inhibitor may be attached to the nanoparticle by any means known in the art, including incorporating the high affinity coagulation inhibitor into the lipid membrane of a nanoparticle or linking the high affinity coagulation inhibitor to the nanoparticle via a linking molecule such as a peptide.

The high affinity coagulation inhibitor typically binds to a biomolecule involved in the coagulation cascade with high affinity. As used herein, "high affinity" means that the once the coagulation inhibitor binds to a biomolecule in the coagulation cascade, the biomolecule is substantially not released from the coagulation inhibitor under physiological conditions. Most high affinity coagulation inhibitors will have a Kd in the one nanomolar range, or less. In some embodiments, the high affinity coagulation inhibitor forms a covalent bond with a biomolecule involved in the coagulation cascade. In other embodiments, however, the high affinity coagulation inhibitor does not form a covalent bond with a biomolecule involved in the coagulation cascade. In some embodiments, the high affinity coagulation inhibitor inactivates the biomolecule, thereby inhibiting the coagulation cascade. In certain embodiments, the high affinity coagulation inhibitor of the antithrombotic nanoparticle binds to and sequesters the biomolecule, removing it from the coagulation cascade, thereby inhibiting the cascade. Regardless of the mechanism, the high affinity coagulation inhibitor impedes the formation of a new thrombus or impedes growth of an existing thrombus.

An antithrombotic nanoparticle may comprise one or more than one different type of high affinity coagulation inhibitor. For instance, a nanoparticle may comprise one, two, three, four, five, six, seven, or more than seven different types of high affinity coagulation inhibitor. Generally speaking, irrespective of the number of different types of high affinity coagulation inhibitors, a nanoparticle of the invention typically comprises between 3,000 and 20,000 copies of a high affinity inhibitor in total. In one embodiment, an antithrombotic nanoparticle comprises between about 5,000 and about 18,000 copies of a high affinity inhibitor. In another embodiment, a nanoparticle may comprise between about 8,000 and about 15,000 copies of a high affinity inhibitor. In still another embodiment, a nanoparticle may comprise between about 10,000 copies and about 15,000 copies of a high affinity inhibitor. In some embodiments, a nanoparticle may comprise about 10,000, about 10,500, about 11,000, about 11,500, about 12,000, about 12,500, about 13,000, about 13,500, about 14,000, about 14,500, or about 15,000 copies of a high affinity inhibitor.

As stated above, a high affinity coagulation inhibitor may bind to a biomolecule involved in the coagulation cascade such that the coagulation cascade is inhibited. In some embodiments, the high affinity coagulation inhibitor binds to thrombin. A high affinity coagulation inhibitor that bind to thrombin may be a naturally occurring inhibitor, an irreversible inhibitor, a reversible covalent inhibitor, or a reversible non-covalent inhibitor. A non-limiting example of a high affinity naturally occurring inhibitor is Hirudin ($IC_{50}$ 0.3 pM). A non-limiting example of a reversible inhibitor is Bivalirudin. A non-limiting example of an irreversible inhibitor is PPACK, which interacts with thrombin by alkylation or acylation of the active site histidine and/or formation of an acyl enzyme complex through reaction with the active site serine. Generally speaking, reversible covalent thrombin inhibitors bind to the catalytic serine hydroxyl (e.g. Efegatran $K_i$ 1.2 nM). Non-limiting examples of reversible non-covalent inhibitors may include inhibitors derived from N-α-tosylarginine methyl ester (e.g. Argatroban $K_i$ 19 nM), tripeptide inhibitors (e.g. Inogatran $K_i$ 15 nM), pyridinone/pyrazinone acetamide inhibitors (e.g. L-375,378 $K_i$ 0.8 nM), benzene/benzothiophene substitution derived inhibitors (e.g. L-636,619 $K_i$ 0.7 μM), and conformationally strained inhibitors (e.g. conformationally strained bicyclic pyridones $K_i$~0.2 nM). In an exemplary embodiment, the high affinity coagulation inhibitor is PPACK. In another exemplary embodiment, a nanoparticle comprises PPACK with at least one other high affinity coagulation inhibitor. In still another exemplary embodiment, a nanoparticle comprises PPACK and Bivalirudin.

In other embodiments, the high affinity coagulation inhibitor binds to a molecule listed in Table A.

TABLE A

I (fibrinogen)
II (prothrombin)
Tissue factor
V (proaccelerin, labile factor)
VII (stable factor)
VIII (Anti Hemophilic factor A)
IX (Anti Hemophilic Factor B or Christmas factor)
X (Stuart-Prower factor)
XI (plasma thromboplastin antecedent)
XII (Hageman factor)
XIII (fibrin-stabilizing factor)
von Willebrand factor
prekallikrein
high-molecular-weight kininogen (HMWK)
fibronectin A high affinity coagulation inhibitor may be incorporated into the exterior of the nanoparticle using any method known in the art, so long as the high affinity inhibitor is substantially retained on the exterior of the nanoparticle and is substantially active once incorporated into the exterior of the nanoparticle. In this regard, "substantially active" refers to the high affinity coagulation inhibitor having at least about 85, 86, 87, 88, 89, 90, 91, 92, 93, 94, 95, 96, 97, 98, 99, or 100% of its activity once incorporated into the exterior of the nanoparticle. In one embodiment, a high affinity coagulation inhibitor may be incorporated as described in the Examples below. In another embodiment, a high affinity coagulation inhibitor may be incorporated into the exterior of a nanoparticle using linkers as described in PCT/US2009/041000.

In some embodiments, a nanoparticle of the invention may comprise a high affinity coagulation inhibitor that, by itself, has an undesirable safety profile for in vivo use. This is due, in part, because the pharmacokinetic and pharmacodynamic properties of the nanoparticle may be different than the properties of the high affinity coagulation inhibitor by itself.

(c) Imaging Agent

A nanoparticle of the invention may also comprise an imaging agent. For instance, the nanoparticle may comprise imaging/tracking agents that may be used for microscopy, e.g. fluorescent microscopy, confocal microscopy, or electron microscopy, magnetic resonance imaging, tomography, such as gamma (SPECT/CT, planar) and positron emission tomography (PET/CT), radiography, or ultrasound. Imaging/tracking agents may be detectable in situ, in vivo, ex vivo, and in vitro. Microscopy imaging/tracking agents are well known in the art, and may include fluorescent molecules such as FITC, rhodamine, and Alexafluor cyan dyes. Similarly, magnetic resonance imaging molecules, radiography imaging molecules, near infrared (NIR) and photoacoustic molecules are well known in the art, and an appropriate imaging molecule may be selected by one of skill in the art after consideration of the composition of the particle and the intended use of the particle. In certain embodiments, the nanoparticle may also comprise chelators for radiometals to be detected by nuclear imaging methods, such as PET, SPECT, and related methodologies.

(d) Other Components

A nanoparticle of the invention may further comprise other components, such as one or more anti-platelet agents, glycoprotein inhibitors, fibrinolytic agents, thrombolytic agents, antibodies, or small molecule drugs. Non-limiting examples may include streptokinase, urokinase, or tissue plasminogen.

II. Methods

A nanoparticle of the invention may be administered to a subject to prevent and/or decrease the formation of a thrombus in a subject. In one embodiment, a nanoparticle of the invention may be administered to a subject to prevent formation of a thrombus in a subject. In another embodiment, a nanoparticle of the invention may be administered to a subject to decrease the formation of a thrombus in a subject. In yet another embodiment, a nanoparticle of the invention may be used to increase the time needed for a clot to occlude a vessel.

A nanoparticle of the invention may be administered to a subject to prevent and/or decrease formation of a thrombus in both acute and non-acute situations. For instance, by way of non-limiting example, an antithrombotic nanoparticle may be administered to a subject in the acute situations of ischemia and deep vein thrombosis. Alternatively, a nanoparticle may be administered to a subject in the following non-limiting non-acute situations of stents, angioplasty, indwelling lines, artificial heart valves, shunts, or other prosthetic items in the vascular system.

In each of the above embodiments, a nanoparticle is administered to a subject. Generally speaking, a nanoparticle of the invention may be administered intravenously. A nanoparticle may also be administered orally, intramuscularly, intradermally, intraperitoneally, intralymphaticly, percutaneously, or by scarification, subcutaneous injection or other parenteral routes.

In each of the above embodiments, a nanoparticle of the invention maybe combined with a pharmaceutically acceptable vehicle or carrier. For instance, in embodiments where these compositions are administration by injection (e.g., intraperitoneally, intravenously, subcutaneously, intramuscularly, etc.), the compositions are preferably combined with pharmaceutically acceptable vehicles such as saline, Ringer's solution, dextrose solution, and the like.

One of skill in the art will recognize that the amount of a nanoparticle administered to a subject can and will vary depending on several factors, such as the size of the subject, the health of the subject, the intended use of the nanoparticle and/or the type of nanoparticle. In one embodiment, the amount of nanoparticle administered is between about 0.25 μmol/kg and about 3 μmol/kg. In another embodiment, the amount of nanoparticle administered is between about 0.5

µmol/kg and about 1.5 µmol/kg. In yet another embodiment, the amount of nanoparticle administered is about 1 µmol/kg. In still another embodiment, the amount of nanoparticle administered is between about 0.3 g/kg and about 0.4 g/kg.

Generally speaking, a nanoparticle of the invention may be administered to a subject as frequently as necessary to prevent and/or decrease the formation of a thrombus in the subject. In one embodiment, a nanoparticle may be administered every hour, every 2 hours, every 3 hours, every 4 hours, every 5 hours, every 6 hours, every 7 hours, every 8 hours, every 9 hours, every 10 hours, every 11 hours, every 12 hours, every 13 hours, every 14 hours, every 15 hours, every 16 hours, every 17 hours, every 18 hours, every 19 hours, every 20 hours, every 21 hours, every 22 hours, every 23 hours, or every 24 hours. In another embodiment, a nanoparticle may be administered once daily. In yet another embodiment, a nanoparticle may be administered every two days, every three days, every four days, every five days, every six days, or every seven days.

Suitable subjects may include rodents, companion animals, livestock animals, non-human primates, and humans. Non-limiting examples of rodents may include mice, rats, hamsters, gerbils, and guinea pigs. Non-limiting examples of companion animals may include cats, dogs, rabbits, hedgehogs, and ferrets. Non-limiting examples of livestock may include horses, goats, sheep, swine, llamas, alpacas, and cattle. Non-limiting examples of non-human primates may include capuchin monkeys, chimpanzees, lemurs, macaques, marmosets, tamarins, spider monkeys, squirrel monkeys, and vervet monkeys.

In each of the above embodiments, a nanoparticle of the invention may also be used to image a thrombus comprising one or more nanoparticles of the invention. In particular, a nanoparticle of the invention may comprise an imaging agent, such that the particle may be detected by fluorescent microscopy, confocal microscopy, or electron microscopy, magnetic resonance imaging, tomography, such as gamma (SPECT/CT, planar) and positron emission tomography (PET/CT), radiography, or ultrasound.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Introduction for Examples 1-3

In cases of cardiovascular disease, the most prevalent and costly medical emergencies faced by many millions of patients each year are the acute onset of localized thrombosis in the coronary and carotid arteries that lead to heart attack and stroke. Even with aggressive treatment with various anticoagulants and antiplatelet agents [1-5], thrombus formation can proceed unpredictably [6, 7]. Conversely, severe bleeding problems can arise using the current array of systemically active anticoagulants [8]. Furthermore, stuttering thrombosis and microembolization can affect the assessment of outcomes with current treatment strategies [9]. The development of safer and more effective anticoagulants and the tracking of clotting remain as challenges and active pursuits in research of the thrombosis-prone conditions that lead to heart attack and stroke [1, 3, 5, 10-14].

The serine protease thrombin has a central role as a rate-limiting factor in clotting. In its primary procoagulant role, thrombin converts soluble fibrinogen into insoluble fibrin that accumulates in forming clots [4, 15, and 16]. Additionally, it contributes to the activation of platelets via cleavage of G protein-coupled protease-activated receptors (PARs) [4, 15, 17-21] and plays a role upstream in the coagulation cascade through activation of factors V, VIII, and XI [22]. Elevated levels of active thrombin persist around sites of vascular injury [23]. In atherosclerosis, thrombin is associated with plaque development and susceptibility to rupture [17, 24, and 25].

Accordingly, thrombin inhibition has long been a target for development of new anticoagulants. In particular, direct thrombin inhibitors have been designed for acute treatment with high specificity and potency [2-4]. D-phenylalyl-L-prolyl-L-arginyl-chloromethyl ketone (PPACK) is an irreversible covalent inhibitor that was amongst the first direct thrombin inhibitors. The PPACK-thrombin complex has been thoroughly characterized as a stable structure [2, 4, 15, 16, and 26]. Additionally, the molecule has an excellent safety profile in vivo, with an $LD_{50}$ greater than 50 mg/kg and no long-term toxicity in mice [2, 27]. Nonetheless, therapeutic use of PPACK has been abandoned primarily due to its rapid clearance (7 minute distribution and 2.9 minute elimination half-lives).

Reported herein a perfluorocarbon (PFC) nanoparticle-based antithrombotic agent and its superiority in vivo to conventional systemic anticoagulants is demonstrated in a realistic thrombosis model. The promise of the described particle is twofold. First, it enables researchers to revisit the use of potent inhibitors such as PPACK that may have been dismissed in consideration of pharmacokinetics or pharmacodynamics. Each particle permanently carries on its surface more than 10,000 covalently conjugated PPACK molecules. Whereas PPACK itself is quickly eliminated from the blood, the PFC nanoparticle has well-established pharmacokinetics (~3 hour elimination half-life) enabling a prolonged therapeutic effect that proved to be more potent than that provided by PPACK itself [28, 29]. Secondly, the particle specifically binds at the site of thrombosis, focusing the impact of the particle at the site of injury and minimizing systemic effects. Through thrombin-specific binding and the magnetic resonance contrast provided by the particle core, particles functionalized with anti-thrombins allow visualization of a thrombotic occlusion in $^{19}$F MRI. While nanoparticles have previously been employed to carry common anticoagulants [30], none have been conceptualized or demonstrated in vivo as integrated antithrombotics where the nanoparticle itself plays a critical role in diagnosis and treatment of thrombosis. [10, 26].

Materials and Methods for Examples 1-3

Nanoparticle Synthesis

Perfluorocarbon nanoparticles were prepared as described in previous work [36]. The emulsions contained 20% (vol/vol) Perfluoro 15-Crown-5 Ether (Exfluor Research Corp.), 2% (wt/vol) of a surfactant mixture, 1.7% (wt/vol) glycerin, and water for the balance. The surfactant, including 98.5 mole % phosphatidylethanolamine (Avanti Polar Lipids) and 1.5 mole % 1,2-distearoyl-sn-glycero-3-phosphoethanolamine-N-[carboxy(polyethylene glycol)-2000] (Avanti Polar Lipids) or 98 mole % egg yolk phosphotidylcholine (Avanti Polar Lipids) and 2 mole % phosphatidylethanolamine (Avanti Polar Lipids) in chloroform:methanol (3:1), was dried under vacuum to form a lipid film. The surfactant components were combined with the crown ether and distilled de-ionized water and emulsified (Microfluidics Inc) at 20000 psi for 4 minutes. Particle sizes were measured immediately after synthesis using a laser light scattering submicron particle analyzer (Brookhaven Instruments).

To functionalize particles containing 1,2-distearoyl-sn-glycero-3-phosphoethanolamine-N-[carboxy(polyethylene glycol)-2000] with PPACK, amine-carboxyl coupling was employed to conjugate the PPACK N-terminus to the bare carboxyl groups on the synthesized particles. After one hour mixing of 1 mL emulsion with 12.5 mg PPACK, EDCI 1-[3-(Dimethylamino)propyl]-3-ethylcarbodiimide methiodide (2 mg) was added for overnight coupling. Excess PPACK and EDCI were removed by dialysis (MWCO 3000-5000). Particle size was assessed before and after PPACK conjugation as described above. Extent of PPACK coupling was determined by reverse-phase HPLC quantification of uncoupled PPACK after centrifugation of nanoparticles with Cleanascite lipid adsorption reagent (Agilent Technologies). Elution of PPACK at 22 minutes after injection in a $C_{18}$ column was achieved with an isocratic method employing 9.9% acetonitrile, 0.089% trifluoroacetic acid, and 90.011% water flowed at 1 mL/minute. PPACK was detected via phenylalanine absorbance (258 nm). Zeta potential measurements, taking into consideration hydrodynamic diameter measurements, were used for further verification of PPACK coupling (Brookhaven Instruments).

Thrombin Inhibition Experiments

Tosyl-Gly-Pro-Arg-4 nitranilide acetate (Chromozym TH, Roche Applied Science) was employed to assay PPACK inhibition of thrombin and plasmin in accordance with previously described methods [31]. 100 μL of 12 nM thrombin was incubated for one minute at room temperature with selected amounts of PPACK or PPACK-nanoparticles or with an excess of bare nanoparticles. 500 μL (100 μM) of the thrombin substrate Tosyl-Gly-Pro-Arg-4 nitranilide acetate were added to terminate the PPACK-thrombin interaction. In accordance with previous work, thrombin activity against the substrate was measured via absorbance at 405 nm. The rate of change in absorbance at 405 nm was taken as representative of the amount of uninhibited thrombin available to cleave Chromozym TH.

In additional experiments, Chromozym TH was used to determine the kinetics of the PPACK-thrombin interaction. 0.92 nM thrombin was incubated at room temperature with 5 nM PPACK or 0.3 pM PPACK nanoparticles over various times prior to introduction of 500 μL of 100 μM Chromozym TH. Thrombin activity was measured as above. Kinetics of inhibition were characterized in accordance with the work of Kettner and Shaw [26]. The assay yielded the apparent pseudo-first-order rate constant for thrombin inactivation ($k_{app}$). Modeling inhibition according to equation (1), an estimate of the second order constants ($k_2/K_i$) for the PPACK-thrombin interaction and the PPACK nanoparticle-thrombin interaction were obtained via equation (2). To best obtain a pseudo-first-order reaction, thrombin dilution was maximized within the limits set by the sensitivity of the Chromozym TH assay.

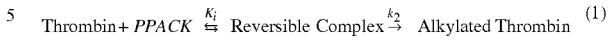

$$\text{Thrombin} + PPACK \underset{}{\overset{K_i}{\rightleftharpoons}} \text{Reversible Complex} \overset{k_2}{\rightarrow} \text{Alkylated Thrombin} \quad (1)$$

$$\frac{k_{app}}{[PPACK]} = \frac{k2}{K_i} \text{ if } [PPACK] << K_i \quad (2)$$

Chromozym TH was also used to measure PPACK and PPACK nanoparticle activity against plasmin. 120 nM Plasmin was incubated for three minutes at room temperature with selected quantities of PPACK and PPACK nanoparticles. 1000-fold excess (138 μM) of PPACK (free or on nanoparticles) was employed to produce a measurable effect on plasmin activity against Chromozym TH. Activity after incubation with PPACK and PPACK nanoparticles was compared.

Antithrombotic Effects In Vivo

As described in previous work [31, 32], 10-12 week old male C57BL/6 mice (weight 25-30 g) were subjected to photochemical injury of the carotid. After anesthetization with sodium pentobarbital, the mice were secured under a dissecting microscope for isolation of the right common carotid artery via midline cervical incision. An ultrasonic flow probe (model 0.5 VB Transonic Systems, Ithaca, N.Y.) was applied to the artery to measure flow for the duration of each experiment. A 1.5 mW 540 nm HeNe laser (Melles Griot, Carlsbad, Calif.) was focused on the artery at a distance of 6 cm. Heparin (0.125 mg/kg, n=4), PPACK (12.5 mg/kg, n=7), PPACK nanoparticles (1 mL/kg, n=7), or non-functionalized nanoparticles (1 mL/kg, n=7) were administered to the tail vein as a bolus 10 minutes prior to inducing arterial thrombus through tail vein injection of photosensitive rose bengal dye (50 mg/kg; Fisher Scientific, Fair Lawn, N.J.) dissolved in PBS. In additional control experiments (n=4), no treatment preceded injection of the rose bengal dye. Occlusion of the carotid artery was noted and experiments were terminated upon the stable (>5 minutes) maintenance of zero flow.

Occluded arteries were removed and preserved. For transmission electron microscopy, arteries were fixed in 2% glutaraldehyde and 0.1 mM sodium cacodylate at 4 degrees. Fixed tissues were stained with osmium tetroxide, tannic acid, and uranyl acetate. Tissues were then dehydrated and embedded in PolyBed 812 (Polysciences). Semi-thin sections were stained with Toluidine Blue and evaluated under light microscope for the presence of occlusive clotting. Portions of arteries identified as containing thrombi were subsequently sliced for transmission electron microscopy. Thin sections were counterstained with uranyl acetate and lead citrate. Samples were examined with a Zeiss 902 Electron Microscope and images were recorded with Kodak EM film.

For Carstair's staining, arteries were preserved in 10% buffered formalin for 3 days. After processing through alcohols and xylenes, the arteries were embedded in paraffin and sectioned at 5-micron thickness. Hydrated sections were treated with 5% ferric alum, Mayer's hematoxylin, picric acid-orange G solution, ponceau-fuchsin solution, 1% phosphotungstic acid, and aniline blue to stain for fibrin, platelets, collagen, muscle, and red blood cells. Images were analyzed for platelet content using ImageJ.

In additional mice, APTTs for blood obtained via left-ventricular draws were used to determine the systemic effects of the particles. Citrate-anticoagulated blood was obtained 10, 20, 40, 70, 110, or 150 minutes after injection of a bolus of PPACK nanoparticles or 10 minutes after injection of control nanoparticles or saline. Plasma was combined with APTT reagent (Beckman-Coulter/Instrumentation Laboratory) for three minutes prior to activation with calcium chloride and mechanical determination of coagulation time.

Imaging and Quantification of Nanoparticle Antithrombotics

Left (unaffected) and right (injured) arteries from six mice were reserved for analysis via magnetic resonance imaging and spectroscopy. Three of these mice received PPACK nanoparticles and three received blank nanoparticles prior to induction of thrombosis. Arteries were excised and rinsed with saline to remove retained blood prior to submersion in fixative as described above. Imaging and spectroscopy was conducted with a custom-built single-turn solenoid coil on a Varian 11.7 T MR system. $^{19}$F signal from nanoparticles in the artery and from a perfluorooctylbromide standard was assessed via spin echo spectroscopy (3 s pulse repetition time (TR), 2 ms echo time (TE), 256 signal averages (NT), 13.25 minute acquisition time). $^{19}$F spin echo images (1.3 s TR, 12 ms TE, 512 signal averages, 32 phase encoding steps, 64 frequency encoding steps, 9 mm×6 mm×1 mm field of view) were obtained to depict nanoparticle binding in the excised artery. 1H spin echo images (1.5 s TR, 20 ms TE, 4 signal averages, 128 phase encoding steps, 256 frequency encoding steps, 9 mm×6 mm×1 mm field of view, 5 0.2 mm slices) allowed coregistration of the fluorine images with an anatomical image of the artery.

Example 1. Nanoparticle Synthesis

Figure 1B:
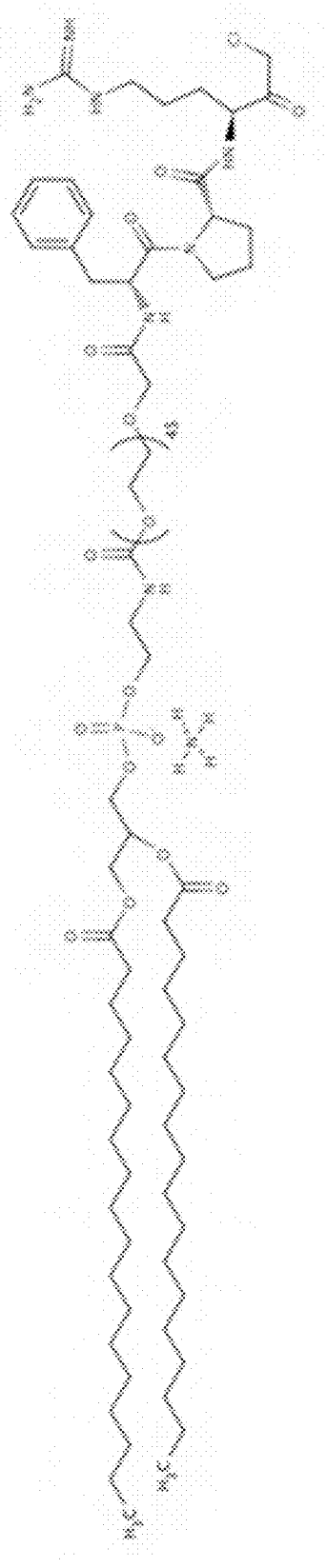
Figure 1C:
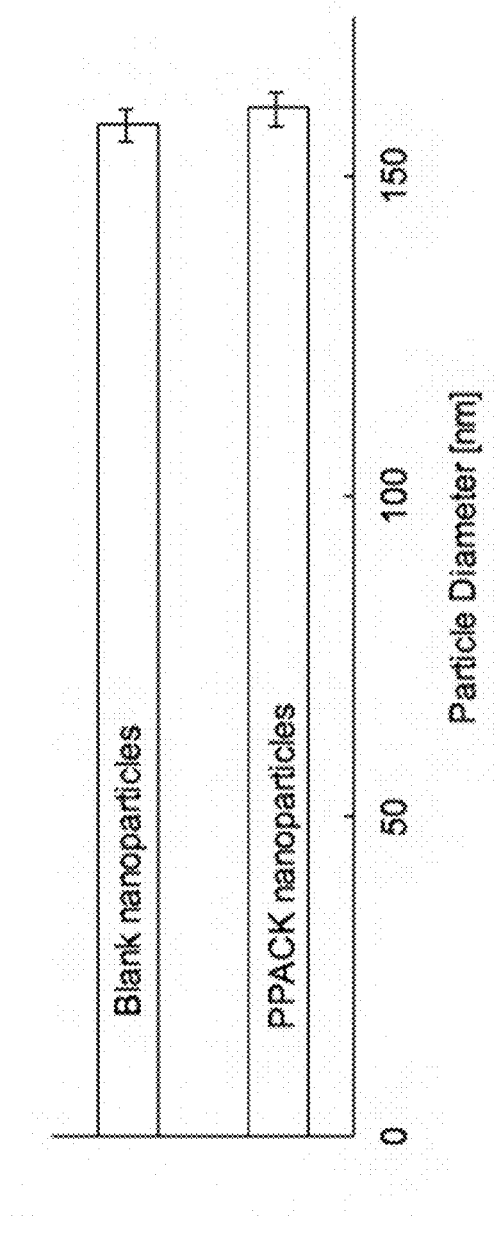

PFC nanoparticles were synthesized with inclusion of carboxy-terminated PEG capped lipids (FIG. 1A, 1B). Via EDCI coupling, amide bonds were formed between the N-terminus of PPACK and the bare carboxyls on the particle surface. After conjugation of PPACK, nanoparticles were examined to verify stability. Precursor nanoparticles were found via laser scattering to have a hydrodynamic diameter of 158.0±2.4 nm. PPACK nanoparticles had a measured diameter of 160.5 0±2.6 nm (FIG. 1C).

Figure 1D:
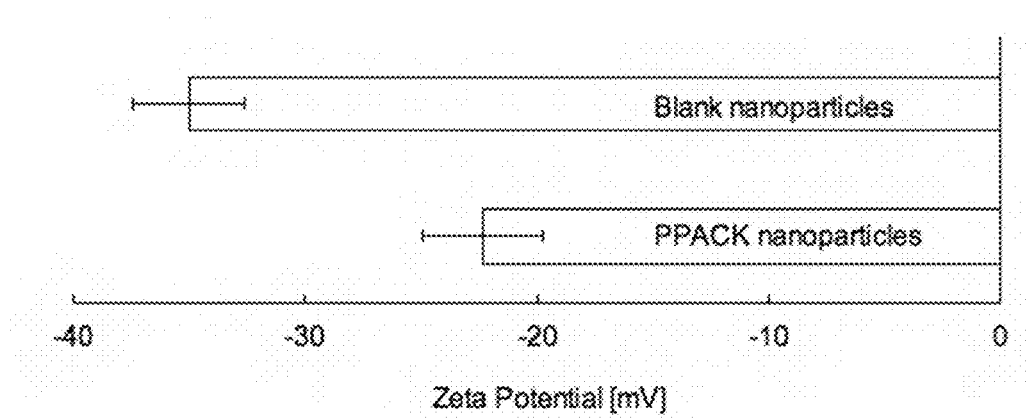

After PPACK coupling, a change in the composition of the lipid surface of the particles was evident via measurement of zeta potential. Prior to PPACK coupling, the particles exhibited a zeta potential of −35.0±1.57 mV. After addition of PPACK, the zeta potential rose to −22.3±1.57 mV, concordant with the expectation that the PPACK arginine would reduce the negative zeta potential of the non-functionalized nanoemulsions (FIG. 1D).

Figure 2:
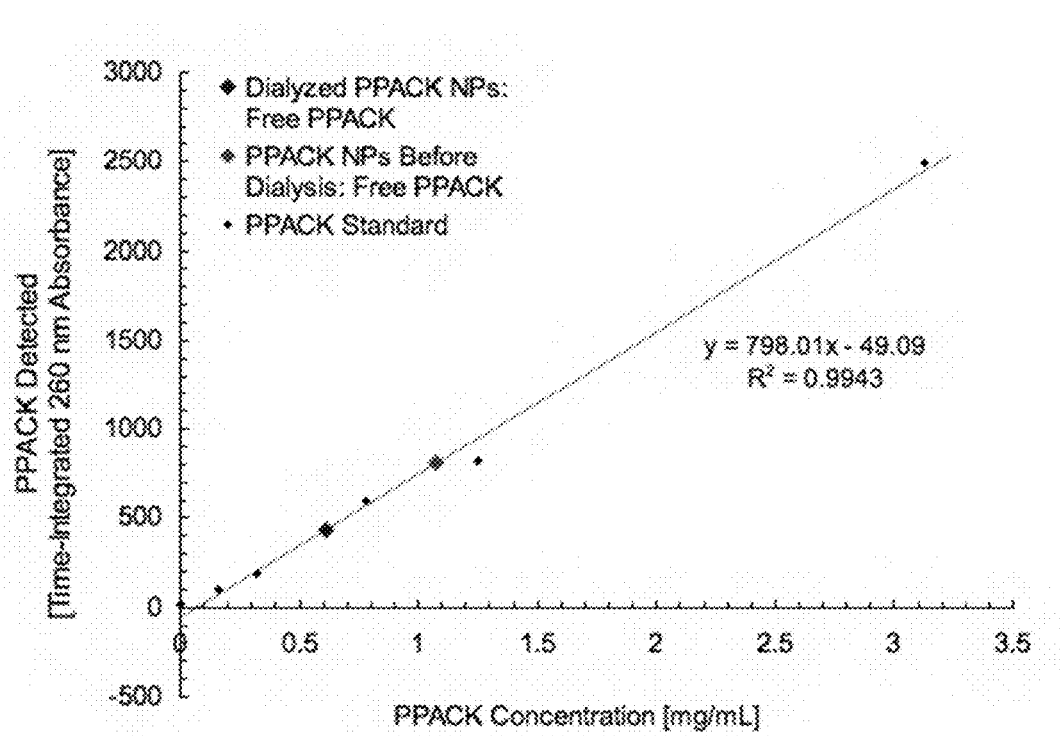
FIG. 2 depicts a graph illustrating PPACK loading on nanoparticles. Addition of ~13650 PPACK per particle was verified through HPLC quantification. The PPACK elution time for the chosen method was identified in seven samples of pure PPACK of different concentrations to generate a standard curve. Immediately after coupling of PPACK to the particles, the particles were precipitated and PPACK in the supernatant was quantified through the same method (red). Free PPACK and EDCI coupling agent were removed by dialysis and the isolated particles were precipitated identically after one week storage at 4 degrees, allowing quantification of PPACK still remaining unattached to the particles (blue).

Following synthesis but before dialysis to remove PPACK that did not couple to the particles, the residual uncoupled PPACK in the emulsion was quantified by reverse phase liquid chromatography. For PPACK nanoparticles not subject to dialysis, HPLC analysis indicated approximately 13650 PPACK coupled to each particle. HPLC also determined the amount of PPACK not associated with the particles after dialysis and one week storage at four degrees, indicating good stability of the PPACK nanoparticle formulation (FIG. 2).

Example 2. Kinetics and Specificity of Thrombin Inhibition

Figure 3A:
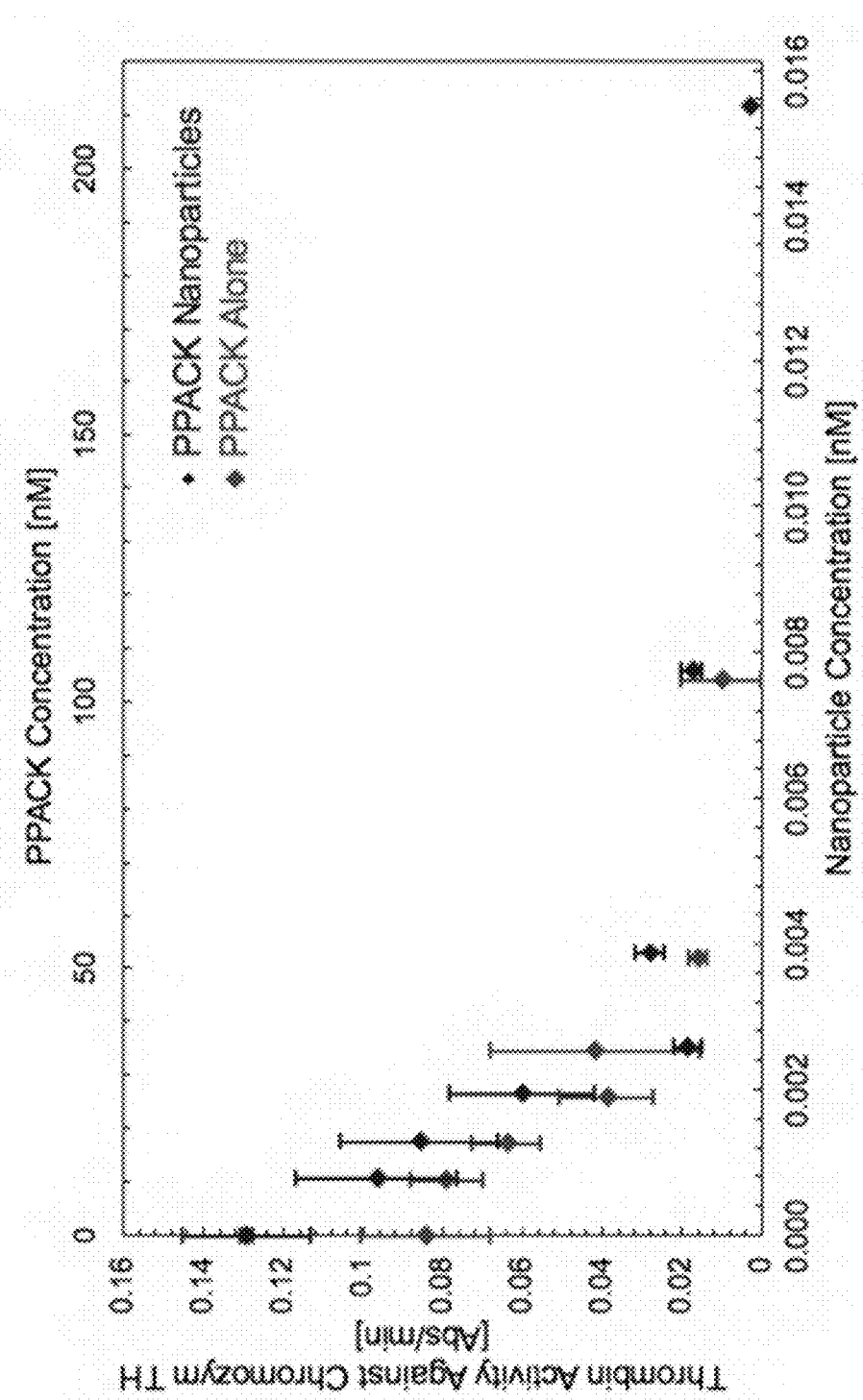
FIG. 3A-B depict graphs illustrating the activity of the antithrombotic nanoparticle. PPACK caused concentration-dependent inhibition of thrombin activity against Chromozym TH, with no significant thrombin activity apparent beyond a ten-fold excess of PPACK. For PPACK-nanoparticles, the dependence of thrombin activity on PPACK concentration was identical to that for free PPACK, accordingly indicating greater antithrombin activity per particle than per individual free PPACK (A). Study of the kinetics of thrombin-PPACK and the thrombin-PPACK nanoparticle interactions indicated no modification to PPACK activity against thrombin after placement on nanoparticles (B). For 0.93 nM thrombin and 5 nM PPACK (0.0003 nM PPACK-nanoparticles), PPACK exhibited a second order constant $(k_2/K_I)$ of $3.65 \times 10^8$ $M^{-1}min^{-1}$ and PPACK-nanoparticles exhibited a second order constant of $6.10 \times 10^{12}$ $M^{-1}min^{-1}$ (corresponding to $4.47 \times 10^8$ $M^{-1}min^{-1}$ for PPACK on the particles).

PPACK and PPACK nanoparticle inhibition of thrombin was evaluated by measuring thrombin activity on the chromogenic substrate, Chromozym TH. After one-minute incubation with either PPACK nanoparticles or free PPACK, thrombin activity against the substrate decreased monotonically with increasing inhibitor concentration (FIG. 3A). PPACK on the nanoparticles gave a decay constant of 0.033 nM$^{-1}$ and free PPACK gave a decay constant of 0.026 nM$^{-1}$, indicating no diminution of PPACK activity after conjugation to particles. Complete inhibition of thrombin activity was achieved at a 15.5 pM particle concentration, corresponding to deactivation of approximately 1000 thrombin by each particle.

Figure 3B:
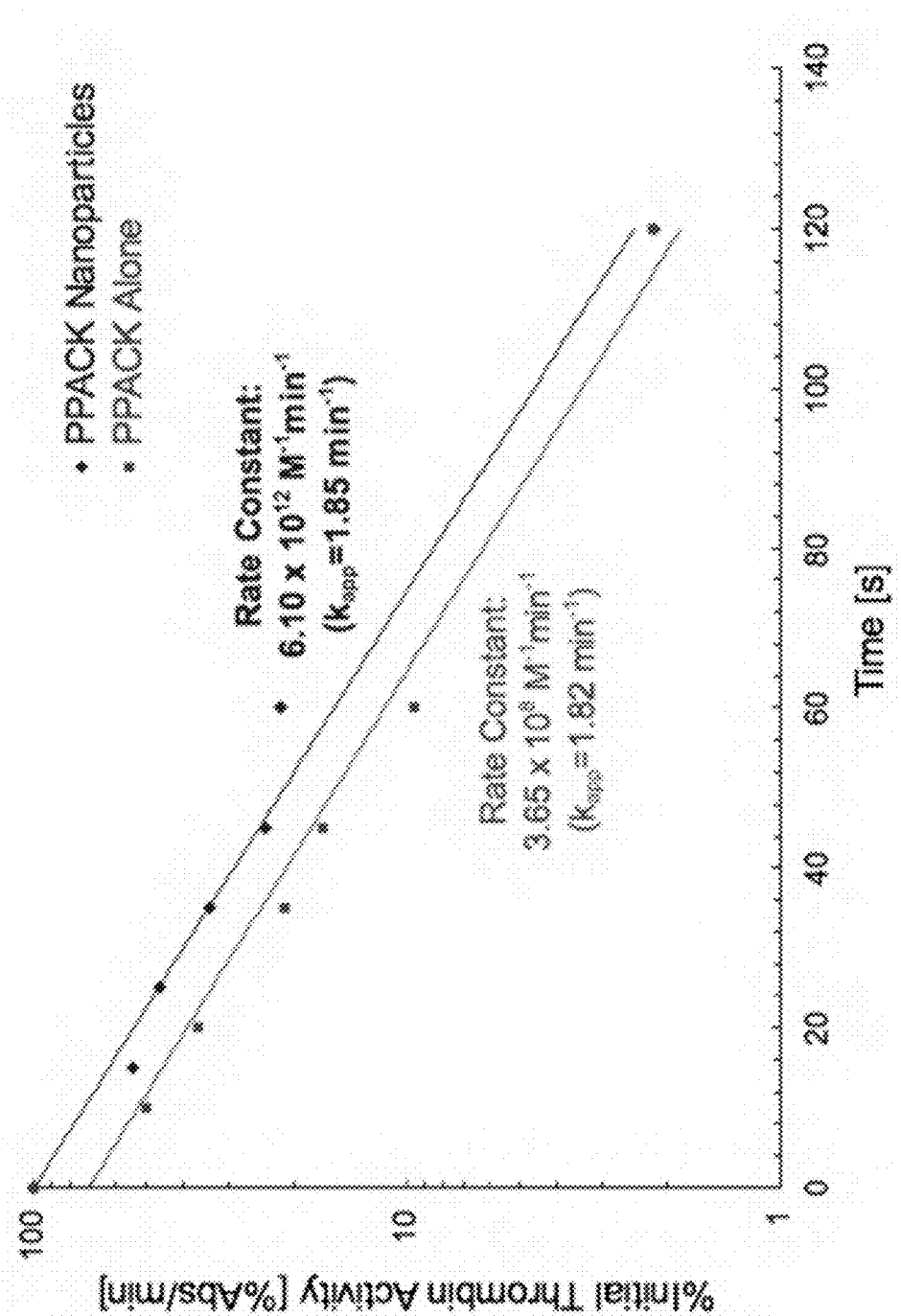

Chromozym TH assay also defined the kinetics of PPACK and PPACK nanoparticle inhibition of thrombin in accordance with the model of Kettner and Shaw (FIG. 3B). For free PPACK, the pseudo-first-order rate constant, $k_{app}$, was measured as 1.824 min$^{-1}$. The second order constant for free PPACK was approximated as $k_{app}/[\text{PPACK}]=3.65\times10^8$ M$^{-1}$min$^{-1}$ (whereas Kettner and Shaw originally found a constant of $1.20\times10^9$ M$^{-1}$min$^{-1}$ [26]). PPACK on the nanoparticles exhibited a $k_{app}$ of 1.848 min$^{-1}$ and a second order constant of $4.47\times10^8$ M$^{-1}$min$^{-1}$. The PPACK nanoparticle, considered as an inhibitor itself, exhibited a second order constant of $6.10\times10^{12}$ M$^{-1}$min$^{-1}$. PPACK nanoparticles at the site of thrombotic injury thus have a kinetic advantage over free PPACK in the inhibition of thrombus formation. Furthermore, the kinetics of the PPACK-thrombin interaction showed no significant alteration with PPACK bound to nanoparticles. Without PPACK, the nanoparticles had no effect on thrombin activity.

Figure 4:
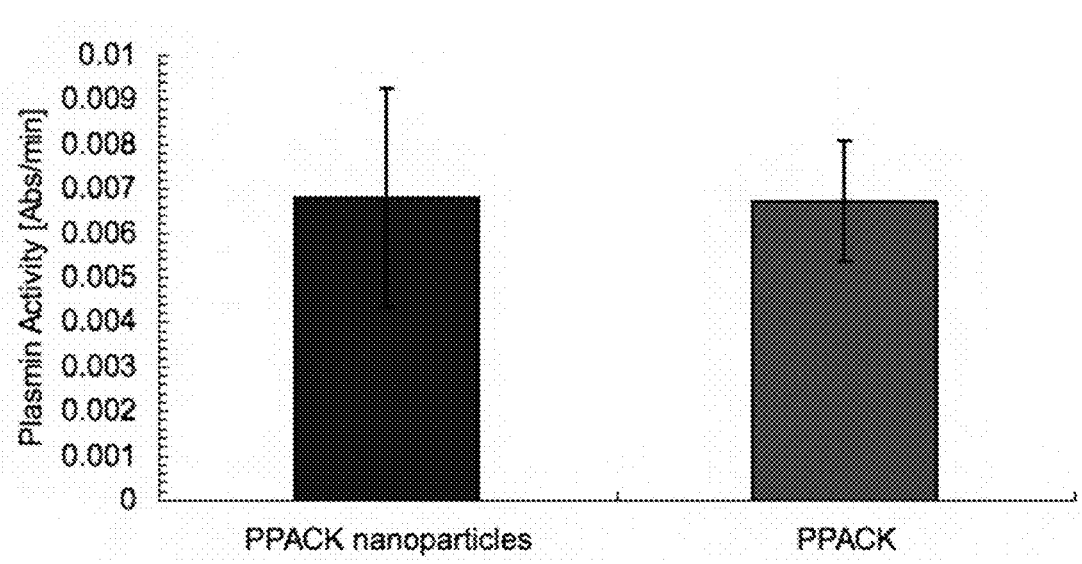
FIG. 4 depict graphs of PPACK and PPACK-nanoparticle activity against plasmin when tested via assessment of plasmin activity against Chromozym TH. A 1000-fold excess of PPACK generated 85% suppression of plasmin activity (red). Conjugation of PPACK to nanoparticles (blue) generated no additional non-specific activity against plasmin.

Chromozym TH was used to test the response of plasmin activity to PPACK and PPACK nanoparticles (FIG. 4). Greater than 80% inhibition of plasmin activity against Chromozym TH was achieved with 138 μM PPACK, both for free PPACK and particle-bound inhibitor. Conjugation of PPACK to nanoparticles constitutes an N-terminal modification to the inhibitor that does not compromise its specificity for thrombin over plasmin.

Example 3. Antithrombotic Efficacy In Vivo

Figure 5:
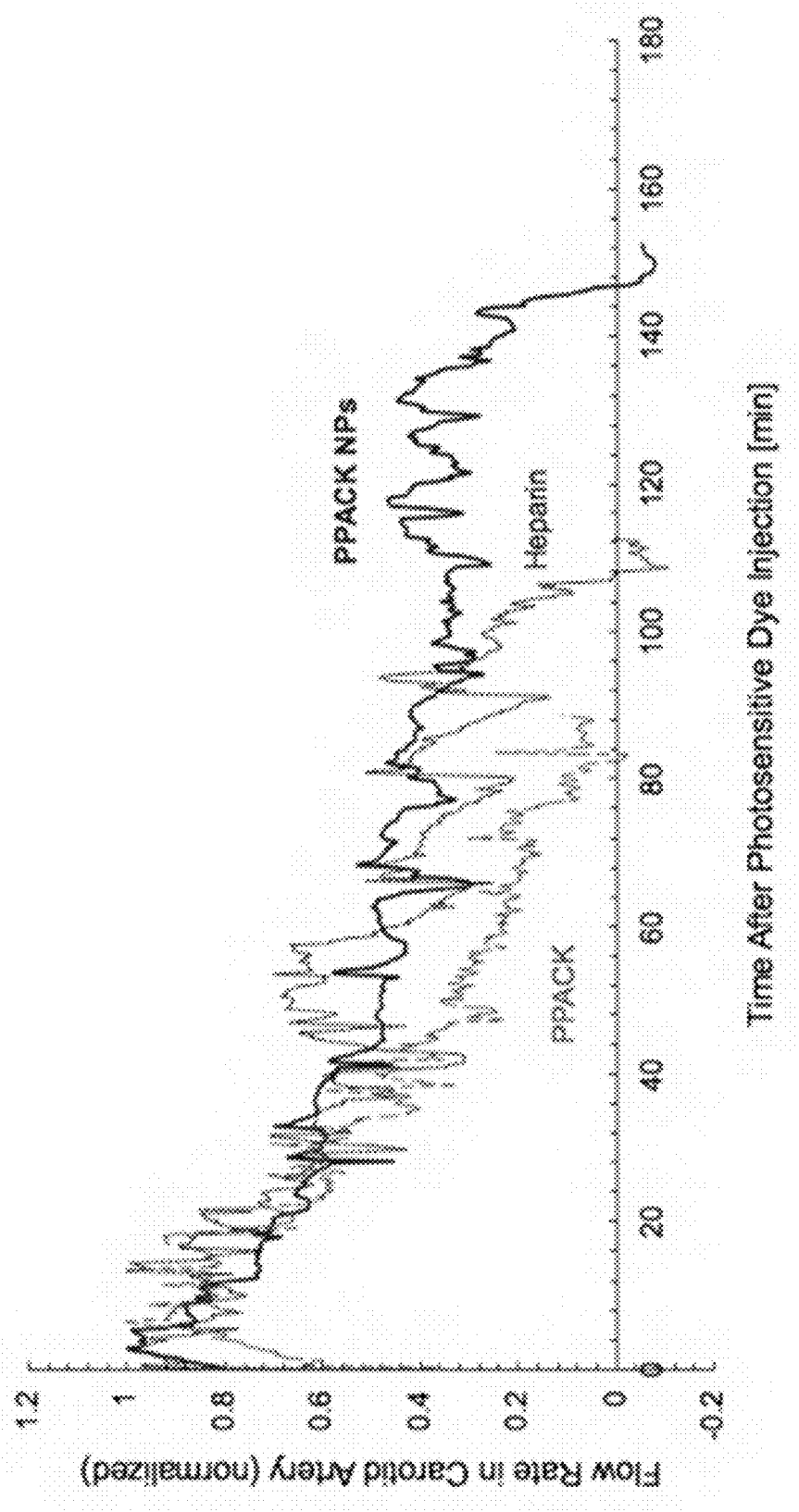
FIG. 5 depicts a graph. Photochemical injury was used to induce thrombotic occlusion of the mouse carotid artery while monitoring blood flow. Representative blood flow time courses for animals treated with PPACK (red), heparin (black), or PPACK-nanoparticles (blue) are depicted. In the presence of PPACK-nanoparticles or heparin, formation of a stable thrombus was noticeably delayed, whereas free PPACK allowed a steady approach to complete occlusion.
Figure 6A:
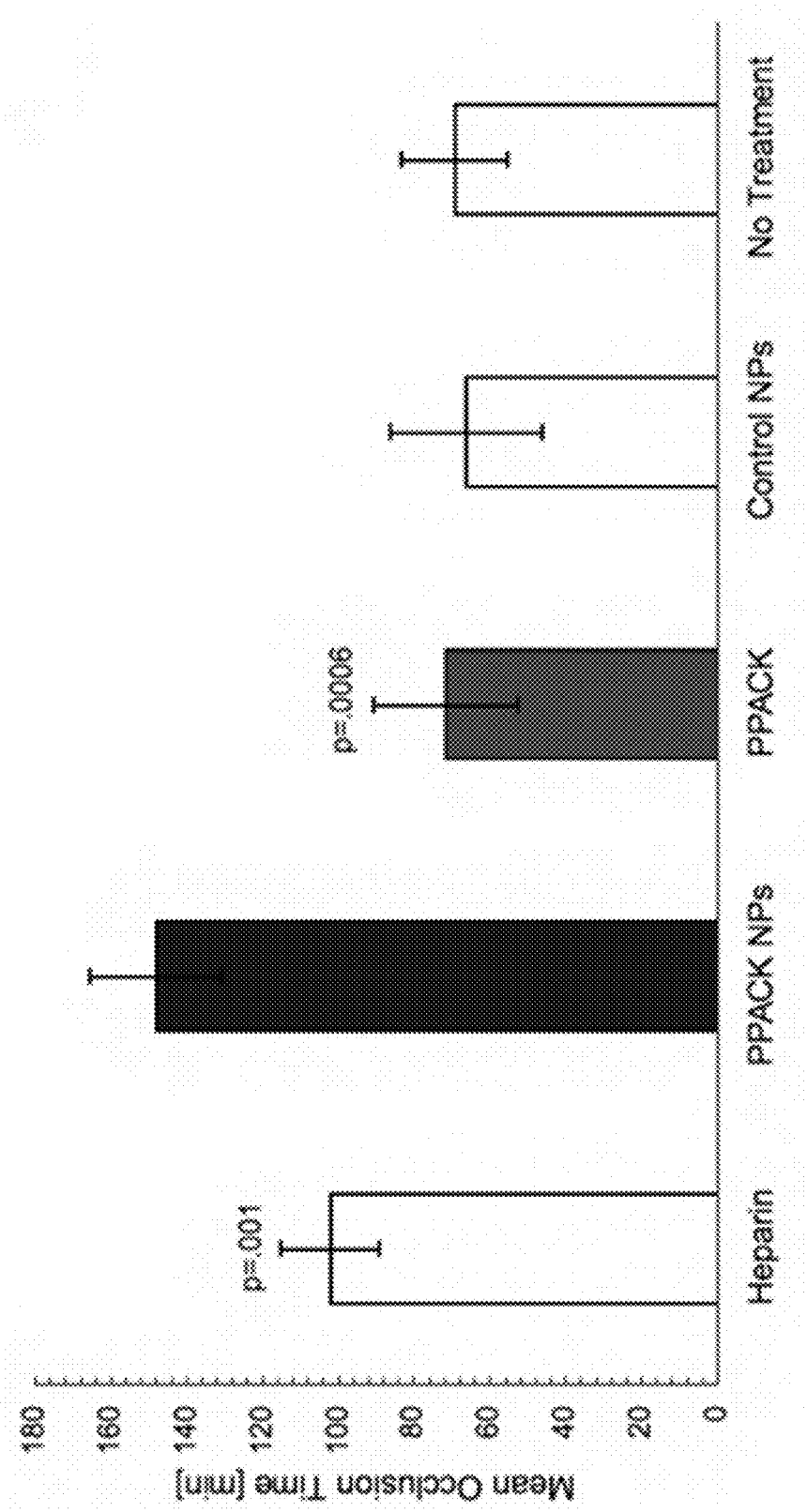
FIG. 6A-B depict graphs illustrating mean±standard deviation occlusion time for each tested treatment condition in photochemical thrombotic injury experiments. Treatment with PPACK (n=7) or non-functionalized nanoparticles (n=7) did not delay occlusion time. PPACK-nanoparticle treatment more than doubled occlusion time over PPACK-treated (p=0.0006) or non-treated mice (n=7). PPACK-nanoparticle treatment also lengthened occlusion time relative to heparin treatment (p=0.001, n=4) (A). In blood draws, PPACK nanoparticles delayed the APTT only briefly, with systemic coagulation times approaching control values over the first 20 minutes after injection (B).

In trials of the in vivo effect of PPACK nanoparticles, thrombotic occlusion of the carotid artery was induced in C57BL/6 mice. Blood flow in the carotid steadily diminished as occlusion progressed (FIG. 5). Time to occlusion indicated efficacy of fibrin and platelet deposition. Saline, heparin, non-functionalized nanoparticles, PPACK, or PPACK nanoparticles were administered ten minutes before inducing laser injury via injection of rose bengal dye (FIG. 6A). With saline sham treatment, carotid artery occlusion occurred at 70±17 minutes after dye injection. Following a bolus of control nanoparticles, occlusion occurred at 66±14 minutes. PPACK alone, despite its efficacy as a thrombin inhibitor in vitro, also exerted no apparent impact on thrombus formation in vivo, resulting in a mean occlusion time of 71±19 minutes. The absence of an antithrombotic effect for PPACK accords with the expectation of a 2.9-minute reported clearance half-life and with the known in vivo instability of PPACK without protection of the N-terminus.

Heparin, however, has well-characterized antithrombotic effects and is a standard option as an anticoagulant for mediation of acute thrombus formation. Previous trials with the rose bengal thrombosis model yielded an occlusion time of 97±18 minutes for heparin at a dose of 0.125 mg/kg animal weight [31]. Here, occlusion occurred at 102±13 minutes (FIG. 6A).

Occlusion time more than doubled to 145±13 minutes in the mice treated with a 1 ml/kg dose of PPACK nanoemulsion (FIG. 6A). As compared to a high dose of heparin, PPACK nanoparticles outperformed (p<0.001) the established anticoagulant. Likewise, both PPACK nanoparticles (p<0.001) and heparin (p<0.05) extended time to occlusion of the carotid over PPACK treatment.

Figure 6B:
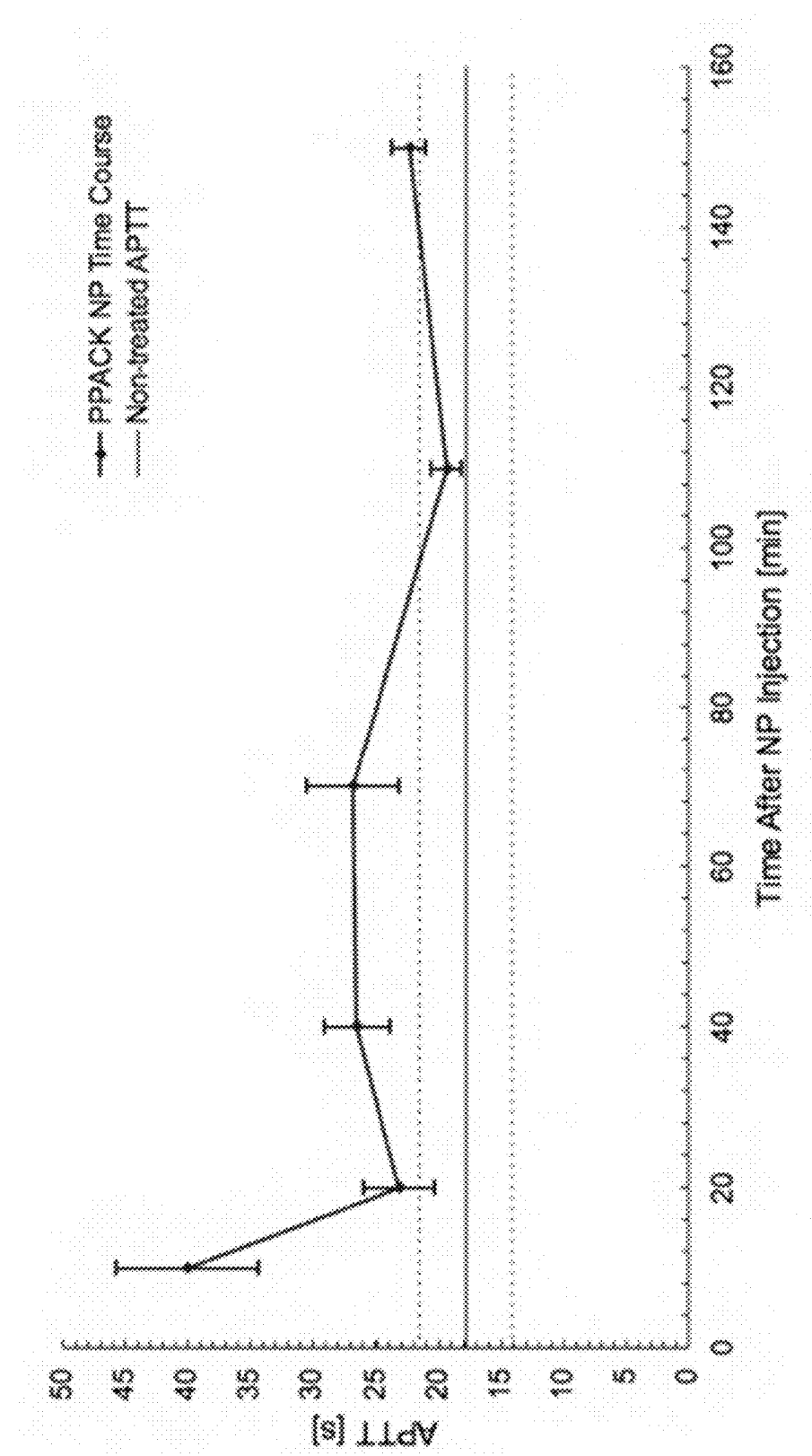
Figure 7:
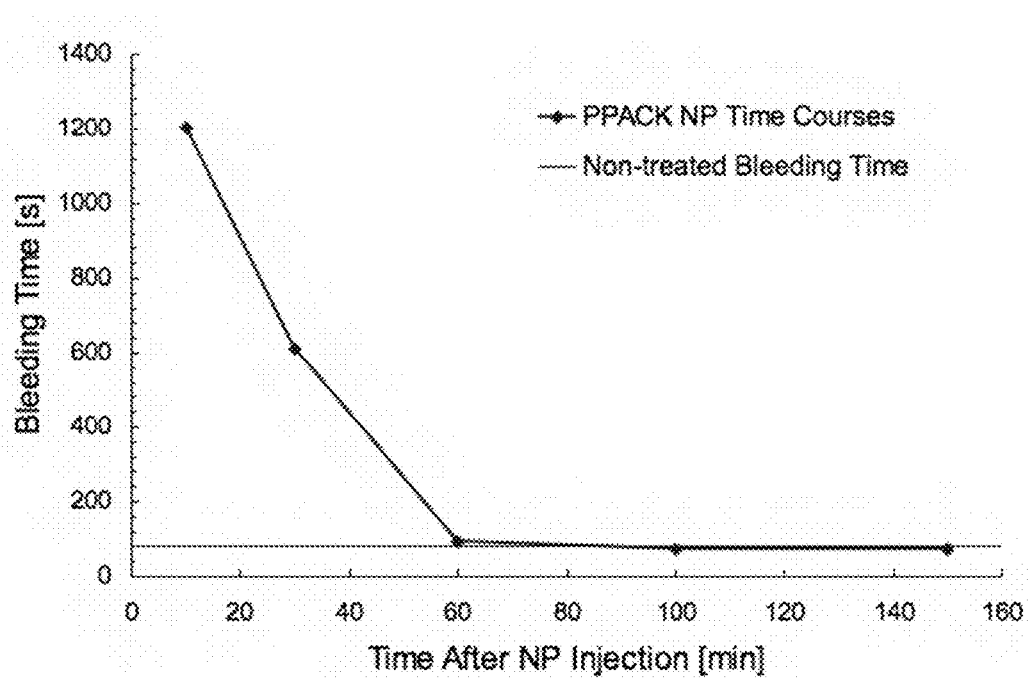
FIG. 7 depicts a graph. Bleeding times were measured via distal tail injury at selected times after tail vein bolus of PPACK nanoparticles at 1 ml/kg. All depicted data are for n=1.

Activated partial thromboplastin time (APTT) for treatment with control nanoparticles did not significantly differ from APTT for saline treatment. At 10 minutes after injection of PPACK nanoparticles, coagulation time was significantly lengthened. However, blood withdrawn at 20 minutes after injection nearly matched control APTT values. Subsequent blood draws yielded APTTs that did not significantly differ from control values (FIG. 6B), indicating fast abatement of the systemic effects of the PPACK particles despite prolonged therapeutic effect. A similar time course was evident in preliminary measurements of bleeding times in the tail after administration of PPACK nanoparticles as a tail vein bolus (FIG. 7).

Figure 8A:
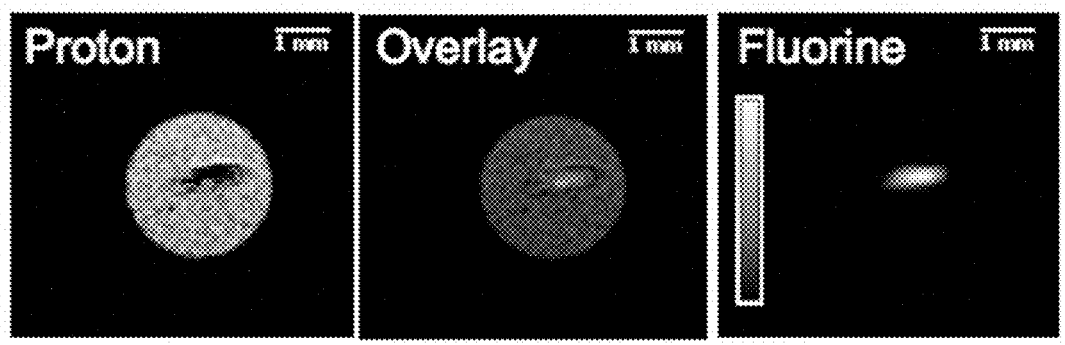
FIG. 8A-B depict an excised occluded artery from a mouse treated with PPACK nanoparticles. In mice receiving treatment with control nanoparticles (n=3) or PPACK nanoparticles (n=3), both carotid arteries were excised following induction of occlusive thrombi in the right carotid artery. $^{19}F$ MRI at 11.7 T exhibited coregistration of $^{19}F$ signal from PPACK nanoparticles with $^{1}H$ images depicting the occlusive clot in the artery (A). $^{19}F$ MRS was used to quantify retention of nanoparticles in the injured right carotid artery (RA) and the unharmed left carotid artery (LA) for the two tested nanoparticle treatments. Retained particles±standard error are represented in (B).

$^{19}$F magnetic resonance imaging and spectroscopy were used to assess Perfluoro 15-Crown-5 Ether (CE) NMR signal present in selected arteries due to retention of PFC nanoparticles. FIG. 8A depicts an excised occluded artery from a mouse treated with PPACK nanoparticles. In the left panel, a proton MRI illustrates a 0.2 mm cross-section of the artery with a dense clot in the center. A false color $^{19}$F 1 mm projection image in the right panel depicts nanoparticle content in the artery. An overlay of the two images indicated strong colocalization of the particles with the clot, implying the possibility of tracking PPACK nanoparticles as they act to interrupt clot formation.

Figure 8B:
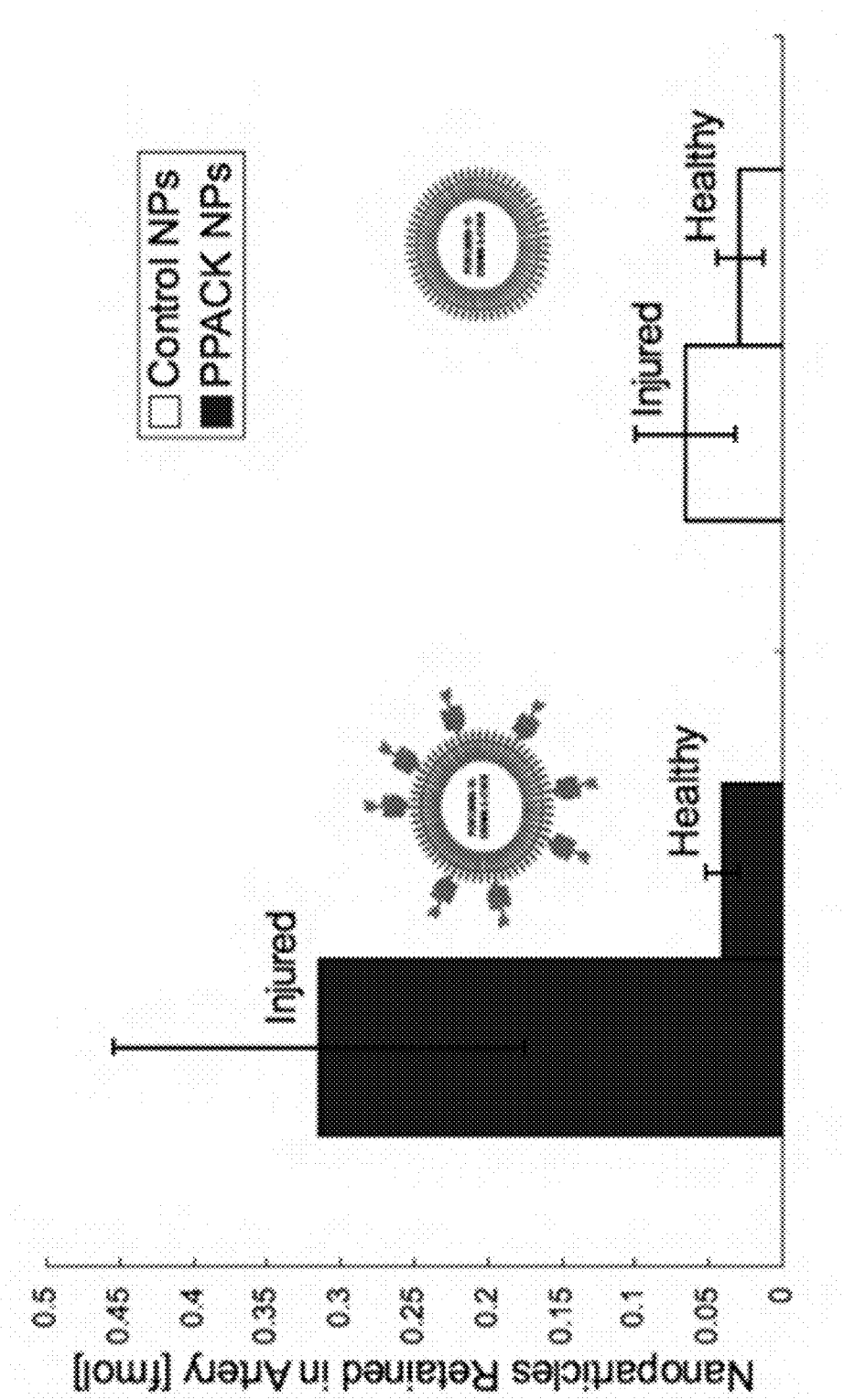

Quantitative $^{19}$F spectroscopy was employed to quantify nanoparticle incorporation into clots from six mice (FIG. 8B). In mice treated with PPACK nanoparticles, injured arteries retained 0.31±0.14 fmol and unaffected arteries retained 0.04±0.01 fmol nanoparticles. In mice treated with control nanoparticles, injured arteries retained 0.07±0.03 fmol and uninjured arteries retained 0.03±0.02 fmol.

Figure 9A:
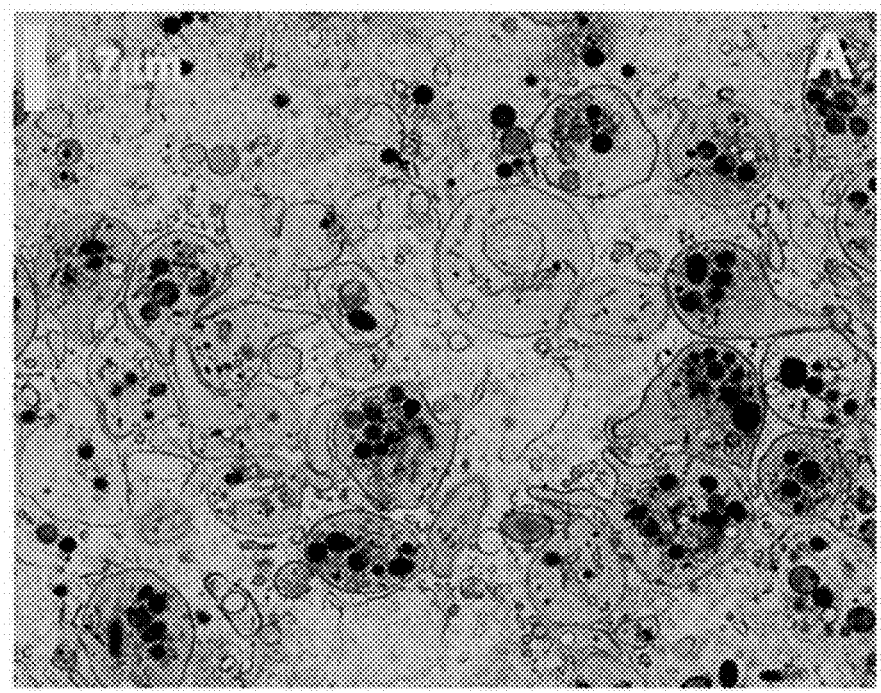
FIG. 9A-B depict photomicrographs. TEM was used to characterize microstructure of excised clots formed during PPACK nanoparticle or control nanoparticle treatment. Clots formed in the presence of PPACK-nanoparticles had loosely associated platelets with little evidence of degranulation (A). Close association, degranulation, and interdigitation of platelets was evident in clots formed in the presence of control nanoparticles (B).
Figure 9B:
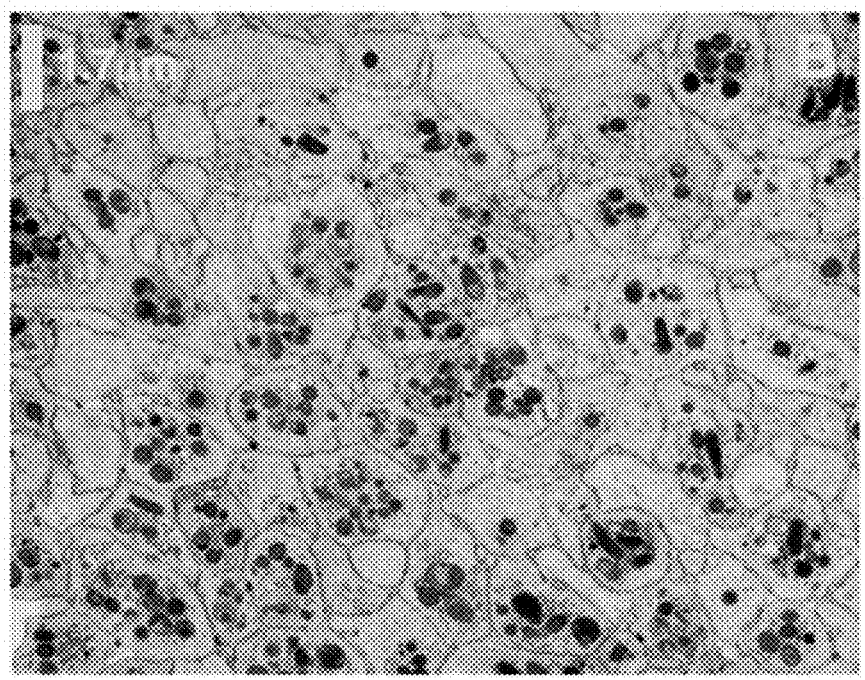

To further elucidate the mechanism by which PPACK nanoparticles prevent thrombus formation, TEM was used to examine the microstructure of fully formed thrombi. In clots formed after treatment with PPACK nanoparticles, few degranulated platelets were observed. Furthermore, platelets in such clots were loosely associated with one another, showing no signs of the dense packing evident in well-formed platelet aggregates. Instead, a fibrin gel appeared to dominate the clot microstructure (FIG. 9A). In TEM images of clots subject to control nanoparticle treatment, close association and interdigitation of platelets was evident. Similarly, degranulated platelets were abundant in these thrombi (FIG. 9B).

Figure 10A:
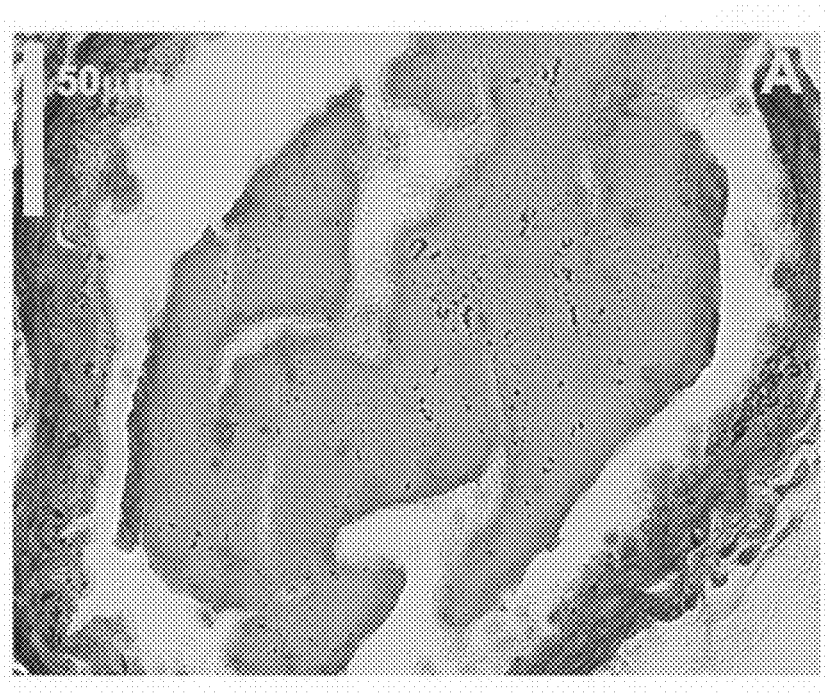
FIG. 10A-B depict photomicrographs. Carstair's staining of clots subject to treatment with PPACK nanoparticles (A) or control nanoparticles (B) helped to examine the nature of the clots formed with each treatment. Clots formed in the presence of PPACK nanoparticles exhibited sparse staining of platelets (blue in the central region) and large amounts of isolated fibrin (pink in the central region) (A). With control nanoparticle treatment, staining of platelets was more prominent (B).
Figure 10B:
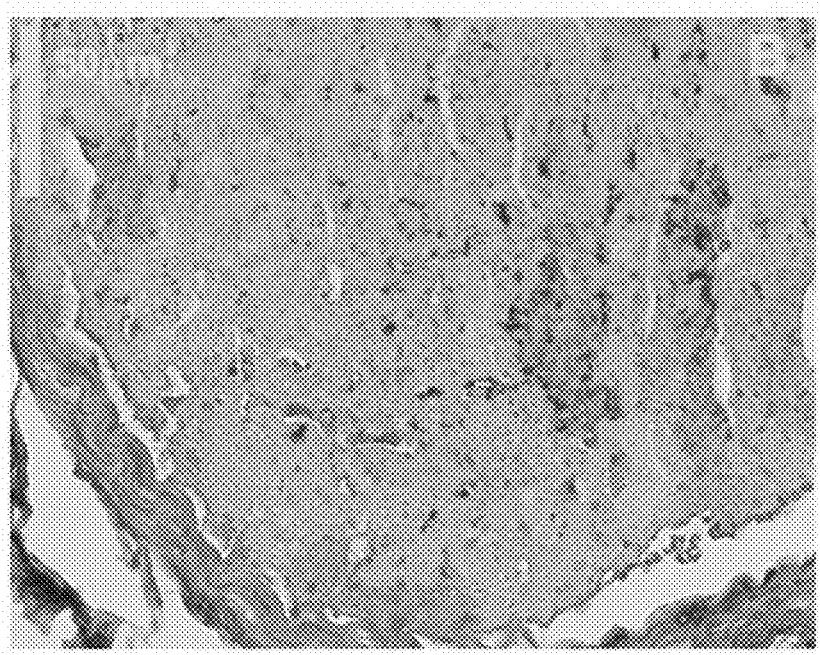
Figure 11:
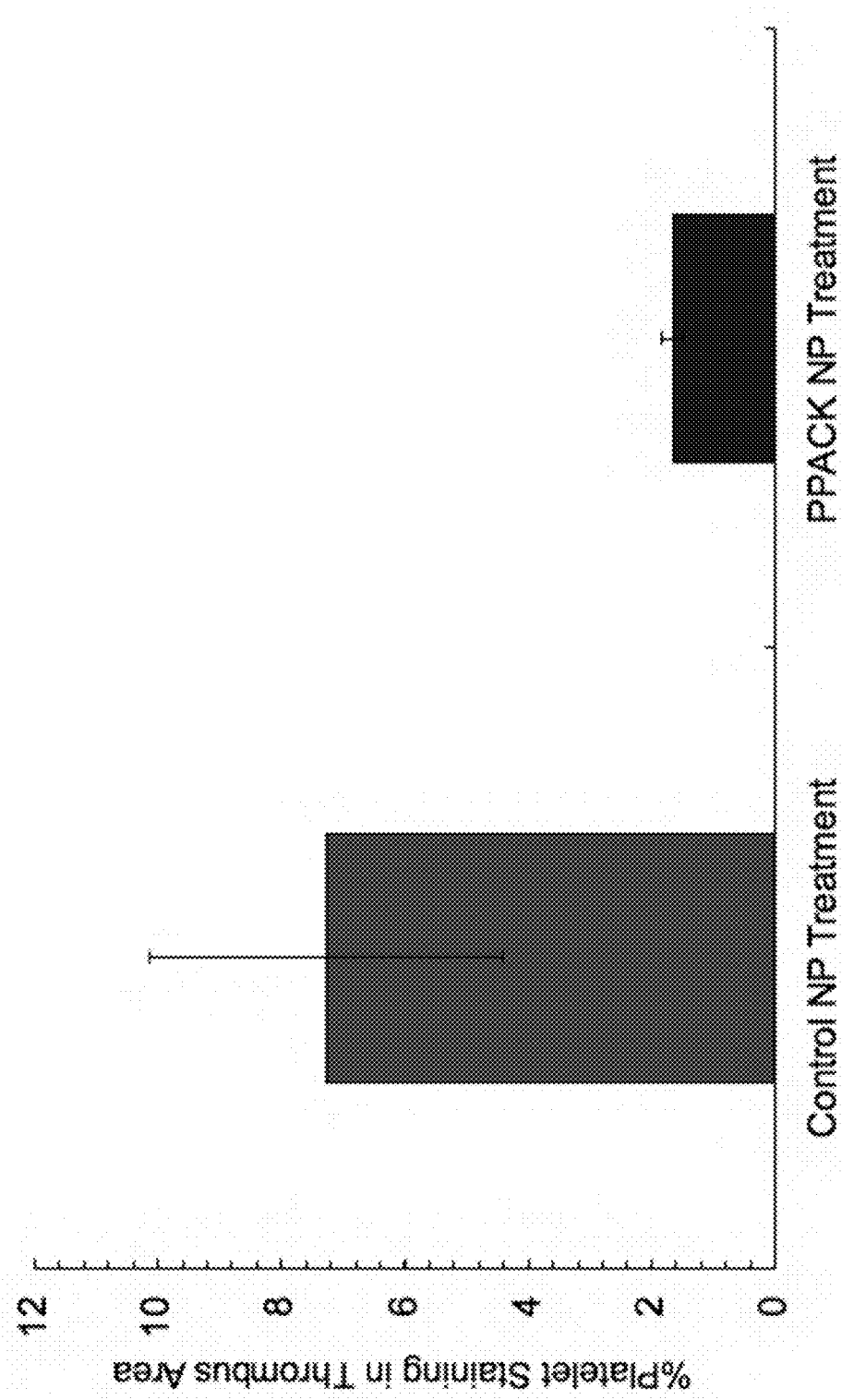
FIG. 11 depicts a plot. Area occupied by platelet staining within Carstair's stained thrombi was evaluated in NIH ImageJ. For three arteries treated with control nanoparticles, platelet staining occupied 7.28%±2.87% of thrombus area. For three arteries treated with PPACK nanoparticles, platelet staining occupied 1.66%±0.18% of thrombus area.

Carstair's staining was used to assess relative amounts of platelets and fibrin in selected clots. Staining of clots formed after PPACK nanoparticle treatment indicated a predominance of fibrin with only sparse clusters of platelets (FIG. 10). For clots formed in the presence of control nanoparticles, platelet staining was denser and interconnected (taking up 7.28% of clot area as opposed to 1.66% in PPACK-treated clots) (FIG. 11).

Discussion for Examples 1-3

The goal of the examples above was to design a therapeutically active nanoparticle with inherent targeting to proliferating thrombi. A PFC nanoparticle anticoagulant that features covalently bound PPACK as its active component was synthesized and implemented. Whereas PPACK itself is not clinically useful as an antithrombotic [2, 27], the examples demonstrate the PPACK nanoparticle to be an effective intravenous anticoagulant. The rose bengal thrombosis model was chosen for its demonstrated sensitivity to a wide range of anticoagulants. The time to arterial occlusion in this model has shown susceptibility to treatment with notable thrombin inhibitors [32]. The rose bengal model demonstrates that the PPACK nanoparticle may delay localized occlusive thrombosis while minimizing systemic effects on bleeding times.

Imaging contrast provided by the particle core indicated that the particle inherently confines to the site of thrombosis, explaining the highly targeted therapeutic effect. Given the colocalization of the particle to sites of thrombosis and the extensive previous use of PFC particles to provide magnetic resonance, ultrasound, optical and SPECT contrast [29, 33-35], PPACK nanoparticles have potential as a tool for diagnostic mapping of thrombosis. As shown previously for fibrin in clots [36, 37], $^{19}$F signatures from the PFC core may be quantified in molarity to provide a gross estimate of their local concentration, indicative of the binding at the site of thrombosis in this case.

The pharmacokinetics of functionalized PFC nanoparticles have been established in previous work exploring the use of such particles in drug delivery and imaging applications [28, 29]. Through these studies and in a long history of use in blood transfusions [28], the in vivo safety and stability of PFC emulsions has been established. Stable attachment of covalently bound targeting ligands has also been demonstrated [38-40]. Building on this work, the antithrombotic nanoparticle presents a direct thrombin inhibitor on its surface during circulation and upon retention at a site of developing thrombosis. The fundamentally different in vivo behavior of PPACK on the particle may be attributed to both prolonged circulation and sequestration at the site of thrombosis.

Analysis of thrombotic occlusions formed in the presence of PPACK particles indicates that, as part of its therapeutic impact, the antithrombotic particle impacts platelet deposition. The particle likely inhibits thrombin's ability to activate platelets via PAR cleavage [17-21]. As evaluated with Carstair's staining (FIG. 10) and with TEM (FIG. 9), the morphology of the clots formed after PPACK particle treatment is distinguished by sparse platelet distribution and reduced density of packing. Although thrombin inactivation is not the traditional route to antiplatelet therapy, antiplatelet activity is a useful effect of thrombin targeting. Thus, the apparent reduction in platelet deposition in the treatment evidences a possible broader clinical application for the particle as a combined antithrombotic and antiplatelet agent.

Anticoagulants that are mechanistically based on thrombin inhibition abound in standard clinical practice. Most notably, heparin binding dramatically accelerates the inhibition of thrombin by antithrombin and by heparin cofactor II [31]. However, deficiencies in antithrombin or heparin cofactor II are well documented [7, 41-43]. Further evidence indicates that the activity of antithrombin-heparin is significantly abated when the inhibitory complex is bound in a growing thrombus [44]. A preference for thrombin inhibition with direct, high-affinity, and specific inhibitors has evolved in recent years.

The design of specific and potent direct thrombin inhibitors has garnered attention from numerous researchers. However, problems of specificity, toxicity, and unacceptable circulating half-life have plagued many otherwise promising lead compounds [3, 45]. Amongst direct thrombin inhibitors, PPACK was used here as a reasonably cheap, small, and non-toxic [27] agent to complex with PFC nanoparticles. However, other known thrombin inhibitors could be employed. Flexible conjugation schemes abound, given that diphospholipids with large varieties of linking groups and spacers are readily available commercially. Different inhibitor concentrations could also be tested. The PFC nanoparticle thrombin inhibitor model would likely retain its noted advantages with adaptation to different inhibitory moieties.

Regardless of the drug that is conjugated to the particle, the antithrombotic nanoparticle is designed to act as a unique inhibitor in its own right. Rather than serving as a vehicle that delivers an antagonist to the thrombin target, the particle holds onto the inhibitor and acts against thrombus formation by maintaining localized thrombin-absorbing surfaces that are not disabled after locating a thrombin target.

In recent clinical trials, problems of toxicity (in the case of the reversible thrombin inhibitor Ximelagatran [45]) or ambiguous patient outcome (in the case of the P2Y12 inhibitor Ticragelor [46]) have raised questions of efficacy and labeling in otherwise promising anticoagulants used in acute coronary syndromes. There continues to be a need for new potent and highly specific antithrombotic agents with minimal toxicity for the treatment of thrombosis in acute coronary syndromes [10-12], stroke [13], venous thrombosis [11, 14], and stent placement [47, 48]. The particle developed here may be used in acute treatments, as a potent, more effective local therapy with an improved safety profile that serves as a bridge to outpatient oral therapy.

Example 4. Nanoparticles Functionalized with Bivalirudin

Figure 12A:
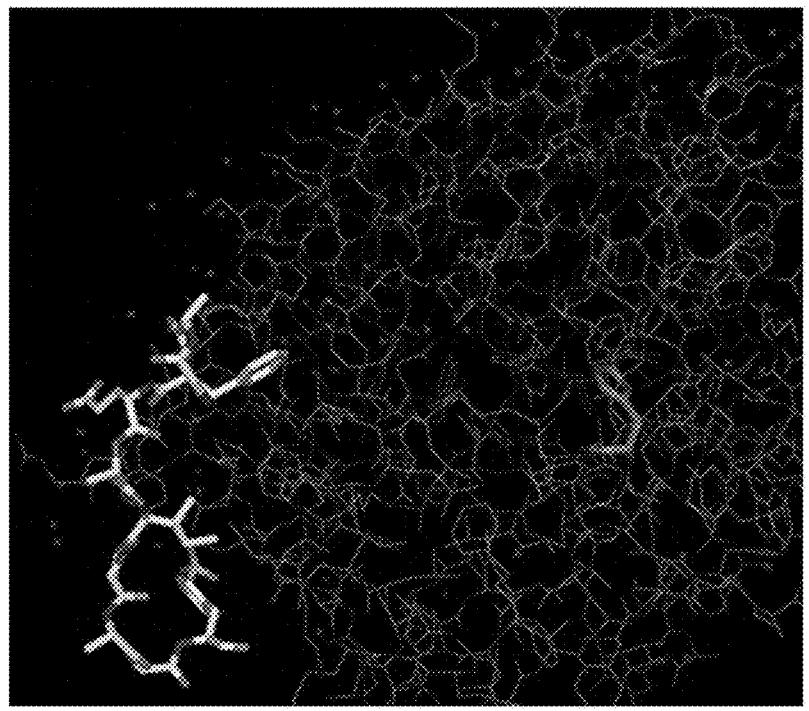
FIG. 12A-B depict molecular models of Bivalirudin inhibition sites on thrombin.
Figure 12B:
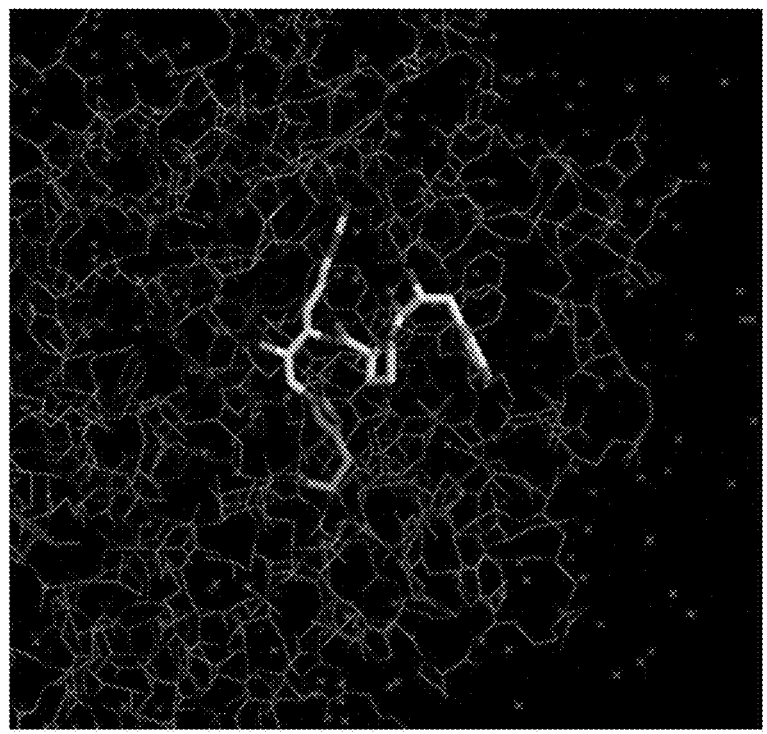

Bivalirudin (Hirulog) is a specific and reversible direct thrombin inhibitor (DTI). Bivalirudin inhibits thrombin by specifically binding both to the anion-binding exosite I (FIG. 12A) and to the active site (FIG. 12B) of circulating and clot-bound thrombin. Bivalirudin overcomes many limitations seen with indirect thrombin inhibitors, such as heparin. Bivalirudin is a short, synthetic peptide that inhibits both circulating and clot-bound thrombin, while also inhibiting thrombin-mediated platelet activation and aggregation. Bivalirudin has a quick onset of action and a short half-life. It does not bind to plasma proteins (other than thrombin) or to red blood cells. Therefore it has a predictable antithrombotic response. There is no risk for Heparin Induced Thrombocytopenia/Heparin Induced Thrombosis-Thrombocytopenia Syndrome (HIT/HITTS), it does not require a binding cofactor such as antithrombin and does not activate platelets. These characteristics make Bivalirudin an ideal alternative to heparin.

Figure 13A:
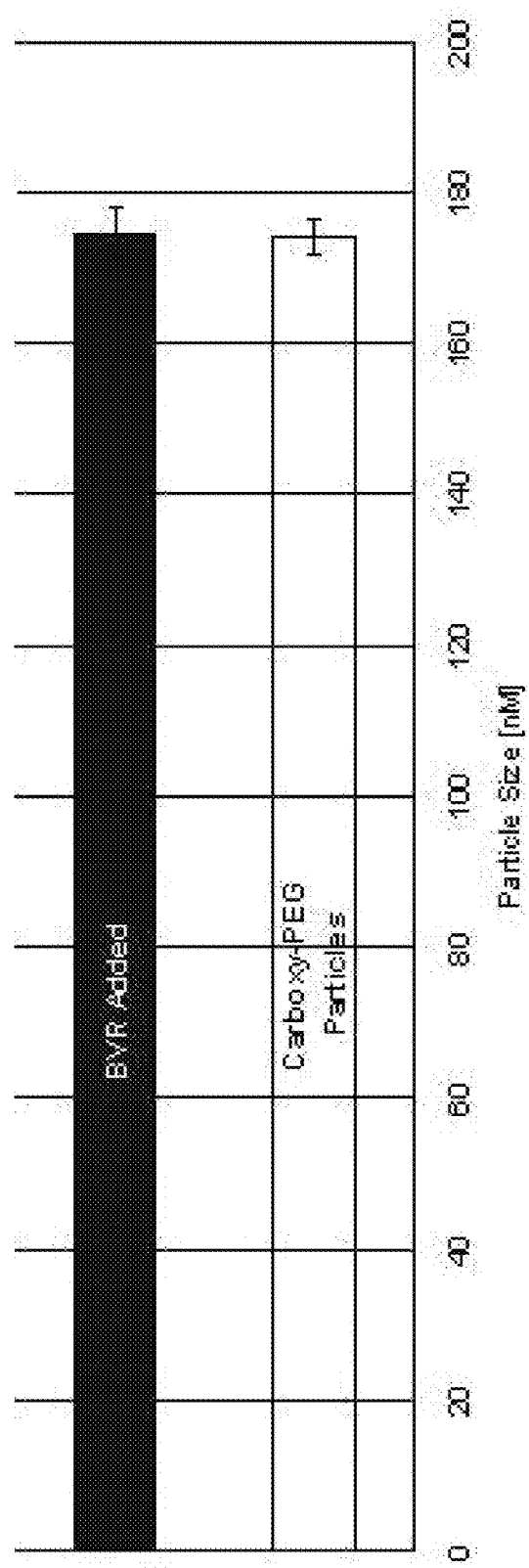
FIG. 13A-B depict two plots. Particle size was measured before and after addition of Bivalirudin to nanoparticles. The addition of Bivalirudin did not significantly change the mean hydrodynamic particle diameter (A). Corresponding to conjugation of Bivalirudin to carboxy-terminated lipids, the particle zeta potential after functionalization (B).
Figure 13B:
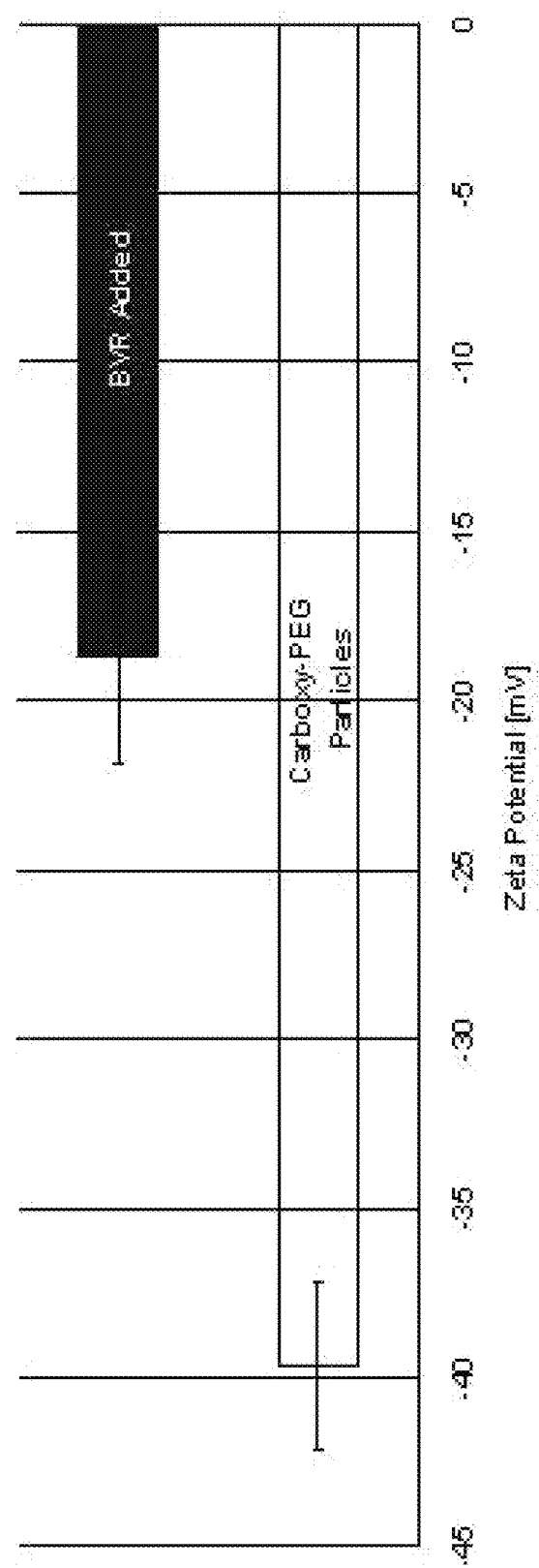

Bivalirudin was conjugated to Carboxy-PEG functionalized nanoparticles at the N-terminus using procedure described in the Materials and Methods for Examples 1-3 above. After conjugation of Bivalirudin, nanoparticles were examined to verify stability, and found to have analogous coupling and stability characteristics (FIGS. 13A and B) to the PPACK particles described in Examples 1-3.

Figure 14:
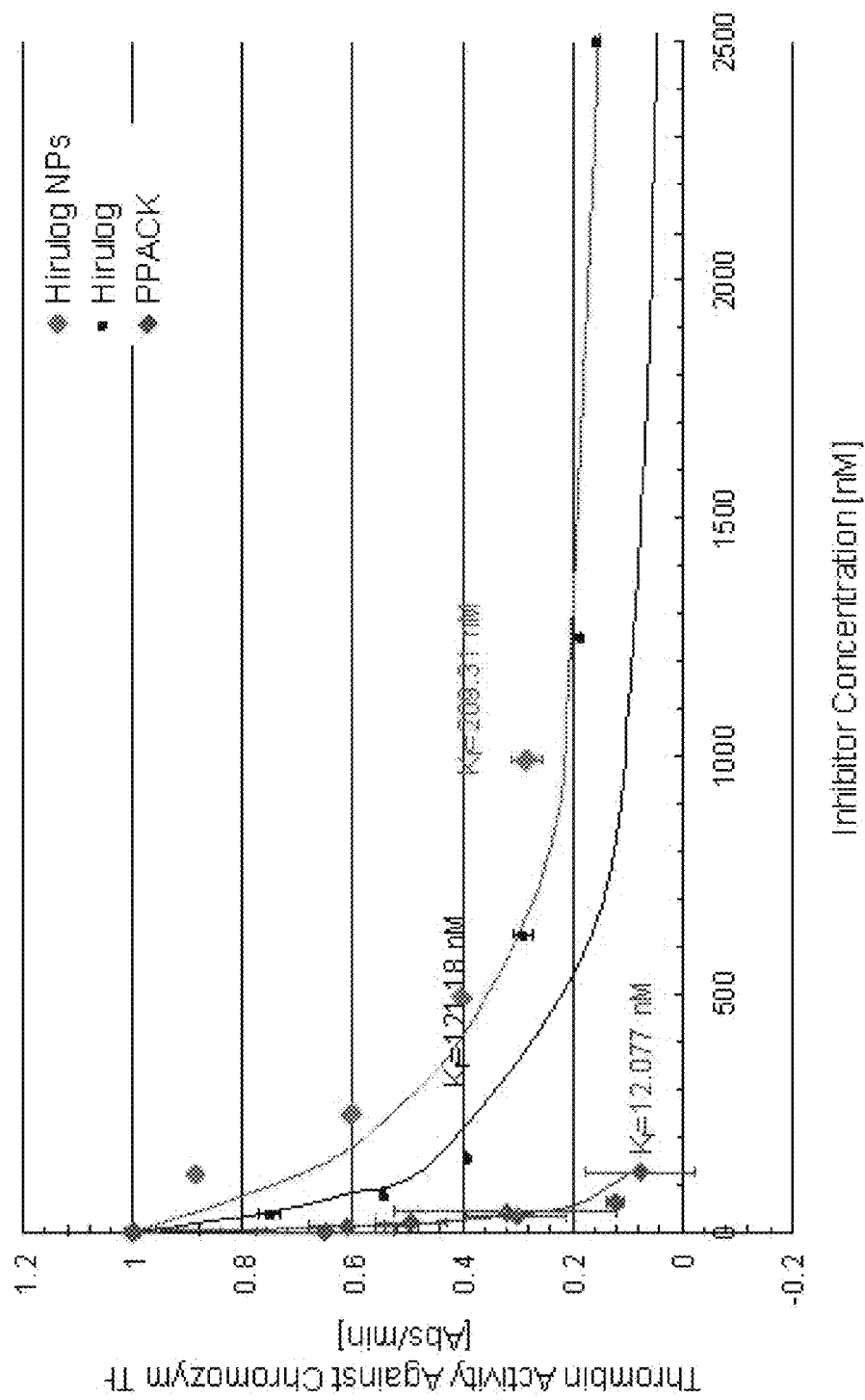
FIG. 14 depicts a graph illustrating the activity of the antithrombotic nanoparticle.

Bivalirudin and Bivalirudin nanoparticle inhibition of thrombin was evaluated and compared to inhibition of thrombin by PPACK (FIG. 14). The results show that Bivalirudin is less active, but more specific than PPACK. In addition, Bivalirudin activity, as with PPACK, was not significantly diminished on the particles.

Figure 15:
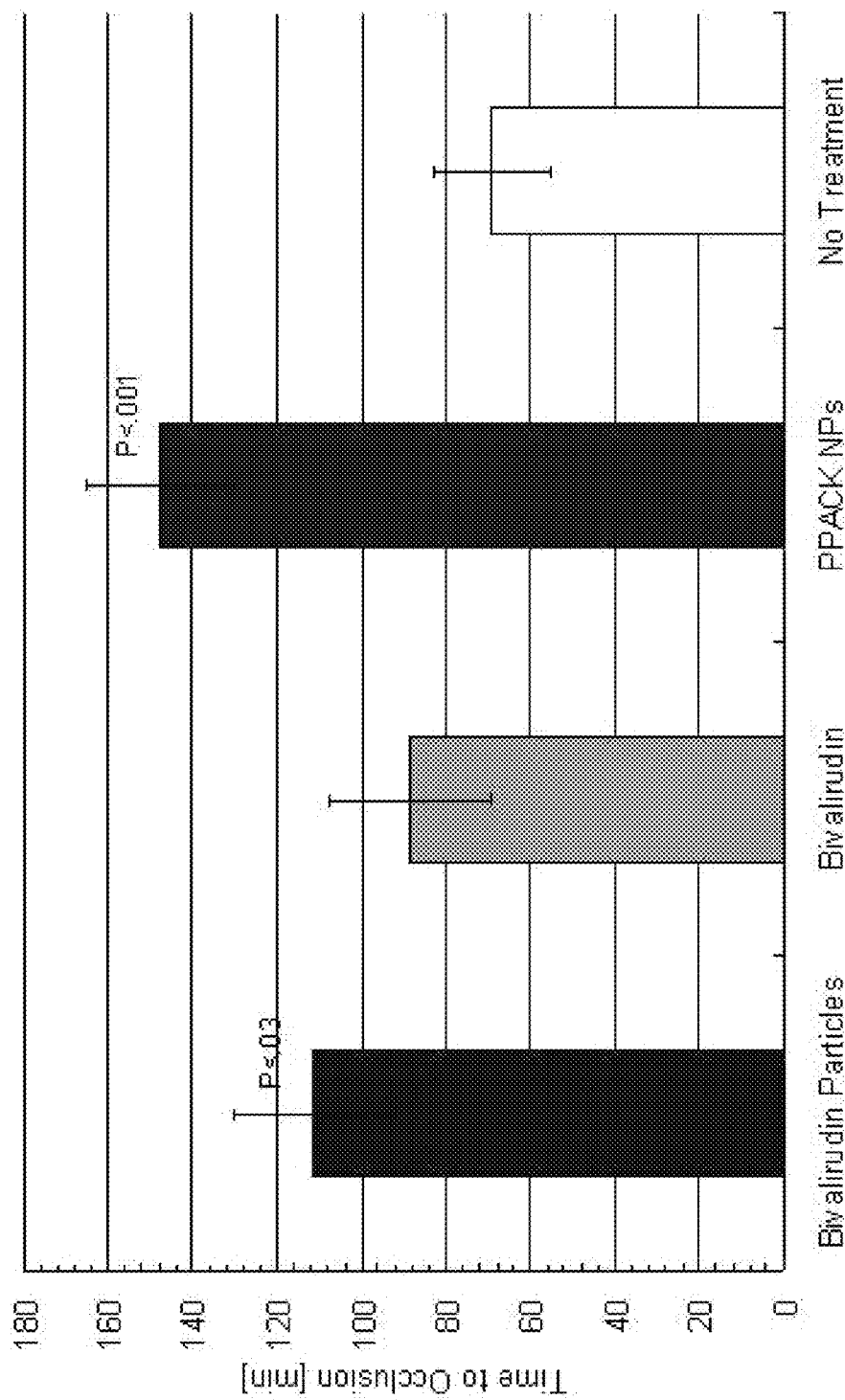
FIG. 15 depicts a graph illustrating mean±standard deviation occlusion time for each tested treatment condition in photochemical thrombotic injury experiments.

The in vivo effect of Bivalirudin nanoparticles was measured as described in Examples 1-3 above, and compared to PPACK nanoparticles (FIG. 15). At the administered dose, Bivalirudin did not significantly extend occlusion time, but Bivalirudin nanoparticles did. PPACK nanoparticles on the other hand, outperformed both Bivalirudin treatments when using an identical dose. Even though Bivalirudin has been shown to provide more effective action against fibrin-bound thrombin (activity against exosite I), Bivalirudin particles may be more likely to release from the target due to cleavage of the inhibitor by thrombin.

Figure 16:
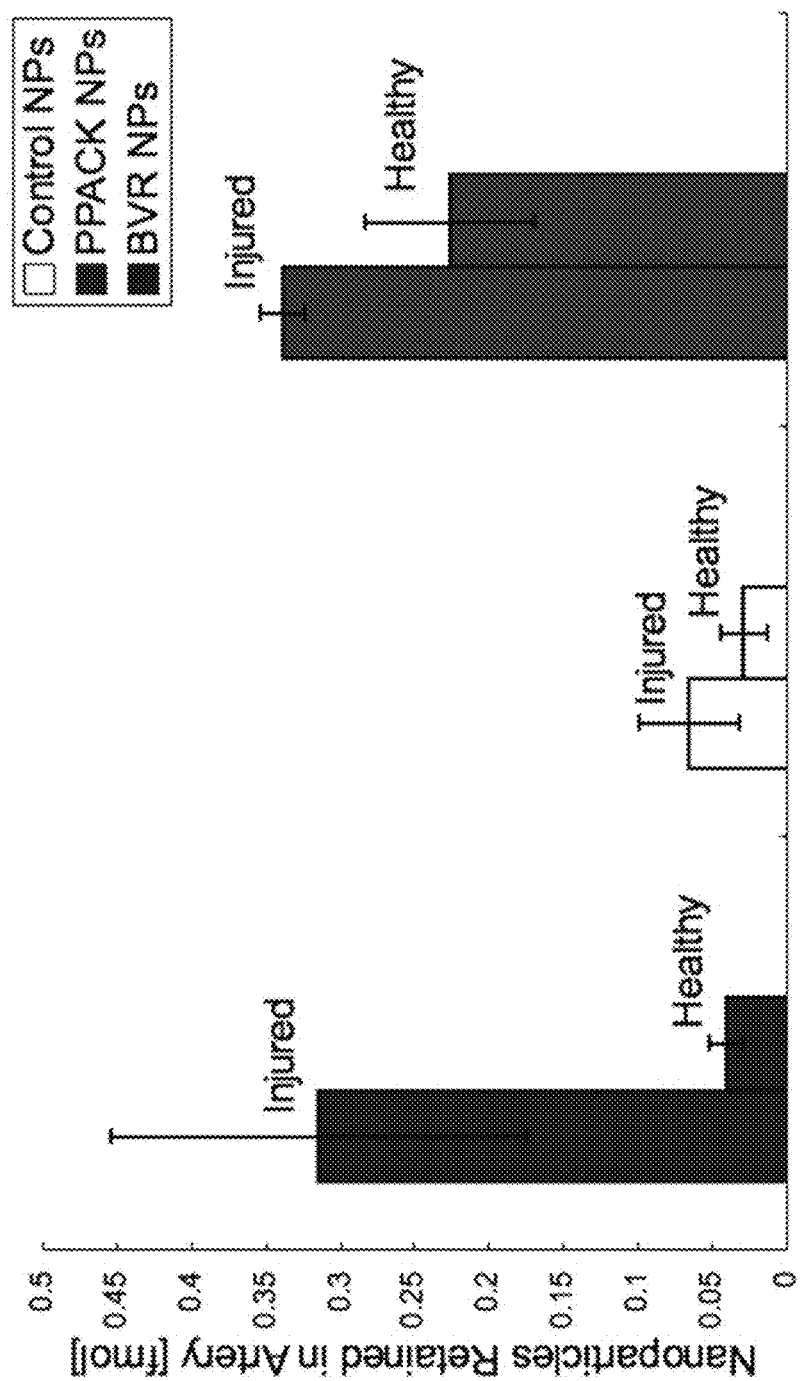
FIG. 16 depicts a graph illustrating the amount of nanoparticles retained in an artery. $^{19}F$ MRS was used to quantify retention of nanoparticles in the injured right carotid artery (RA) and the unharmed left carotid artery (LA) for the three tested nanoparticle treatments. Retained particles±standard error is represented in the graph.

$^{19}$F magnetic resonance imaging and spectroscopy were used to assess Perfluoro 15-Crown-5 Ether (CE) NMR signal present in selected arteries due to retention of PFC nanoparticles (FIG. 16).

Figure 17:
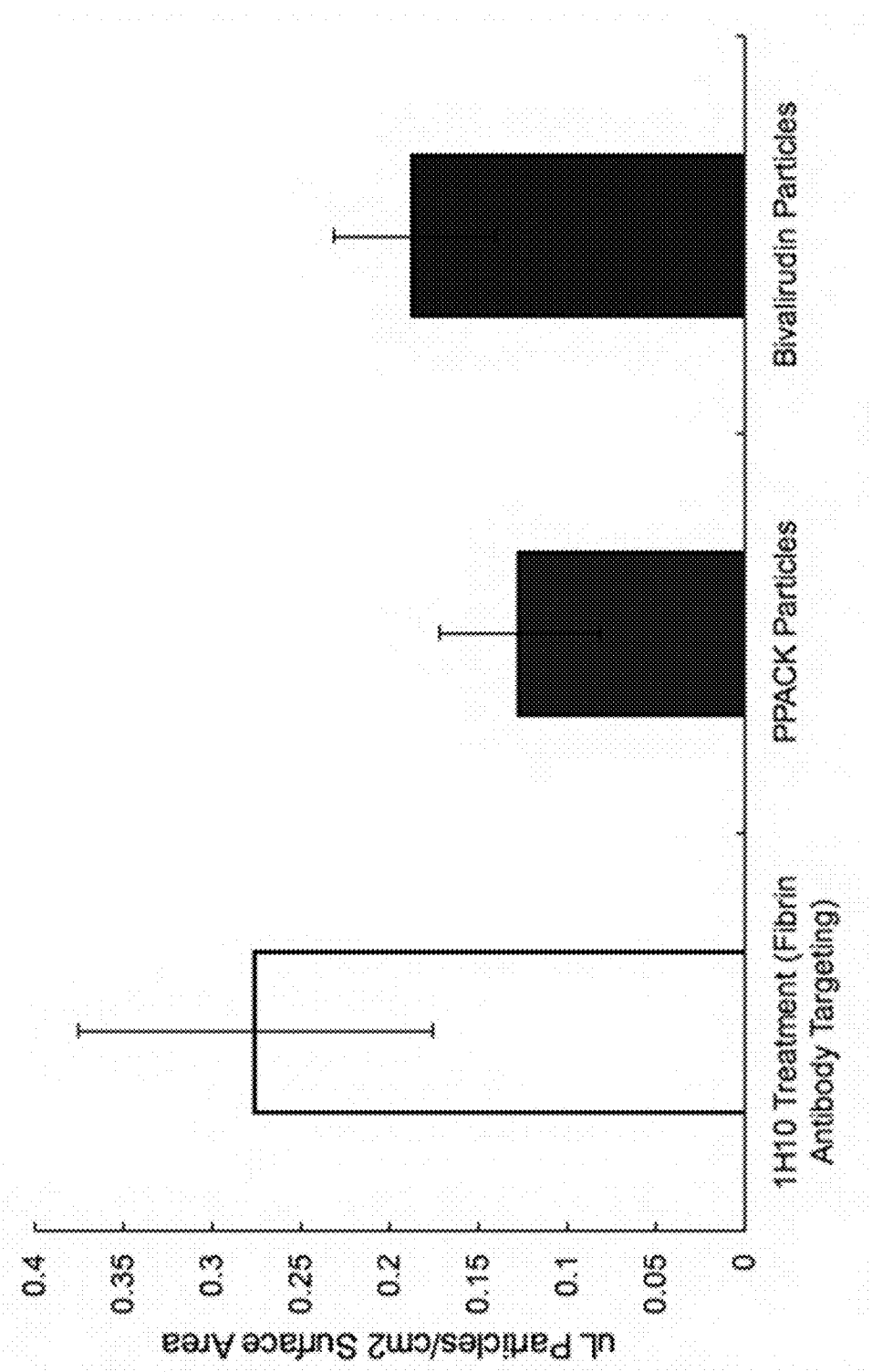
FIG. 17 depicts a graph illustrating the amount of nanoparticles per surface area of a clot. Human fibrin clots were formed via activation of citrated plasma with thrombin and 500 mM $CaCl_2$ as described previously (Morawski A M et al (2004) 52: 1255-1262.). For thrombin-targeted particles, clots were incubated with 1:15 dilution of emulsion at 37 degrees for two hours on a rotating platform shaker prior to rinsing and quantitative $^{19}F$ spectroscopy. For fibrin targeting, clots were incubated with 125 ug of biotinylated 1H10 antibody at 4 degrees for 12 hours prior to incubation with avidin-functionalized nanoparticles at 37 degrees as with thrombin targeting.
Figure 18A:
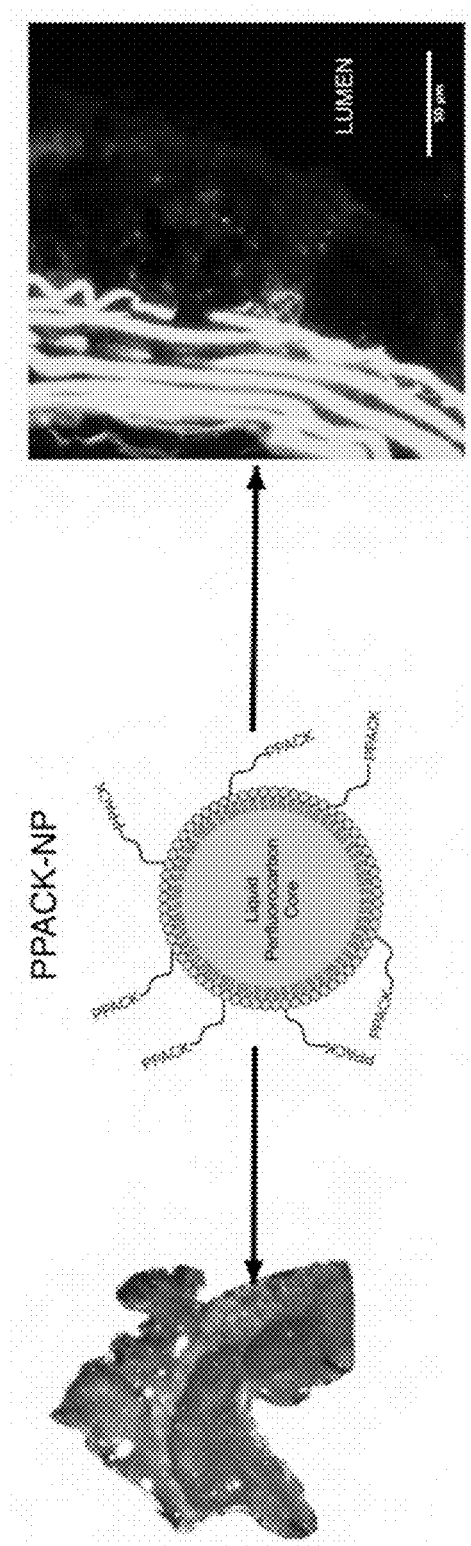
FIG. 18A-D illustrate various aspects of Example 5. (A) Schematic of PPACK-NP (center panel). Nanoparticles consist of a perfluorocarbon core surrounded by a stabilizing phospholipid monolayer to which PPACK is covalently conjugated. In this work, PPACK-NP act on both the exterior and interior regions of plaques in inhibiting the inflammatory effects of thrombin. Fluorescent microscopy image (right panel) of mouse atherosclerotic plaque at 3 months of cholesterol feeding demonstrates intraplaque accumulation of PPACK-NP (red). Sudan IV staining of the aortic arch of cholesterol fed ApoE mice demonstrates ample plaque deposition serving as a target for PPACK-NP therapy (left panel) (B) Feeding and dosing schedule for ApoE-null mice. During the 4-week treatment period, mice received i.v. treatments three times per week. (C) Schematic representation of $^{19}$F-MRS-based detection of endothelial barrier disruption. Non-targeted CENP are administered and circulated for 2 hours. Aortas are removed and $^{19}$F signal is measured. High $^{19}$F signal corresponds to increased endothelial barrier disruption and increased nanoparticle accumulation, whereas low $^{19}$F signal corresponds to decreased endothelial barrier disruption and diminished nanoparticle accumulation. (D) Representative kinetics of photochemically-induced thrombus formation in ApoE-null mice treated with either saline, control NP or PPACK-NP
Figure 18B:
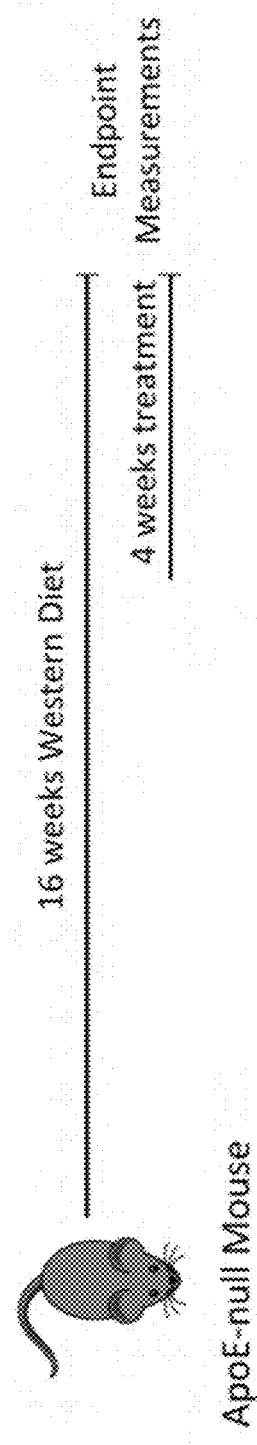
Figure 18C:
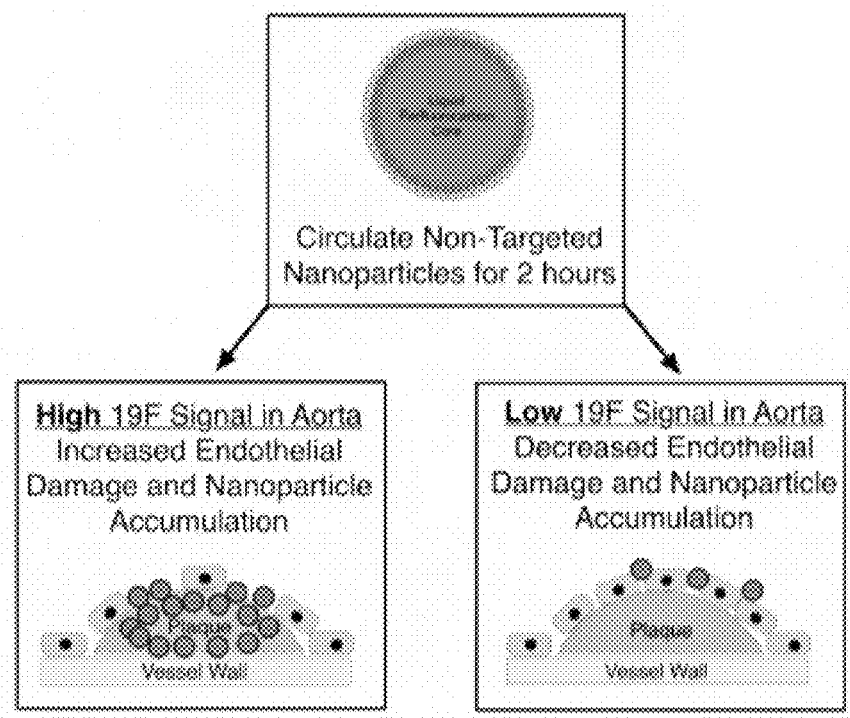
Figure 18D:
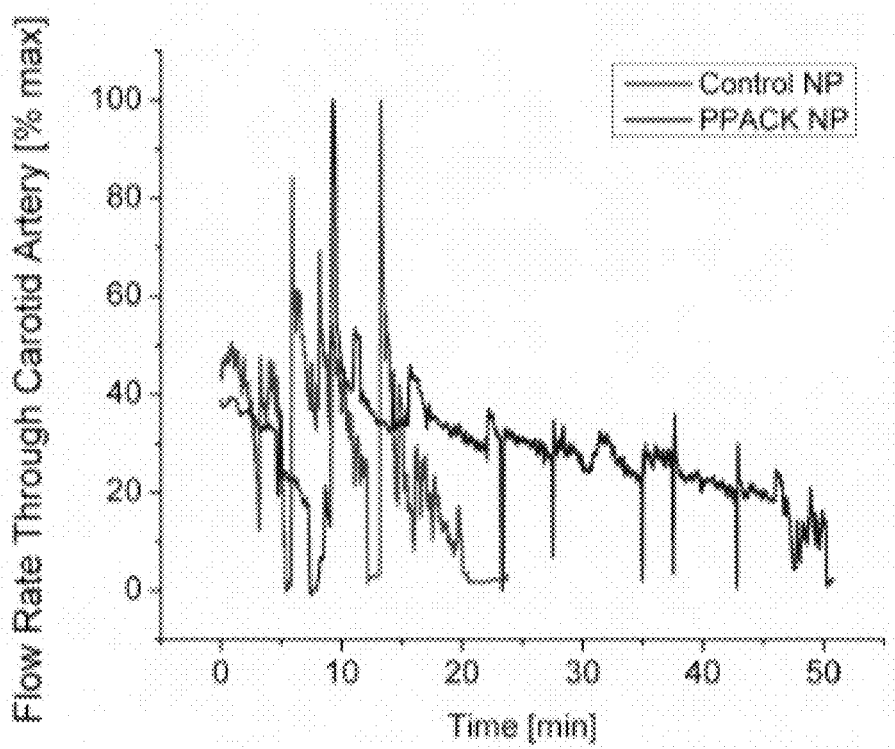

Human fibrin clots were formed via activation of citrated plasma with thrombin and 500 mM $CaCl_2$ as described previously (Morawski A M et al (2004) 52: 1255-1262.). For thrombin-targeted particles, clots were incubated with 1:15 dilution of emulsion at 37 degrees for two hours on a rotating platform shaker prior to rinsing and quantitative $^{19}$F spectroscopy. For fibrin targeting, clots were incubated with 125 ug of biotinylated 1H10 antibody at 4 degrees for 12 hours prior to incubation with avidin-functionalized nanoparticles at 37 degrees as with thrombin targeting (FIG. 17).

REFERENCES

1. Davies M J (1992) Anatomic features in victims of sudden coronary death. Coronary artery pathology. Circulation 85: 119-124.
2. Kaiser B, Hauptmann J (1992) Pharmacology of Synthetic Thrombin inhibitors of the tripeptide type. Cardiovascular Drug Reviews 10: 71-87.
3. Srivastava S, Goswami L N, Dikshit D K (2005) Progress in the design of low molecular weight thrombin inhibitors. Medicinal Research Reviews 25: 66-92.
4. Di Cera E (2008) Thrombin. Molecular Aspects of Medicine 29: 203-254.
5. Furie B, Furie B C (2008) Mechanisms of thrombus formation. The New England Journal of Medicine 359: 938-949.
6. Tait R C, Maclean P C (2007) Hereditary and acquired antithrombin deficiency epidemiology, pathogenesis and treatment options. Drugs 67: 1429.
7. Tran T H, Marbet G A, Duckert F (1985) Association of hereditary heparin cofactor II deficiency with thrombosis. Lancet 2; 413-414.
8. Ansell J, et al. (2004) The pharmacology and management of the vitamin K antagonists. Chest 126: 204S-233S.
9. Schwartz R S, et al. (2009) Microemboli and microvascular obstruction in acute coronary thrombosis and sudden coronary death: relation to epicardial plaque histopathology. Journal of the American College of Cardiology 54(23): 2167-2173.
10. Lee L V (2008) Anticoagulants in coronary artery disease. Clinical Cardiology 26: 615-628.
11. Turpie A G (2008) The top four advances in antithrombotic care in the last year. Thrombosis Research 123: S2-S6.
12. Fareed J, et al. (2008) Changing trends in anti-coagulant therapies. Are heparins and oral anti-coagulants challenged? International Journal of Angiology 27: 176-192.
13. Bousser M G (2009) Antithrombotic agents in the prevention of ischemic stroke. Cerebrovascular Diseases 27: 12-19.
14. Gross P, Weitz J I (2009) New antithrombotic drugs. Clinical Pharmacology and Therapeutics 86: 139-146.
15. Bode W, et al. (1989) The refined 1.9 Å crystal structure of human a-thrombin: interaction with D-Phe-Pro-Arg chloromethylketone and significance of the Tyr-Pro-Pro-Trp insertion segment. The EMBO Journal 8: 3467-3475.
16. Bode W, Turk D, Karshikov A (1992) The refined 1.9-Å crystal structure of D-Phe-Pro-Arg chloromethylketone-inhibited human alpha-thrombin: Structure analysis, overall structure, electrostatic properties, detailed active-site geometry, and structure-function relationships. Protein Science 1: 426-471.
17. Ivey M E, Little P J (2008) Thrombin regulates vascular smooth muscle cell proteoglycan synthesis via PAR-1 and multiple downstream signaling pathways. Thrombosis Research 123: 288-297.
18. Hirano K (2007) The roles of proteinase-activated receptors in the vascular physiology and pathophysiology. Arteriosclerosis, Thrombosis, and Vascular Biology 27: 27-36.
19. Coughlin S R (2000) Thrombin signaling and protease-activated receptors. Nature 407: 258-264.
20. Bretschneider E, et al. (2001) Evidence for functionally active protease-activated receptor-4 (PAR-4) in human vascular smooth muscle cells. British Journal of Pharmacology 132: 1441-1446.
21. Bretschneider E, et al. (2003) Evidence for functionally active protease-activated receptor-3 (PAR-3) in human vascular smooth muscle cells. Journal of Thrombosis and Haemostasis 90: 704-709.
22. Davie E W, Kulman J D (2006) Semin Thromb Hemostasis 32(Suppl 1):3-15.
23. Ghigliotti G, Waissbluth A R, Speidel C, Abendschein D R, Eisenberg P R (1998) Prolonged activation of prothrombin on the vascular wall after arterial injury. Arterioscler Thromb Vasc Biol 18:250-257.
24. Duguid J B (1946) Thrombosis as a factor in the pathogenesis of coronary atheroscle-rosis. J Pathol Bacterial 58:207-212.
25. Duguid J B (1948) Thrombosis as a factor in the pathogenesis of aortic atherosclerosis. J Pathol Bacteriol 60:57-61.
26. Kettner C, Shaw E (1979) D-Phe-Pro-ArgCH2Cl-A selective affinity label for thrombin. Thrombosis Research 14: 969-973.
27. Collen D, Matsuo O, Stassen J M, Kettner C, Shaw E (1982) In vivo studies of a synthetic inhibitor of thrombin. Journal of Laboratory and Clinical Medicine 99: 76-83.
28. Flaim S F. Pharmacokinetics and side effects of perfluorocarbon-based blood substitutes (1994) Artificial Cells, Blood Substitutes, and Immobilization Biotechnology 22: 1043-1054.
29. Hu G, et al. (2007) Imaging of vx-2 rabbit tumors with αvβ3-integrin-targeted 111In nanoparticles. International Journal of Cancer 120: 1951-1957.
30. Peters D, et al. (2009) Targeting atherosclerosis by using modular, multifunctional micelles. Proceedings of the National Academy of Sciences 106: 9815-9819.
31. Vicente C P, He L, Pavao M S G, Tollefsen D M (2004) Antithrombotic activity of dermatan sulfate in heparin cofactor II-deficient mice. Blood 104: 3965-3970.
32. Westrick R J, Winn M E, Eitzman D T (2007) Murine Models of Vascular Thrombosis. Arteriosclerosis, Thrombosis, and Vascular Biology 27: 2079-2093.
33. Winter P M, Caruthers S D, Wickline S A, Lanza G M (2006) Molecular imaging by MRI. Current Cardiology Reports 8: 65-69.
34. Partlow K C, et al. (2007) $^{19}$F magnetic resonance imaging for stem/progenitor cell tracking with multiple unique perfluorocarbon nanobeacons. The FASEB Journal 21: 1647-1654.
35. Marsh J N, et al. (2007) Molecular imaging with targeted perfluorocarbon nanoparticles: quantification of the concentration dependence of contrast enhancement for binding to sparse cellular epitopes. Ultrasound in Medicine and Biology 33: 950-958.
36. Flacke S, et al. (2001) Novel MRI contrast agent for molecular imaging of fibrin: Implications for detecting vulnerable plaques. Circulation 104: 1280-1285.
37. Morawski A M, et al. (2004) Quantitative "magnetic resonance immunohistochemistry" with ligand-targeted F-19 nanoparticles. Magnetic Resonance in Medicine 52: 1255-1262.
38. Lanza G M, et al. (2000) Molecular Imaging of Stretch-Induced Tissue Factor Expression in Carotid Arteries with Intravascular Ultrasound. Investigative Radiology 35(4): 227-234.
39. Winter P M, et al. (2003) Molecular Imaging of Angiogenesis in Nascent Vx-2 Rabbit Tumors Using a Novel $\alpha_v\beta_3$ targeted Nanoparticle and 1.5 Tesla Magnetic Resonance Imaging. Cancer Research 63: 5838-5843.
40. Winter P M, et al. (2003) Molecular Imaging of Angiogenesis in Early-Stage Atherosclerosis with $\alpha_v\beta_3$ Integrin-Targeted Nanoparticles. Circulation 108: 2270-2274.
41. Sie P, Dupouy D, Pichon J, Boneu B (1985) Constitutional heparin cofactor II deficiency associated with recurrent thrombosis. Lancet 2: 414-416.
42. Andersson T R, Larsen M L, Handeland G F, Abildgaard U. Heparin cofactor II activity in plasma: application of an automated assay method to the study of a normal adult population (1986) Scandinavian Journal of Haematology 36: 96-103.
43. Bertina R M, van der Linden I K, Muller H P, Brommer E J P (1987) Hereditary heparin cofactor II deficiency and the risk of development of thrombosis. Journal of Thrombosis and Haemostasis 57: 196-200.
44. Weitz J L, Hudoba M, Massel D, Maraganore J, Hirsh J (1990) Clot-bound thrombin is protected from inhibition by heparin-anti-thrombin III but is susceptible to inactivation by anti-thrombin III independent inhibitors. Journal of Clinical Investigation 86: 962-968.
45. Hirsh J, O'Donnell M, Eikelboom J W (2007) Beyond unfractionated heparin and warfarin. Circulation 116: 552-560.
46. Wallentin, L, et al. (2009) Ticagrelor versus Clopidogrel in Patients with Acute Coronary Syndromes. The New England Journal of Medicine 361: 1045-1057.
47. Kukreja N, Onuma Y, Daemen J, Serruys P W (2008) The future of drug-eluting stents. Pharmacological Research 57: 171-180.
48. May A E, Geisler T, Gawaz M (2008) Individualized antithrombotic therapy in high risk patients after coronary stenting. A double-edged sword between thrombosis and bleeding. Journal of Thrombosis and Haemostasis 99: 487-493.

Example 5

This example illustrates a principal mechanistic role for thrombin in vascular inflammation and atherosclerosis progression that depends in part on its deleterious consequences for vascular barrier function. This study also confirms the anti-thrombin nanoparticles of this disclosure attenuate vascular inflammatory signaling molecules, as measured by PAR-1 responses, tissue factor responses, NFkB responses, macrophage responses, endothelial adhesion marker responses. These, and other measures of vascular inflammation, are known in the art. See, for example, Palekar et al., *Arterioscler Thromb Vasc Biol.*, 2016, 36(3): 446-55, which is hereby incorporated by reference in its entirety Anti-Thrombin Nanoparticles Reduce Vascular Procoagulant Activity In Vivo.

Figure 19A:
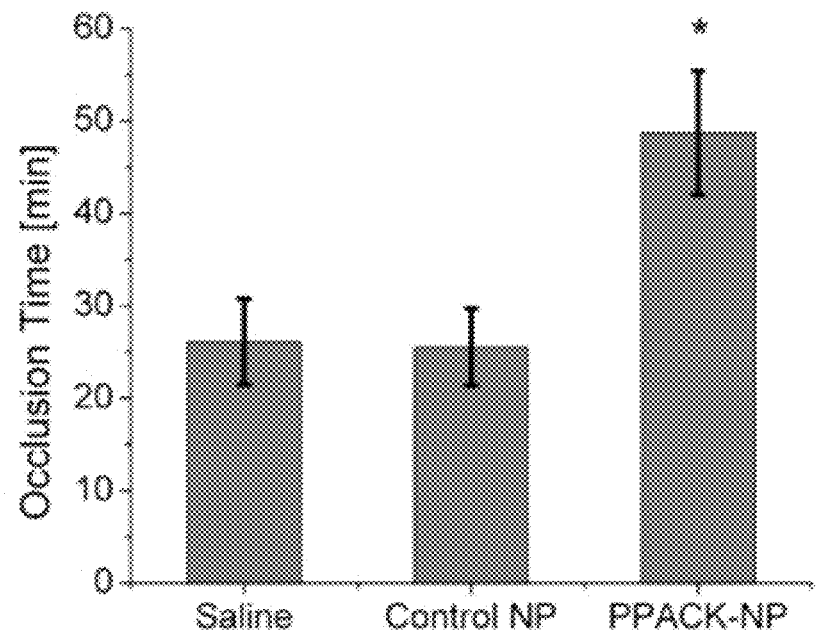
FIG. 19A-C depict graphs showing some effects of PPACK-NP treatment. (A) PPACK-NP treatment (rightmost bar) significantly increases time to occlusion of the carotid artery by 46% over saline (p=0.005) and control NP (p=0.004) treatments. (B) Plaque permeability is reduced with PPACK-NP treatment by 33% compared to saline (p=0.023) and control NP treatments (p=0.014). (C) Sudan IV staining of the aortic arch of saline and PPACK-NP treated mice demonstrates a 22.5% decrease in gross plaque deposition with PPACK-NP treatment vs. saline treatment (p=0.03) as quantified with ImageJ.

To characterize the effects of PPACK-NP on reducing procoagulant activity, groups of ApoE-null mice were fed a Western diet for 3 months followed by continuation of the diet with treatment (saline, control NP, and PPACK-NP) for 1 additional month. At the conclusion of the treatment/feeding period, mice were subjected to a previously validated[11,18,19] model for measuring thrombotic risk using photochemical injury of the carotid artery that yields a quantitative metric of coagulant activity (vessel occlusion time) with good dynamic range and monotonic responsiveness to therapeutic agents that affect clotting. Prior to performing the vessel injury, mice were maintained on their diets for 2-3 additional days without further treatment to allow washout of any residual anti-thrombin nanoparticles. After 1 month of PPACK-NP treatment, carotid occlusion times increased significantly over control groups (FIG. 19A), with occlusion times reaching 48.71±6.7 min (N=7) compared to saline treatment (26.11±4.63 min, N=9, p=0.005) and control NP treatment (25.55±4.17 min, N=9, p=0.004). We note that the occlusion times in the 1-month PPACK-NP treated group approximated those of previously reported fat-fed ApoE null mice after 2 months off diet, indicating that the PPACK NP therapy may more rapidly attenuate vessel procoagulant activity than does dietary management in this model, despite maintenance of the high fat diet in the PPACK NP treated group.[11]

Anti-Thrombin Nanoparticles Restore Vascular Barrier Integrity In Vivo.

Figure 19B:
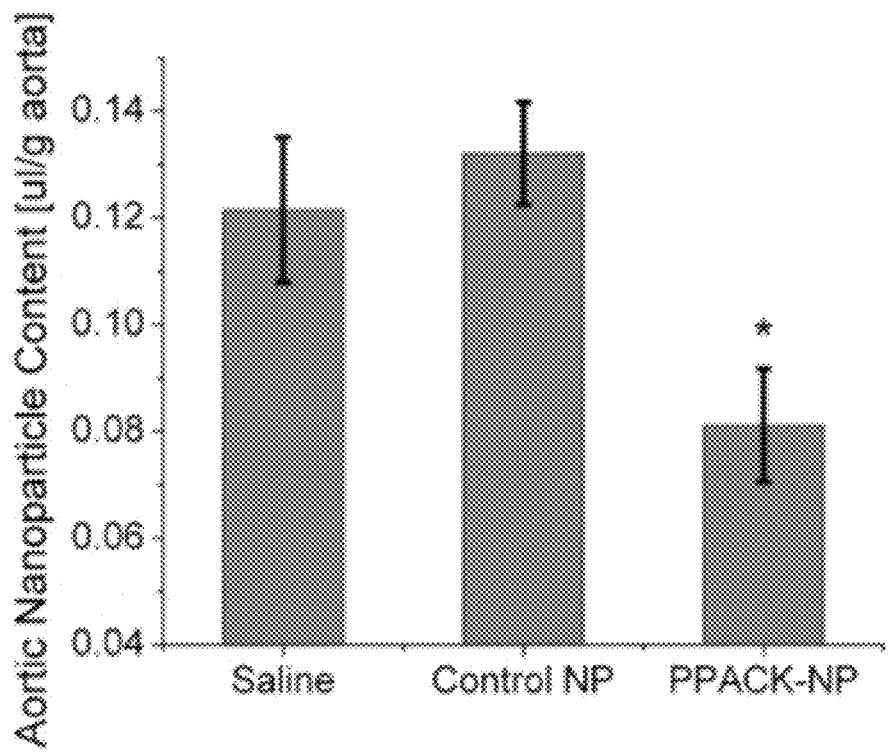
Figure 25:
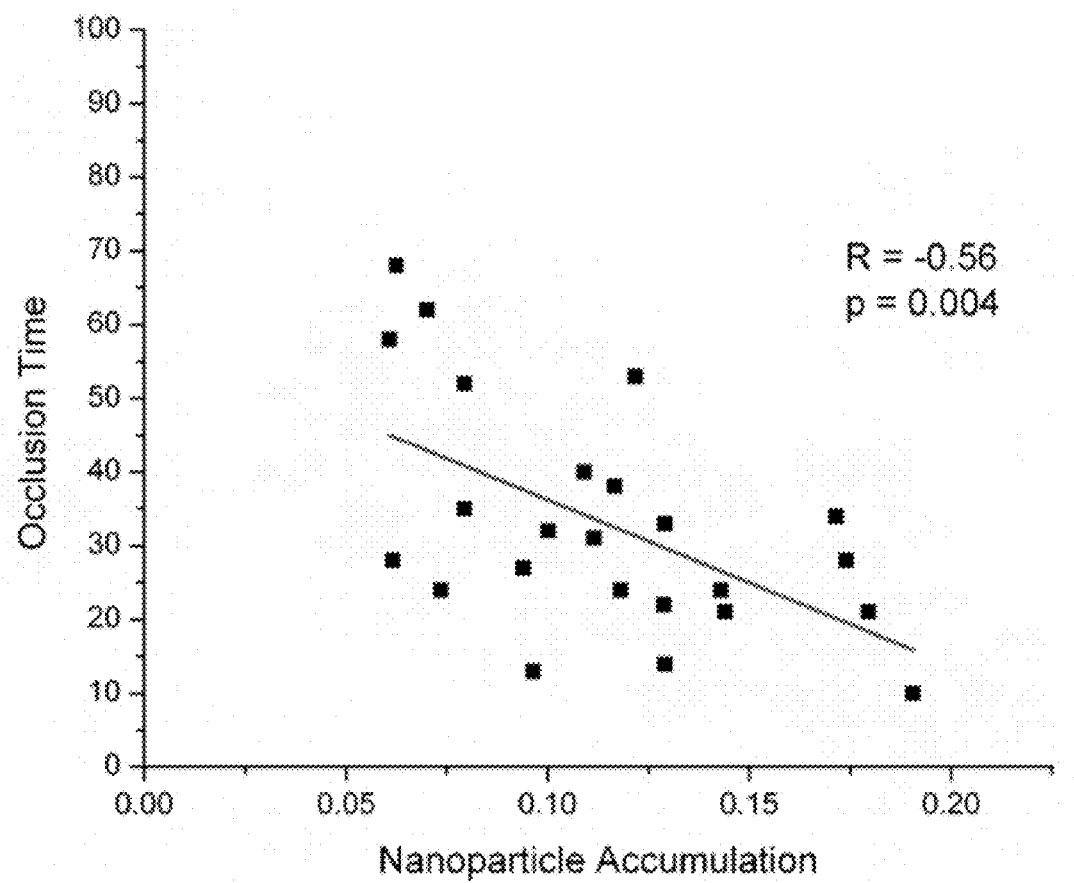
FIG. 25 is a graph of aortic nanoparticle accumulation measurements and carotid occlusion times, which demonstrates a significant inverse correlation between the two metrics, indicating a relationship between increased endothelial permeability and increased vessel hypercoagulability.
Figure 26A:
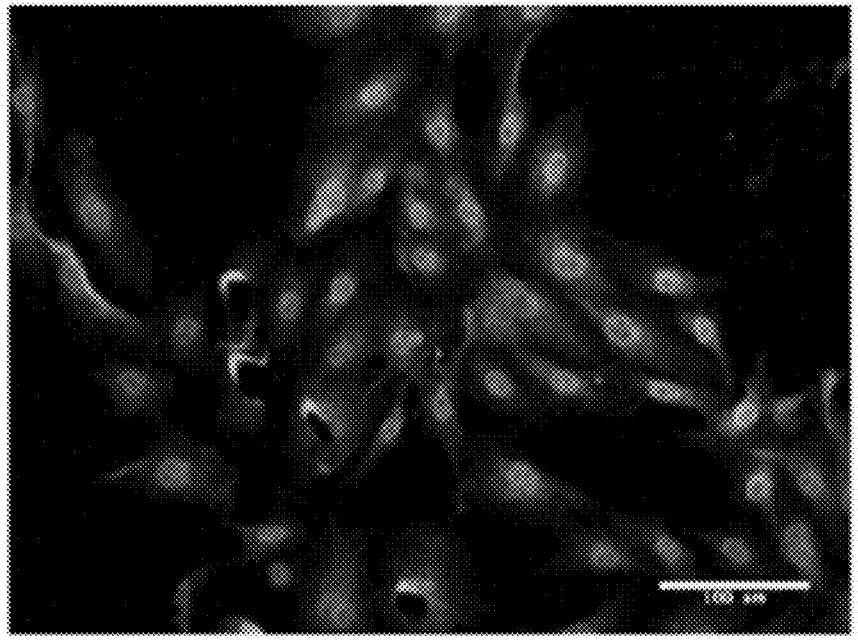
FIG. 26A-D show images of immunocytochemistry for IκB on HAECs, which demonstrates diminished degradation of IkB in response to thrombin stimulation with PPACK-NP treatment, consistent with inhibited activation of NF-kB. (A) Control (no stimulation), (B) thrombin (1 U/ml), (C) thrombin (1 U/ml)+control NP; and (D) thrombin (1 U/ml)+PPACK-NP.
Figure 26B:
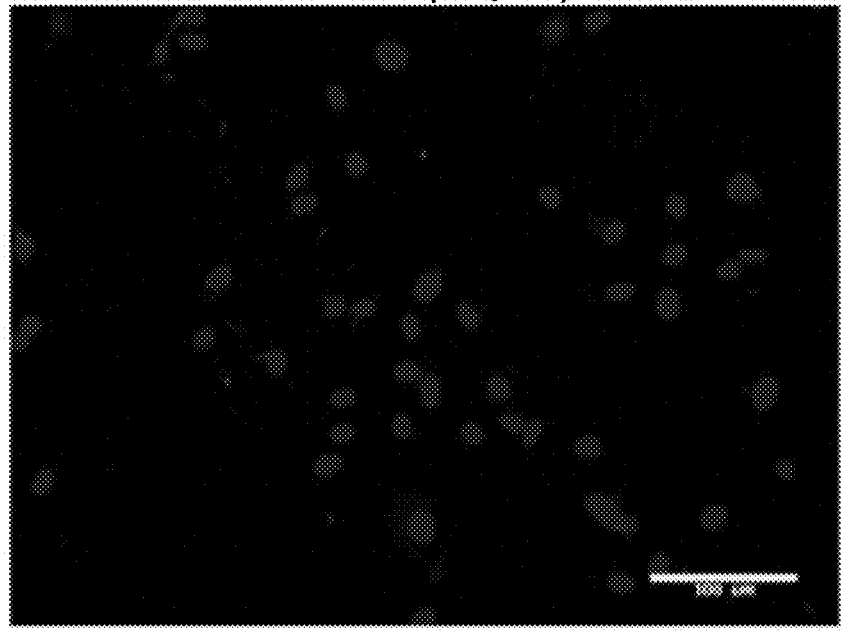
Figure 26C:
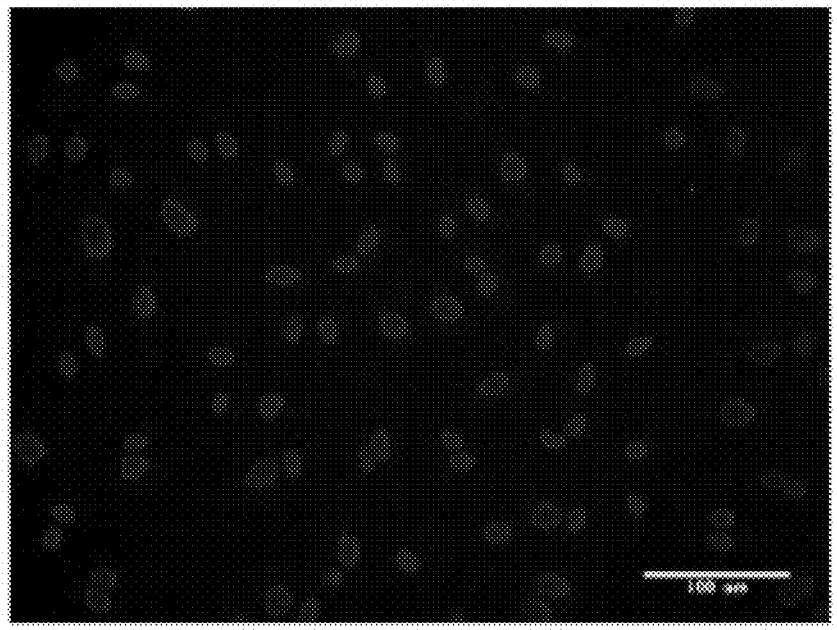
Figure 26D:
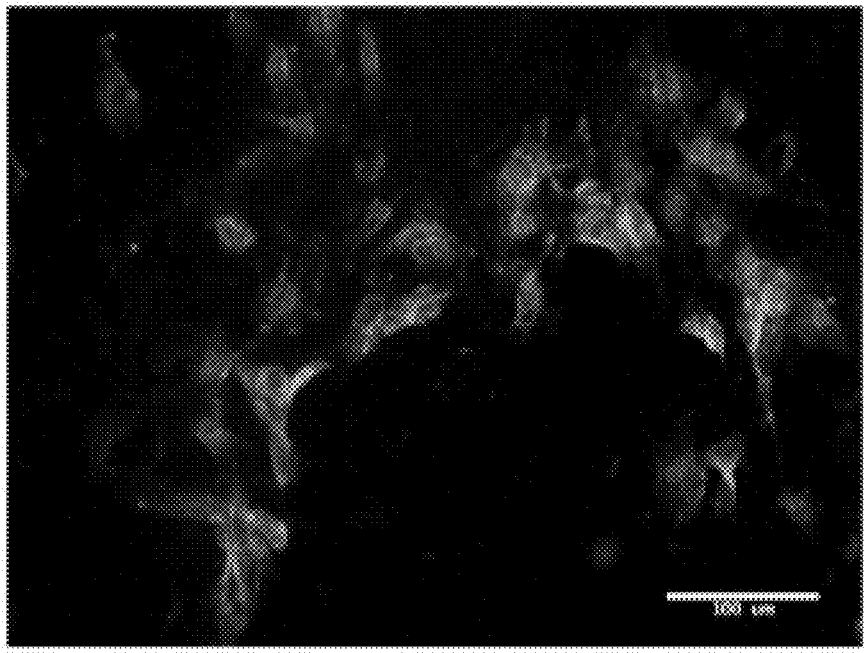

We tested the ability of PPACK-NP treatment to restore functional endothelial barriers, which concomitantly might be expected to reduce plaque procoagulant activity as previously reported.[11] Mice were injected with a dose of CE-NP for MR spectroscopy that were allowed to circulate for 2 hours prior to sacrifice, at which time plaque saturation occurs.[10] Following this circulation time, the entire length of the aorta (from the aortic root to the bifurcation) was removed for ex vivo $^{19}$F-MRS measurements at 11.7 T. FIG. 19B illustrates the beneficial effects of PPACK-NP treatment for 1 month on plaque endothelial permeability according to the decreased deposition of CE-NP (0.084±0.009 μl/g aorta, N=7) compared to saline (0.122±0.011 μl/g aorta, N=8, p=0.023) and control NP (0.132±0.013 μl/g aorta, N=10, p=0.014). Using paired samples, we observed an inverse correlation (R=−0.56, FIG. 25) between plaque permeability and vessel procoagulant activity (p=0.004), consistent with our previous observation that thrombotic risk tracks with plaque permeability to PFC-NP.

Figure 19C:
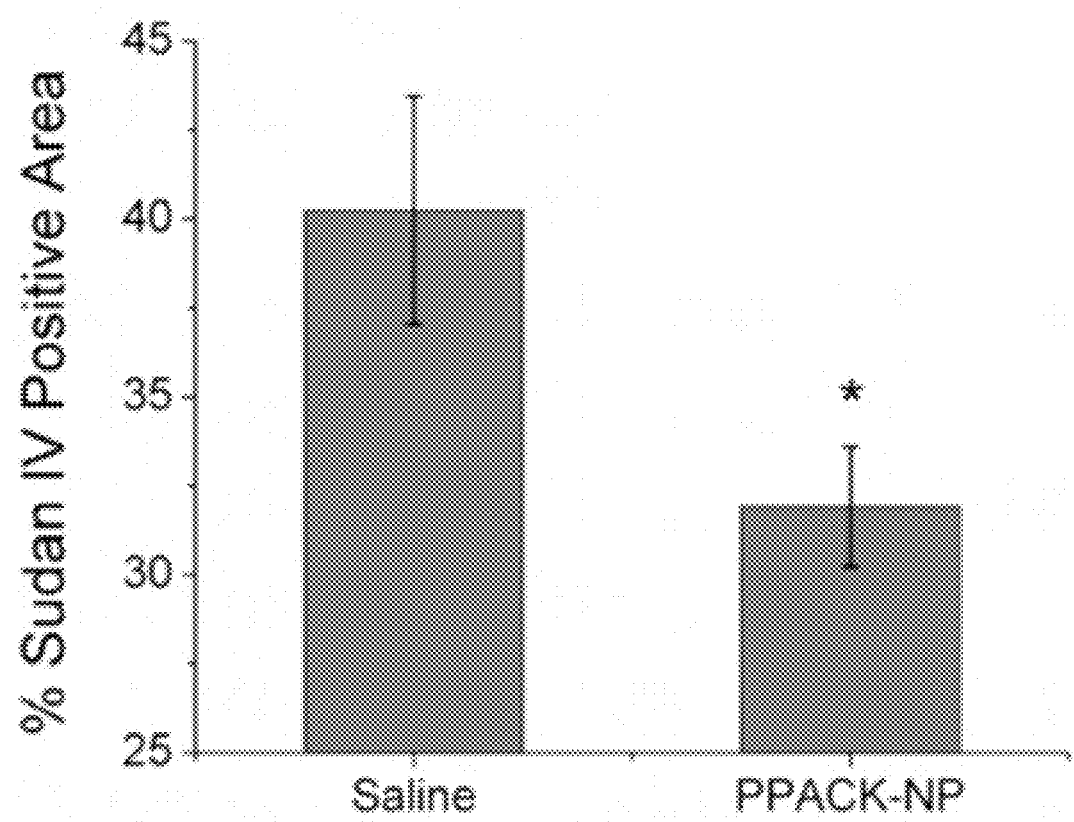

A subset of mice was allocated for measurements of plaque extent in the aortic arch by conventional Sudan IV staining and computer assisted planimetry.[20] Overall, PPACK-NP treatment resulted in a 22.5% decrease in aortic arch plaque extent (FIG. 19C): 40.24±3.21% plaque area for saline-treated mice (N=5) and 31.91±1.69% plaque area for PPACK-NP treated mice (N=7, p=0.03).

Anti-Thrombin Nanoparticles Attenuate Inflammatory Signaling Molecules.

Figure 20A:
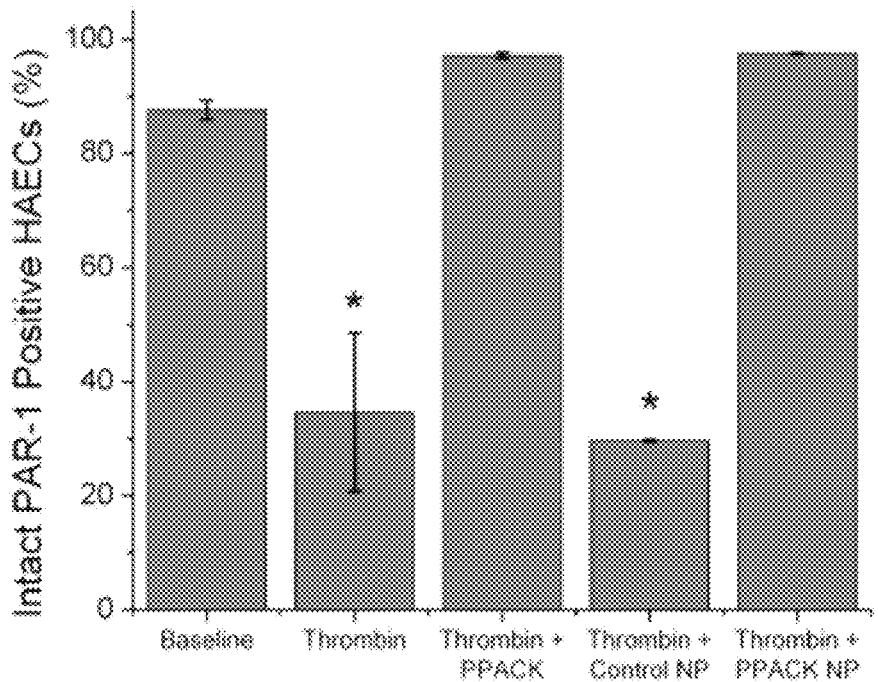
FIG. 20A-G depict graphs and images showing that anti-thrombin nanoparticles of this disclosure attenuate inflammatory signaling molecules. (A) Flow cytometry for intact PAR-1 receptors following thrombin stimulation in the presence of each treatment group demonstrates inhibition of thrombin-mediated cleavage of PAR-1 with PPACK-NP treatment. *p<0.05 (B) PPACK-NP inhibit expression of surface tissue factor on HAECs and (C) THP-1 cells in response to stimulation with different concentrations of thrombin (light gray bars, 1 U/ml; dark gray bars, 4 U/ml). p<0.005, *p<0.0005 (D) diminished tissue factor expression in PPACK-NP treated-mice (p=0.027 and 0.023 vs saline and control NP, respectively) as quantified by ImageJ in tissue sections stained for tissue factor (green) in ApoE-null mice treated with (E) saline, (F) control NP, and (G) PPACK-NP.

PAR-1 Responses:

To delineate molecular signaling events responsible for the beneficial effects of PPACK-NP, cell culture studies were used to quantify the responses of activated endothelial and monocytic cell lines to thrombin inhibition. First, as thrombin's effect on cell types is mediated primarily by cleavage of the PAR-1 receptor on cell surfaces[5], flow cytometry was used to determine the percentage of intact PAR-1 receptors that was left after treatment with thrombin in the various treatment groups. PPACK-NP treatment completely prevented thrombin cleavage of PAR-1 receptors on human aortic endothelial cells (HAECs), compared to thrombin or thrombin/control NP groups, which manifested significantly decreased PAR-1 expression (N=3 for both groups, p=0.019 and p=0.000005, respectively) as compared to baseline (FIG. 20A).

Figure 20B:
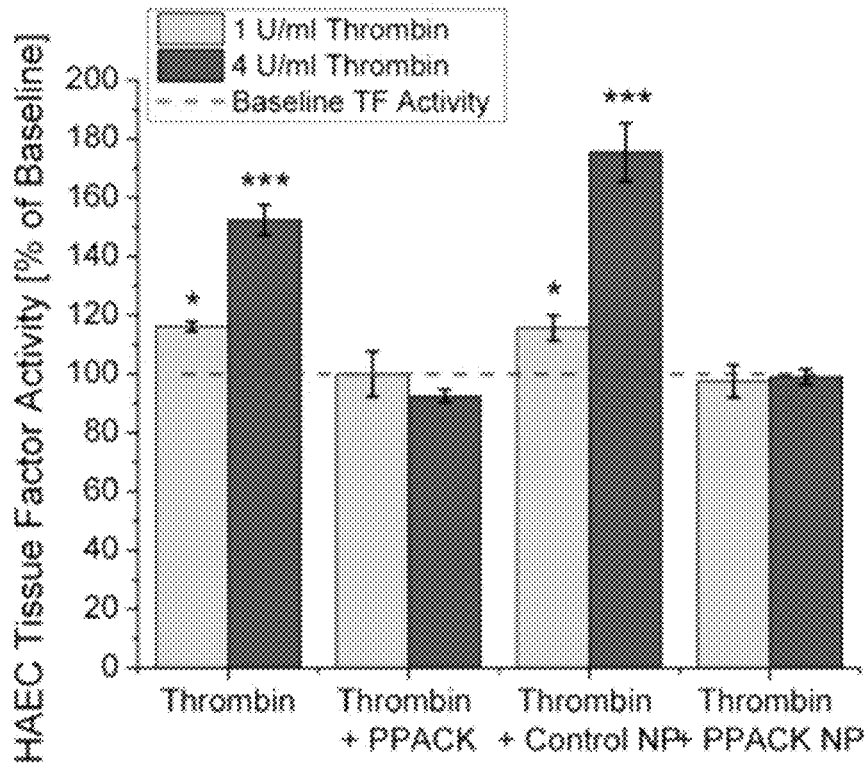
Figure 20C:
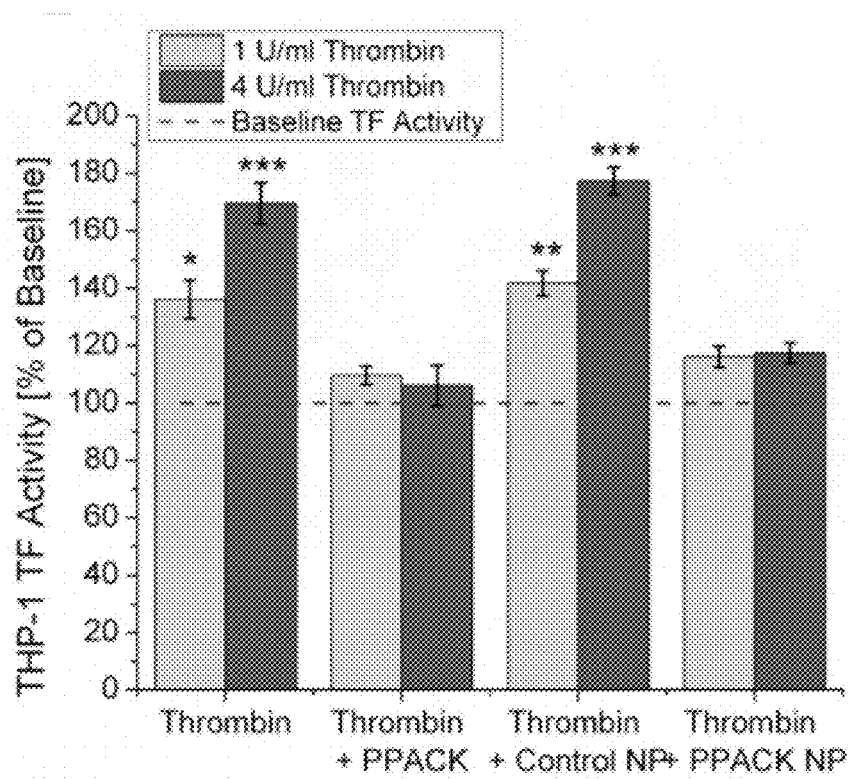
Figure 20D:
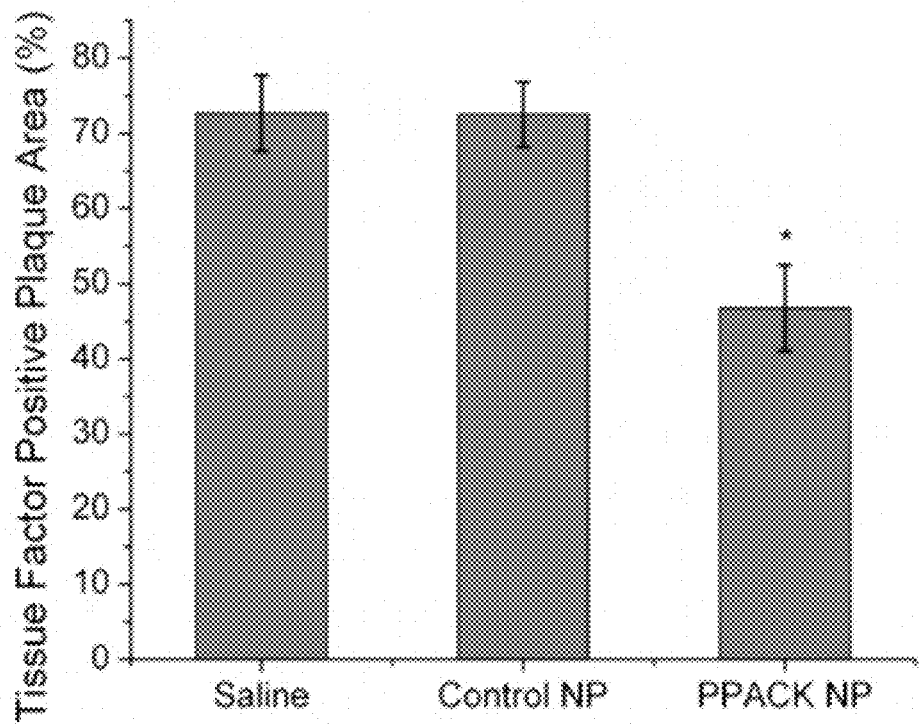
Figure 20E:
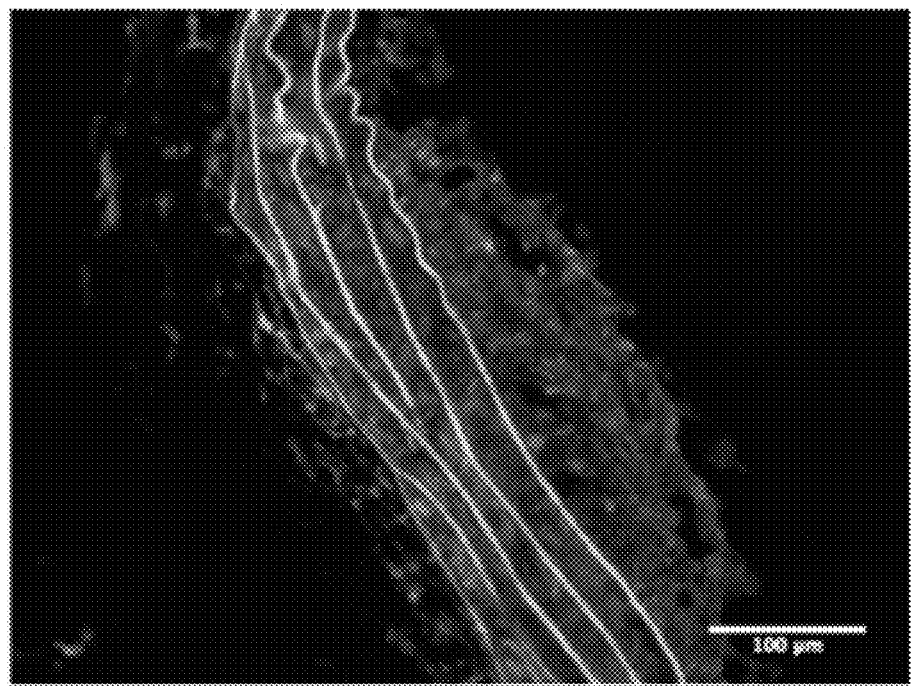
Figure 20F:
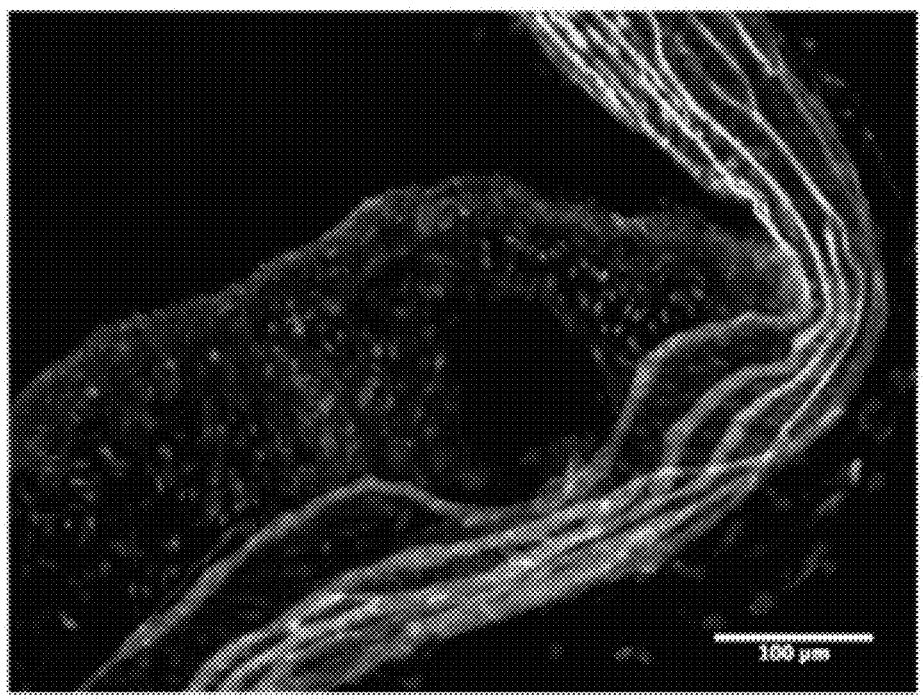
Figure 20G:
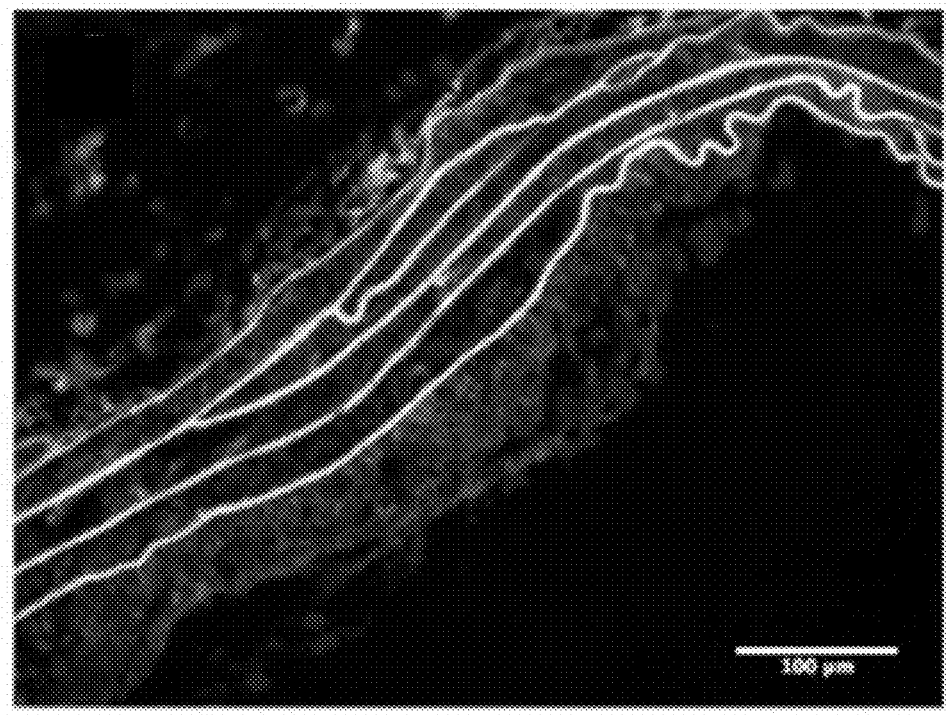

Tissue Factor Responses:

Because PPACK-NPs successfully prevented PAR-1 activation, we tested the downstream signaling effects of PAR-1 activation related to inflammation and coagulation. Expression of tissue factor on the surface of HAECs and THP-1 monocytes in response to thrombin stimulation was assayed using a functional assay of measuring FXa generation as a result of the presence of TF/FVIIa complexes. PPACK-NP prevented thrombin-induced TF expression on the surface of both HAECs (FIG. 20B) and THP-1 monocytes (FIG. 20C), with no significant increase over baseline TF levels at both concentrations of thrombin utilized (1 U/ml and 4 U/ml). Whole excised aortic arch segments exhibited a marked reduction in TF-positive plaque area after PPACK-NP treatment: 46.75±5.74% (N=3) in PPACK treated mice (FIG. 20D), versus 72.69±5.06% (N=3, p=0.027) for saline treatment and 72.52±4.34% (N=3, p=0.023) for control NP treatment as quantified in immunofluorescent staining using ImageJ (FIG. 20E-G).

NFkB Responses:

Because thrombin is known to stimulate NFkB transcriptional regulation of a panoply of inflammatory genes through PAR-1 signaling, we delineated the effect of PPACK-NP on the inhibition of NF-kB activation in HAEC (FIG. 21A-E) and THP-1 cells (FIG. 21 F-J). Thrombin cleavage of PAR-1 results in the activation of $G\alpha_q$ and dissociation of the $GI3_\gamma$ complex, which subsequently results in the parallel activation of PKCa and PI3-kinase/Akt pathways. These parallel pathways then converge to stimulate IKK, which results in the binding of the p65 homodimer to IKB and subsequent phosphorylation and degradation of IKB. Activation of the PKCa pathway results in activation of p38 which in turn, phosphorylates p65 to induce the nuclear translocation and transcriptional activity of the p65.[21]

Cell cultures were stained for phosphorylated p65 following six hours of thrombin stimulation and treatment. Treatment with PPACK-NP resulted in little to no observable positive staining for intracellular phospho-p65 and preservation of IkB protein (FIG. 26) compared to thrombin and thrombin/control NP treatment groups. The preservation of IkB indicates that this cytoplasmic regulatory component of p65/p50 retains control of the preexisting cytoplasmic stores of p65 thereby preventing subsequent p65 phosphorylation and translocation to the nucleus.

Figure 21A:
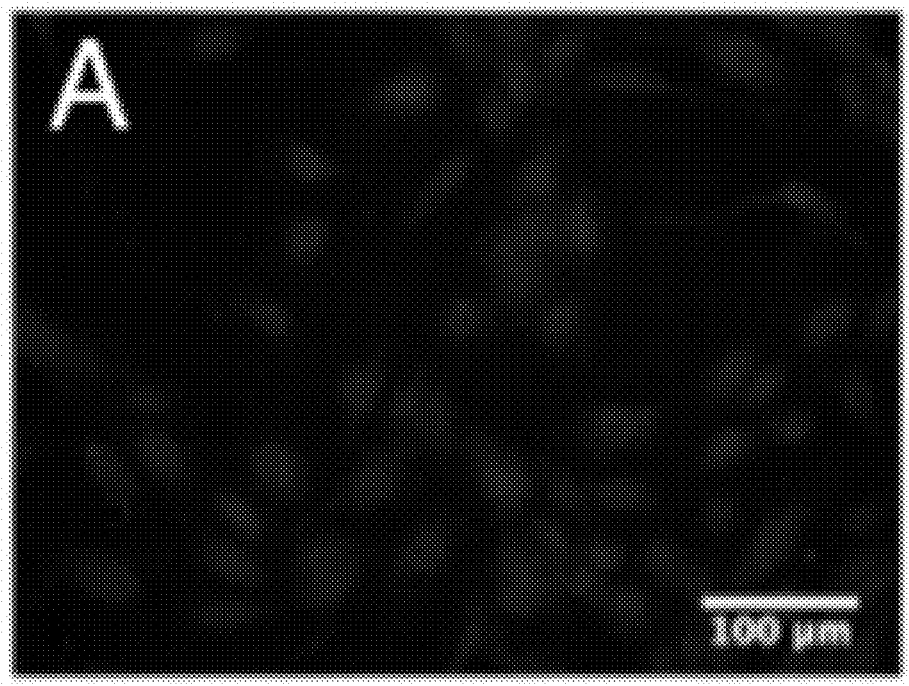
FIG. 21A-R depict graphs and images showing that anti-thrombin nanoparticles of this disclosure attenuate inflammatory signaling molecules. Immunocytochemistry for phosphorylated p65 demonstrates inhibition of NF-κB activation in (A-E) HAECs and (F-J) THP-1 cells with PPACK-NP treatment. (A, F) baseline; (B, G) Thrombin, (C, H) Thrombin+PPACK, (D, I) Thrombin+Control NP, and (E, J) Thrombin+PPACK NP. ImageJ quantification of (K) endothelial and (L) intraplaque phospho-p65 staining on ApoE-null mouse plaques demonstrate significantly less endothelial and macrophage phospho-p65. Representative images are shown in (M-O). Von Willebrand factor staining was conducted on neighboring sections to rule out loss of endothelial phospho-p65 staining due to missing endothelium in this case, and representative images are shown in (P-R). (M, P) Saline, (N, Q) Control NP, and (Q, R) PPACK NP.
Figure 21B:
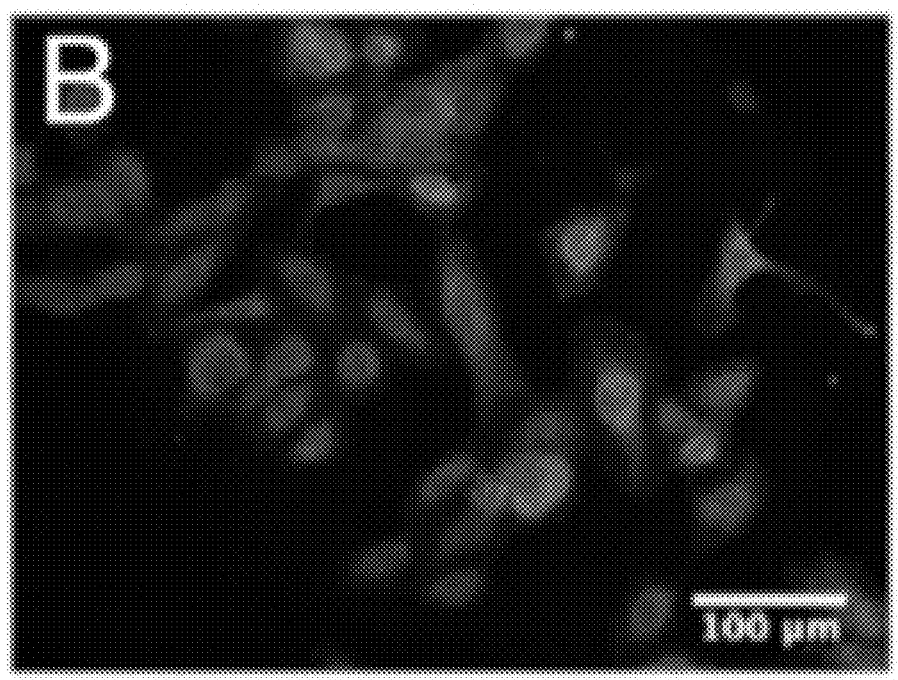
Figure 21C:
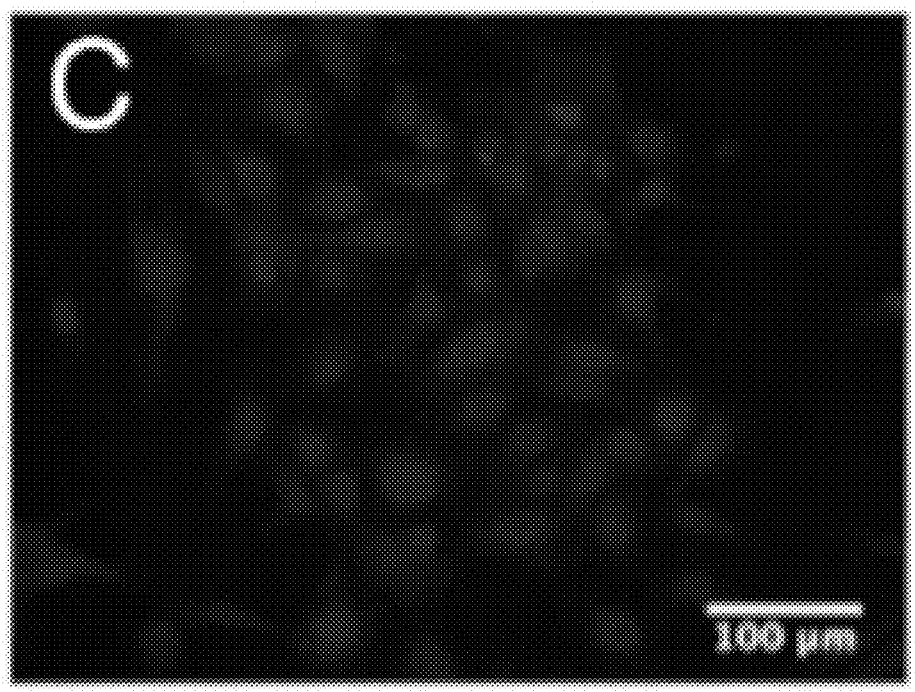
Figure 21D:
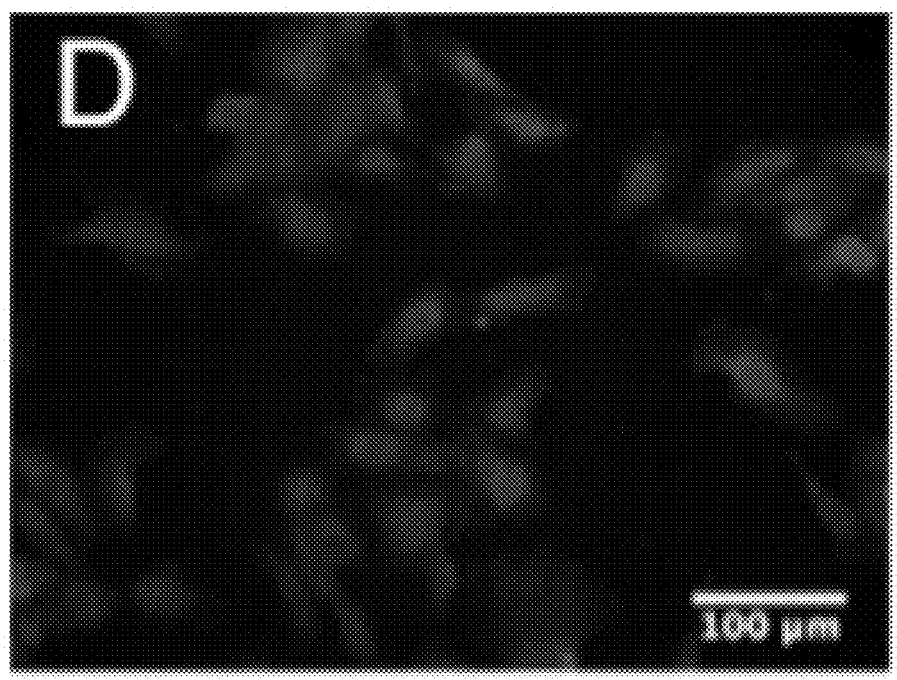
Figure 21E:
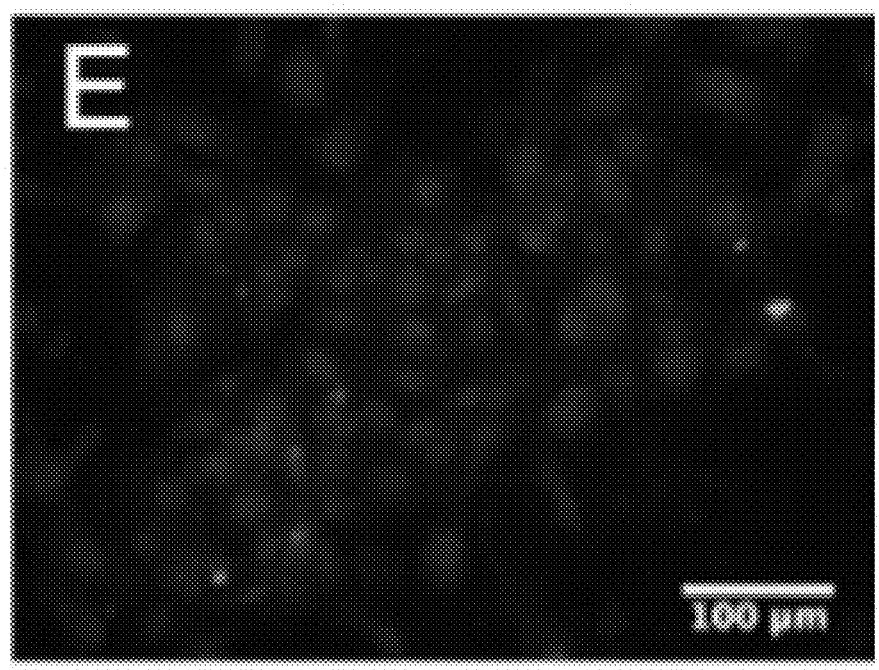
Figure 21F:
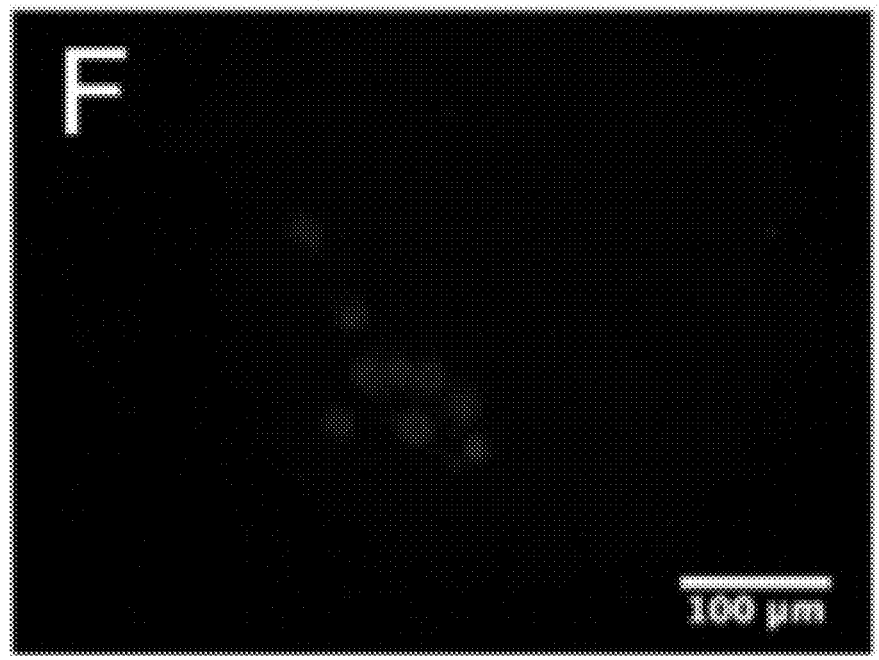
Figure 21G:
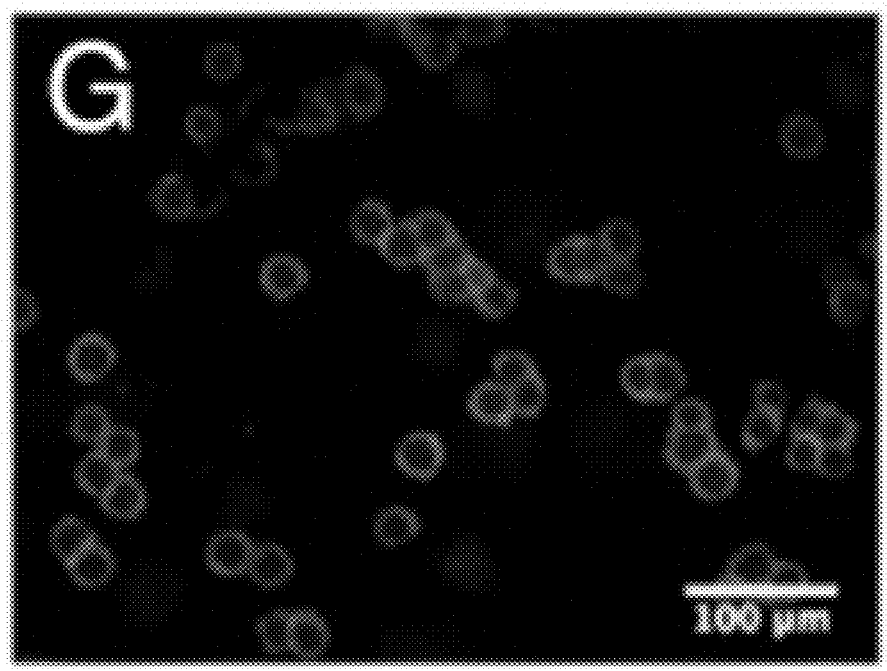
Figure 21H:
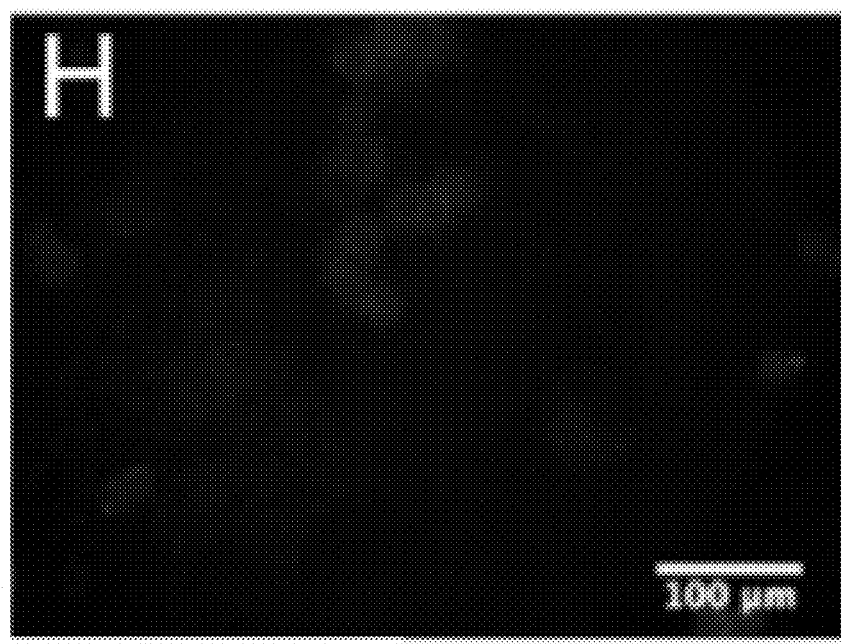
Figure 21I:
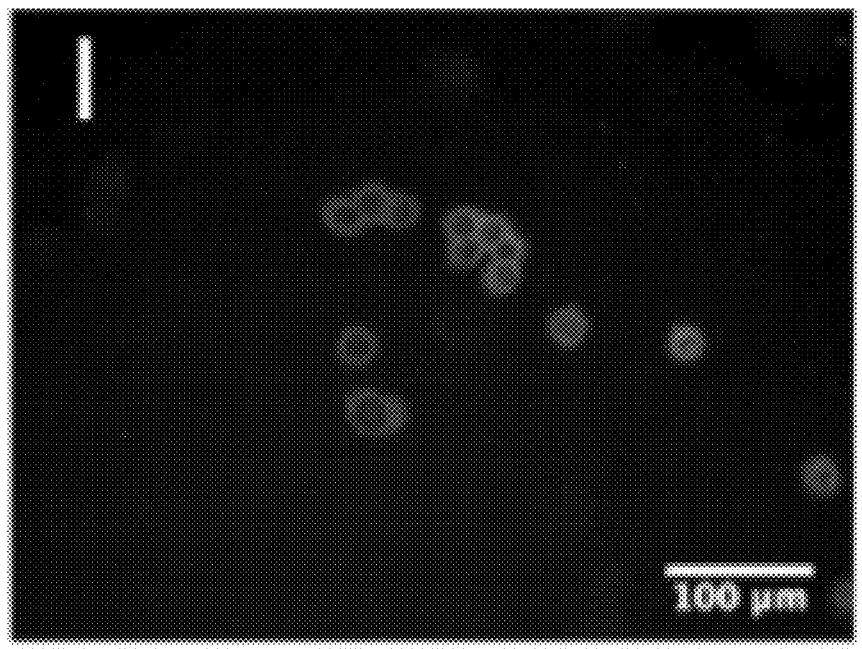
Figure 21J:
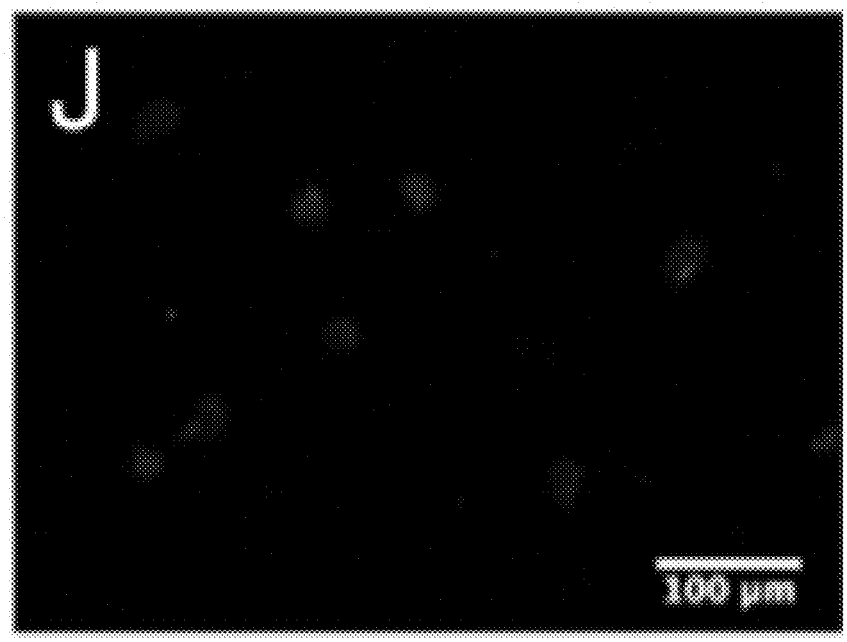
Figure 21K:
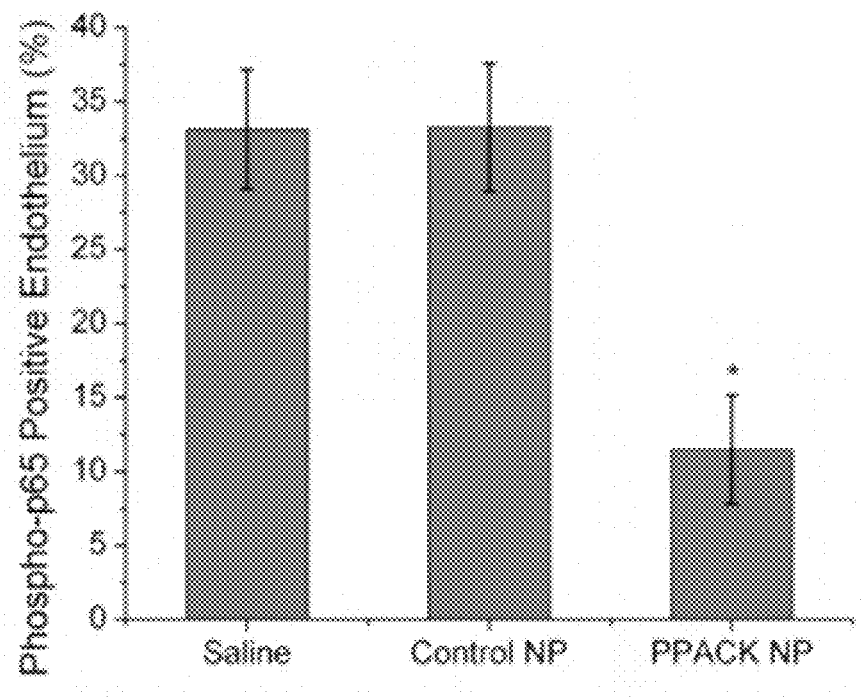
Figure 21L:
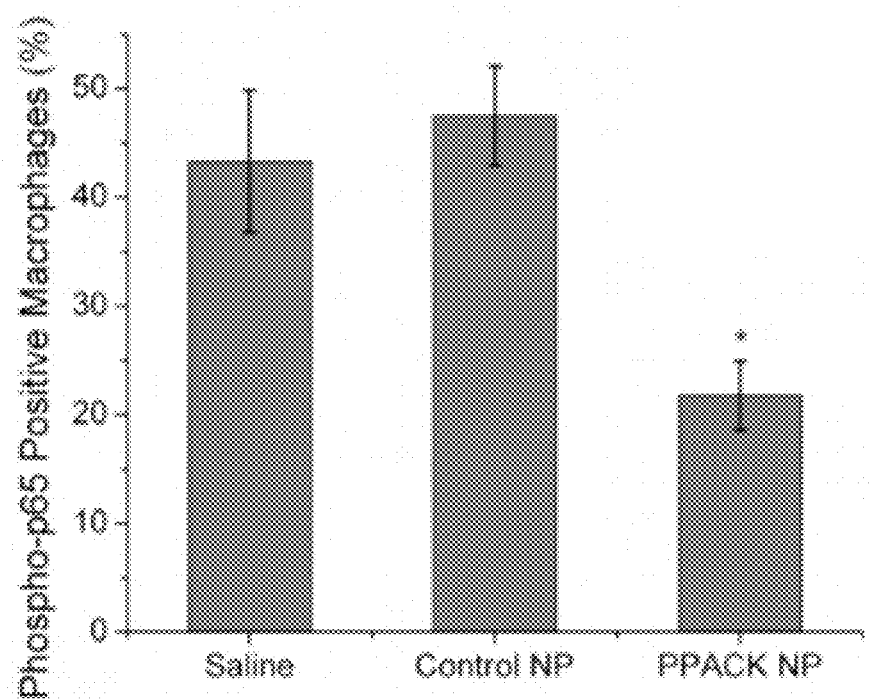
Figure 21M:
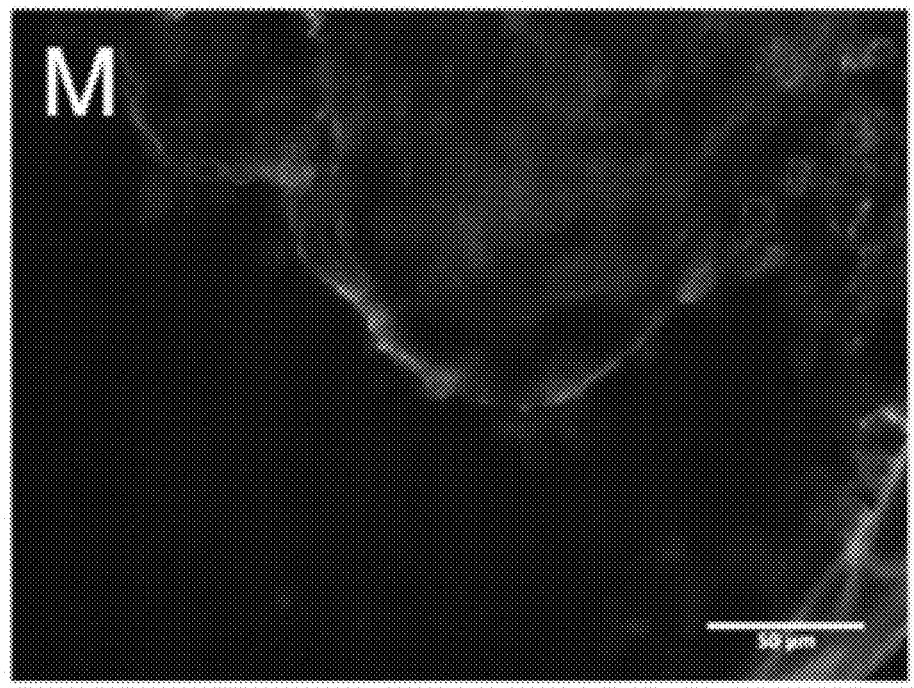
Figure 21N:
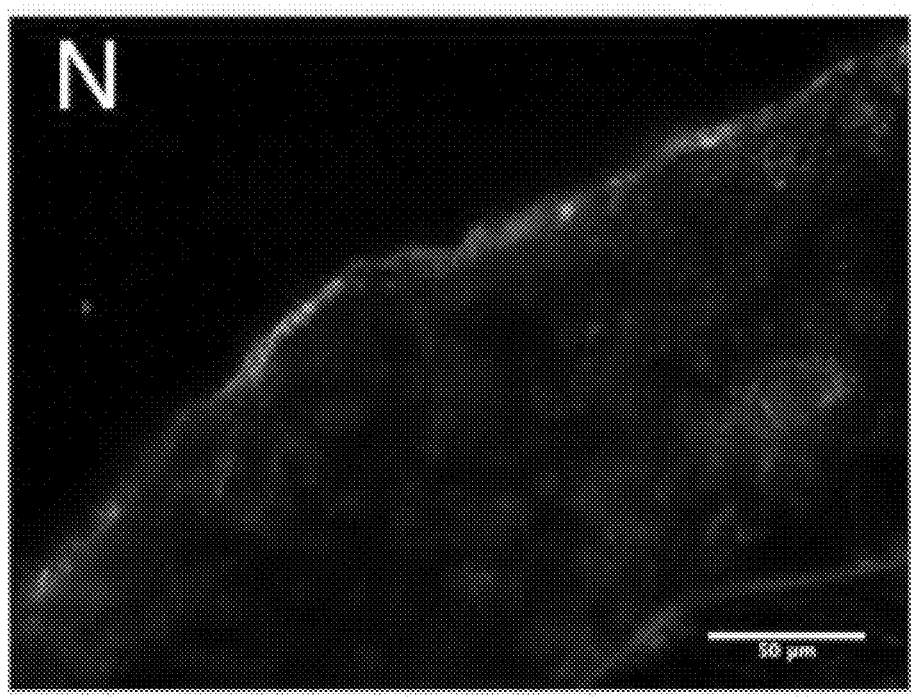
Figure 21O:
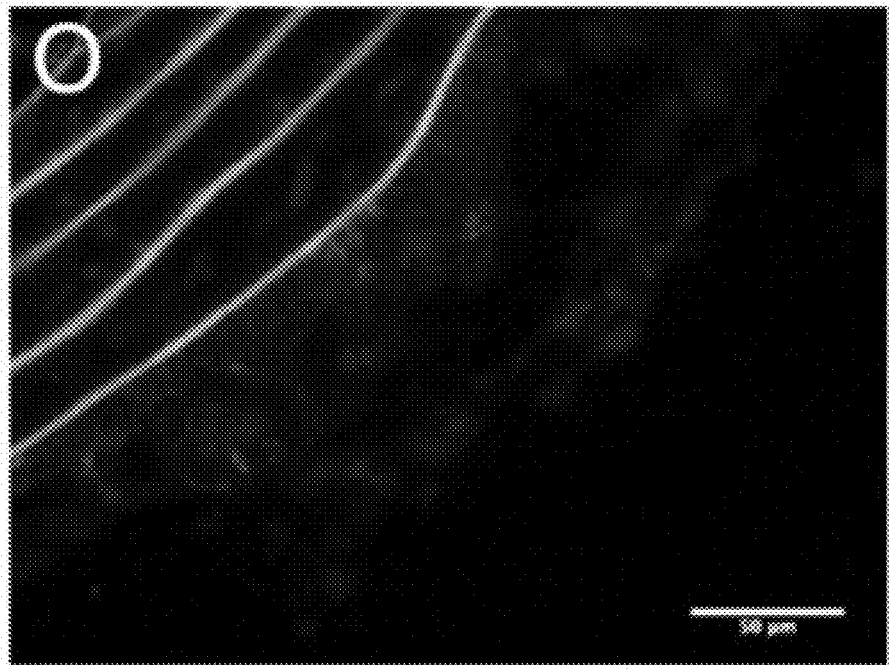
Figure 21P:
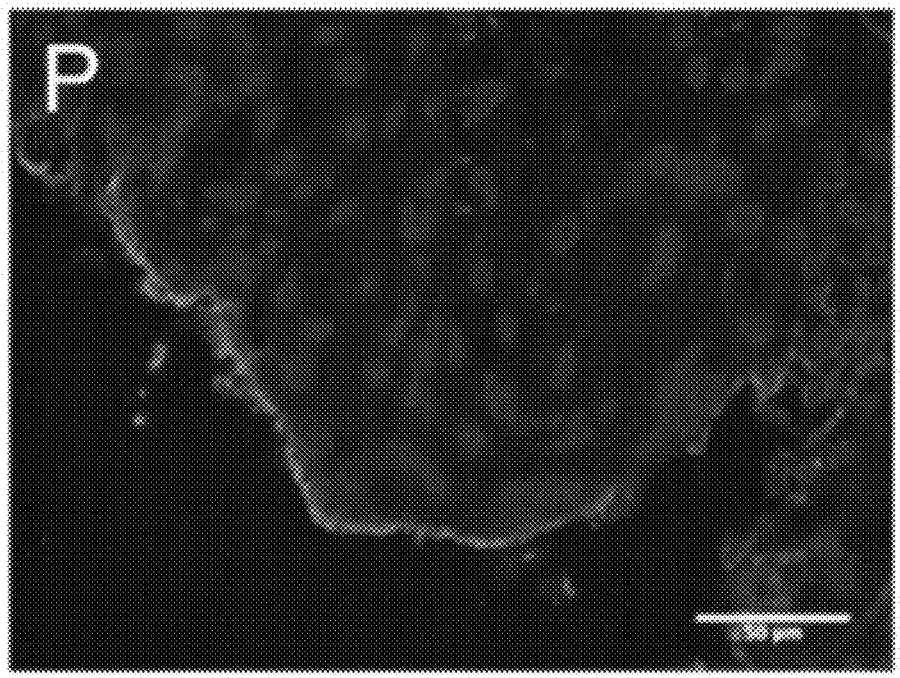
Figure 21Q:
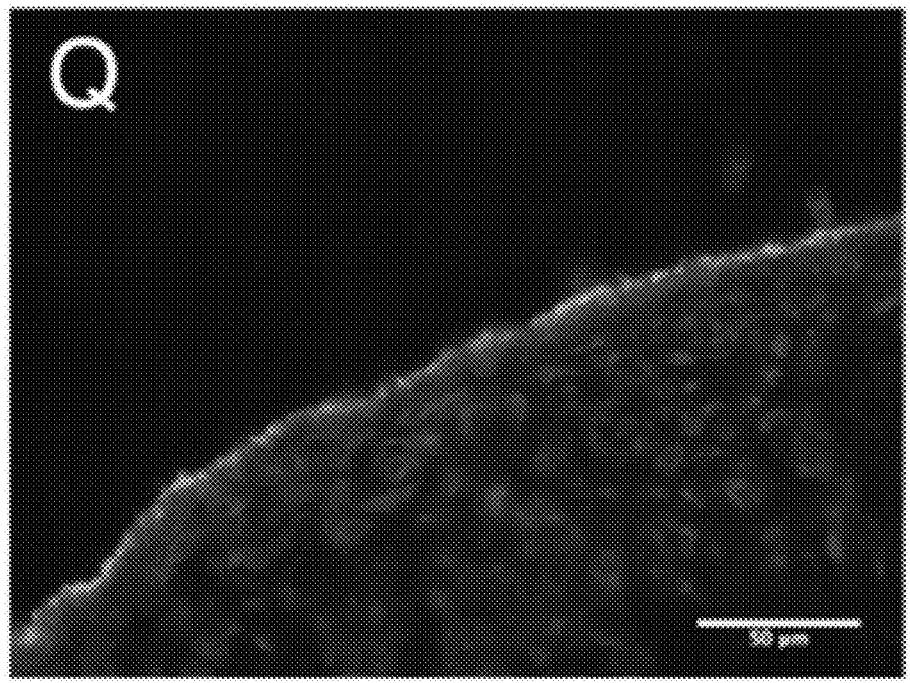
Figure 21R:
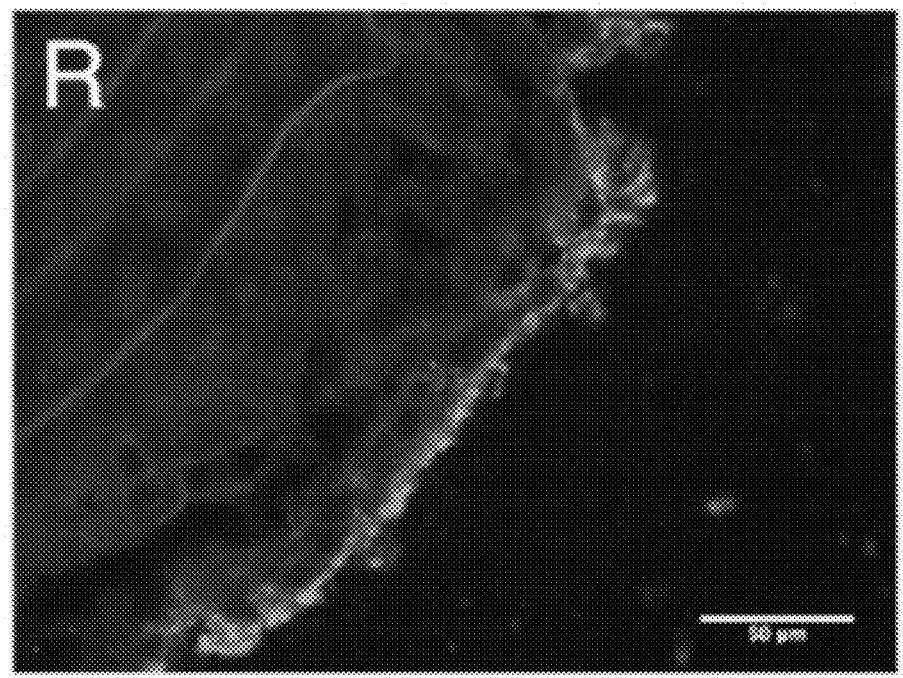

Next we quantified pp65 in the endothelium (FIG. 21K) and intraplaque regions (FIG. 21L), by staining sections of the excised aortic arch for phosphorylated NF-kB p65 (pp65, FIG. 21M-O), where increased phosphorylation of p65 indicates increased NF-kB activity. After PPACK-NP treatment, aortic plaques exhibited significantly decreased endothelial pp65 (11.49±3.66%, N=3) compared to saline (33.11±4.05%, N=3, p=0.017) and control NP treatments (33.25±4.33%, N=3, p=0.019). Decreased macrophage pp65 also was observed in plaque regions after PPACK-NP treatment (21.78±3.15%, N=3) compared to saline (43.31±6.55%, N=3) and control NP treatments (47.51±4.59%, N=3). To rule out loss of endothelial pp65 staining due to missing endothelium, selected neighboring slide sections where pp65 was noted to be reduced were stained for vWF, indicating that endothelium was present, thus confirming the specificity for NFkB downregulation by PPACK-NP in endothelium in vivo (FIG. 21P-R).

Figure 22A:
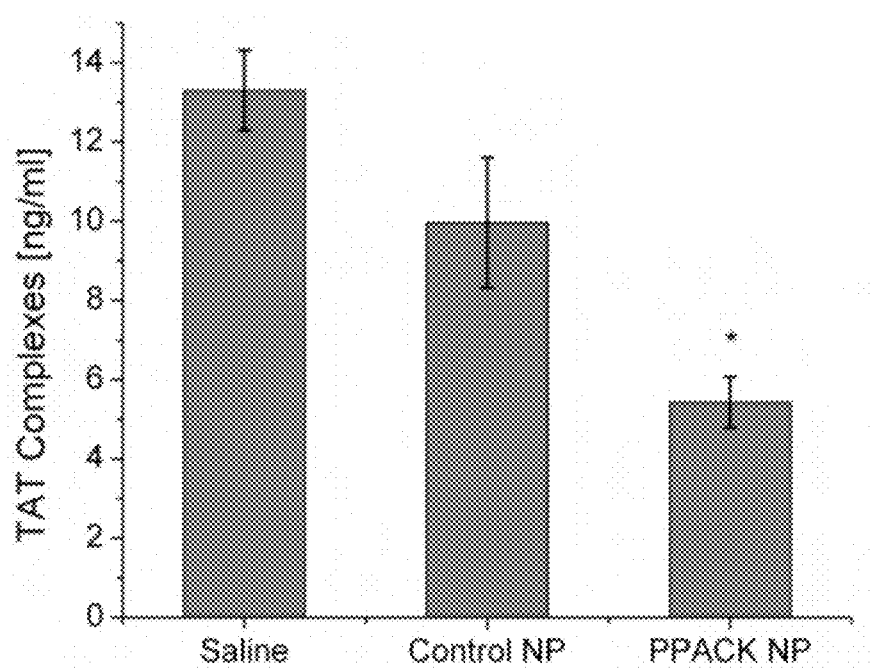
FIG. 22A-B depict graphs and images showing that anti-thrombin nanoparticles of this disclosure attenuate inflammatory signaling molecules and procoagulant molecules. (A) ELISA evaluation of thrombin-antithrombin complexes reveals a significant decrease in detected TAT-complexes following one month of PPACK-NP treatment. (B) ELISA analysis for detection of serum soluble VCAM-1 (sVCAM-1) demonstrated a decrease in detectable sVCAM-1 following one month of PPACK-NP treatment.

Systemic Coagulation and Inflammation Markers:

Thrombin-antithrombin (TAT) complexes are correlative systemic harbingers of procoagulant activity.[22] PPACK-NP treatment significantly reduced serum thrombin-antithrombin (TAT) complexes (5.43±0.64 ng/ml, N=5; p=0.0001 vs. saline, p=0.032 vs control NP) (FIG. 22A) versus saline (13.32±1.01 ng/ml, N=6) and control NP (9.96±1.64 ng/ml, N=5, p=NS vs. saline).

Because NF-kB is a known driver of endothelial adhesion molecules, we measured soluble VCAM-1 (sVCAM-1) levels as biomarkers of activated endothelium in atherosclerosis.[23] ELISA analysis of sVCAM-1 (FIG. 22B) revealed a modest, but significant decrease in sVCAM-1 with PPACK-NP treatment (1504.88±65.25 ng/ml, N=4) compared to saline treatment (1666.37±12.78 ng/ml, N=5, p=0.029)

Figure 23A:
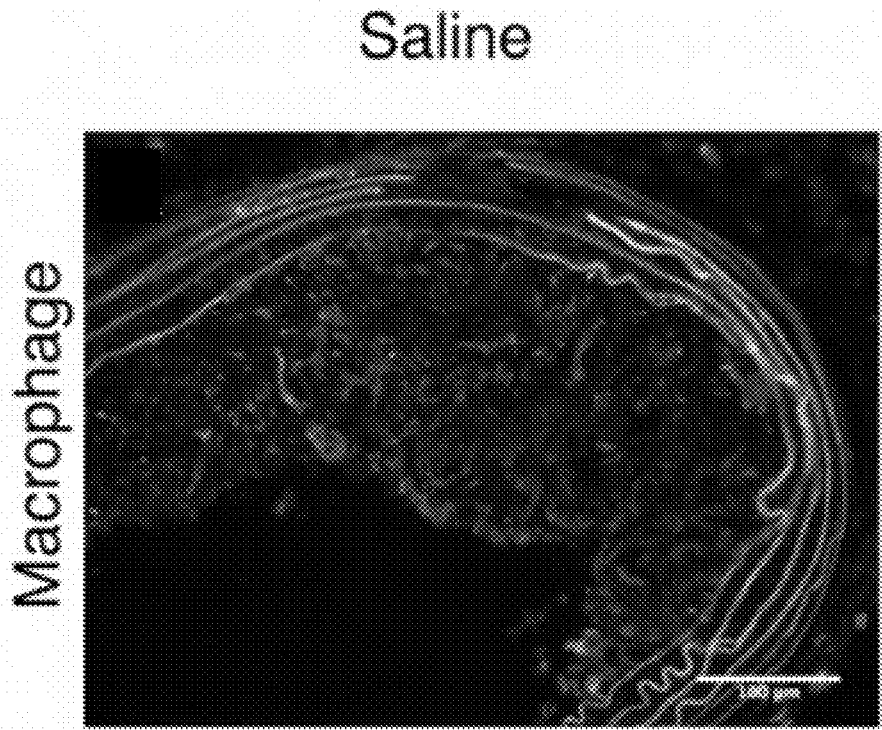
FIG. 23A-F depicts graphs and images showing that anti-thrombin nanoparticles of this disclosure attenuate inflammatory signaling molecules and procoagulant molecules. Immunofluorescent staining for macrophages in ApoE-null mouse plaques treated with (A) saline, (B) control NP, and (C) PPACK-NP revealed no significant difference in (D) detected plaque macrophages as quantified with ImageJ. (E) No significant difference in activated partial thromboplastin time (APTT) between treatment groups indicating no persisting systemic effect of PPACK-NP on coagulation 2-3 days after the penultimate treatment dose. (F) No significant difference was observed on serum cholesterol between treatment groups, indicating that therapeutic effects observed occurred without cholesterol lowering as a consequence of nanoparticle treatment
Figure 23B:
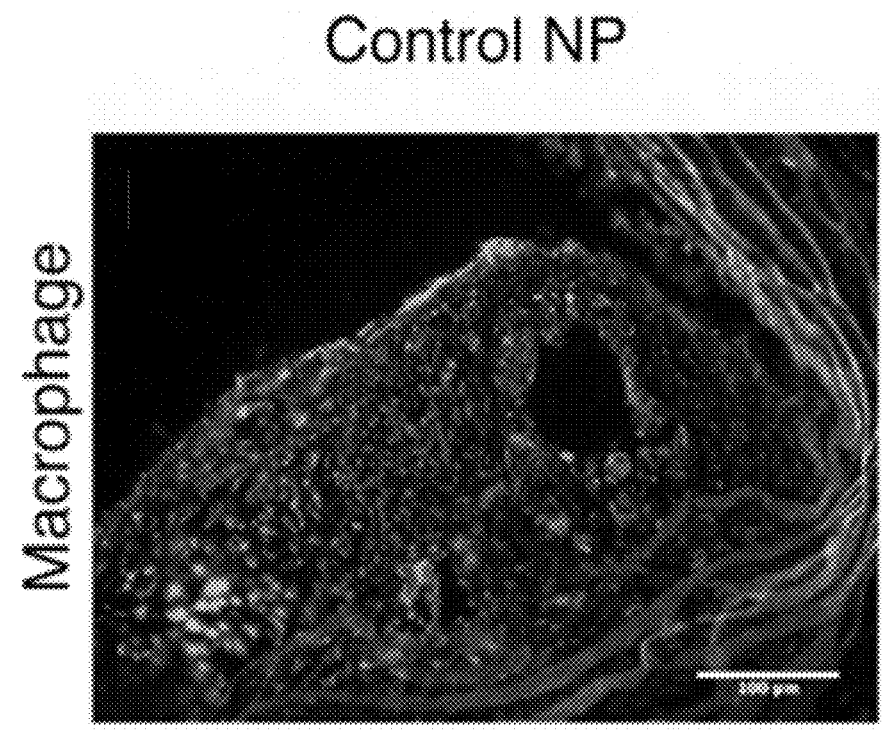
Figure 23C:
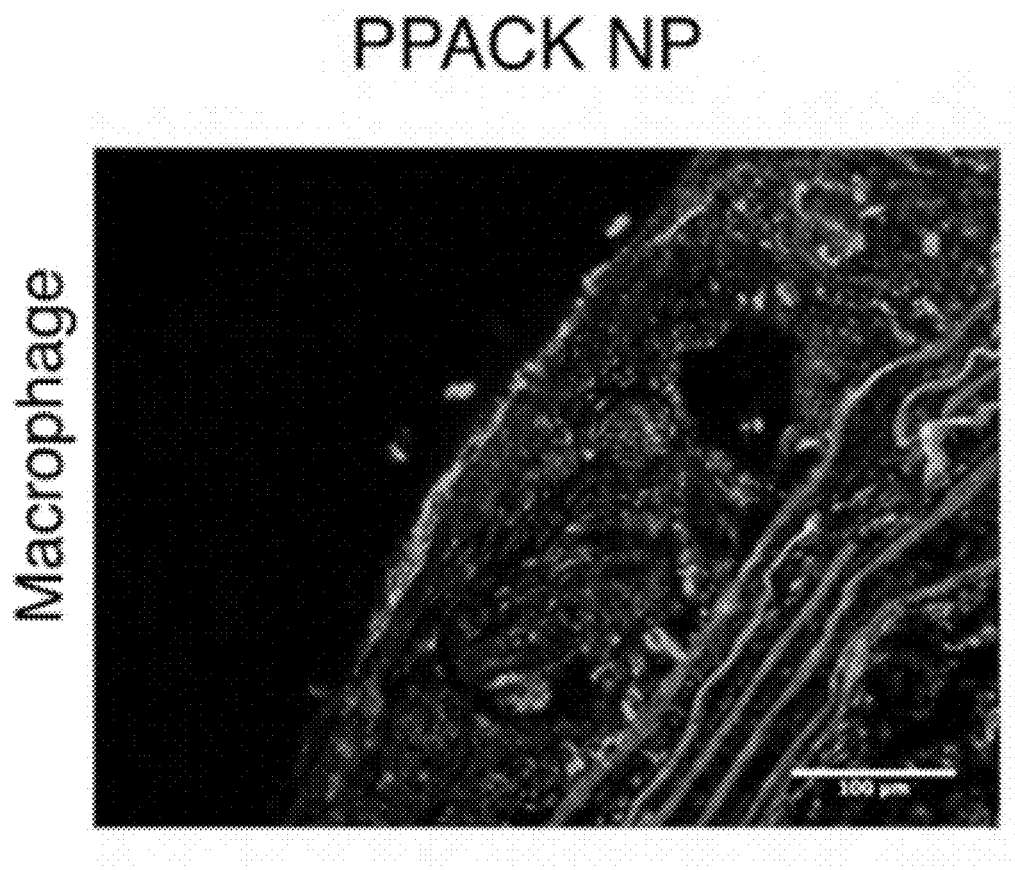
Figure 23D:
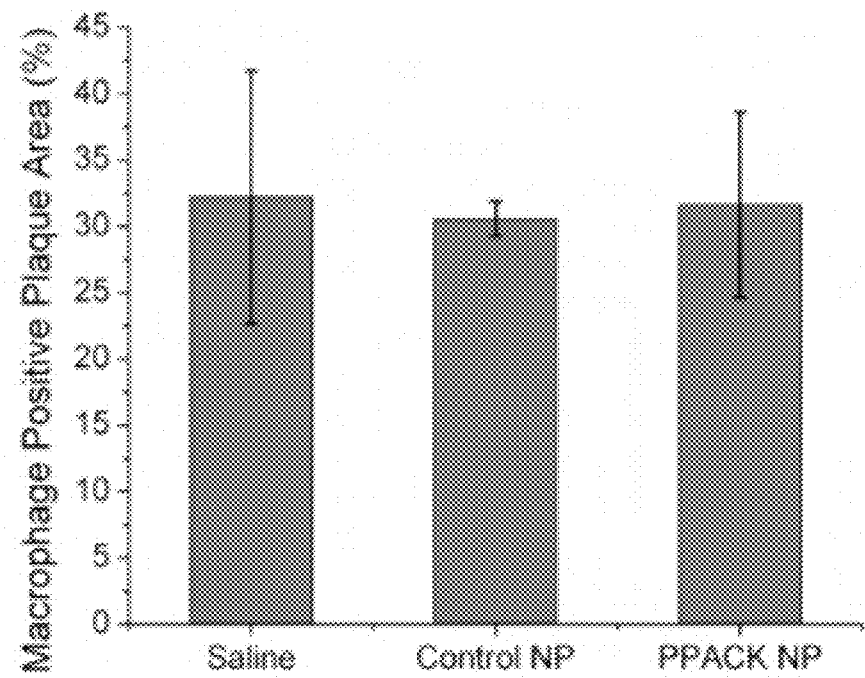

Macrophage Responses:

Excised aortic arch sections were stained for macrophages (FIG. 23A-C) and plaque macrophage content was quantified using ImageJ. We observed no significant difference between treatment groups in terms of overall plaque macrophage content (FIG. 23D).

Figure 23E:
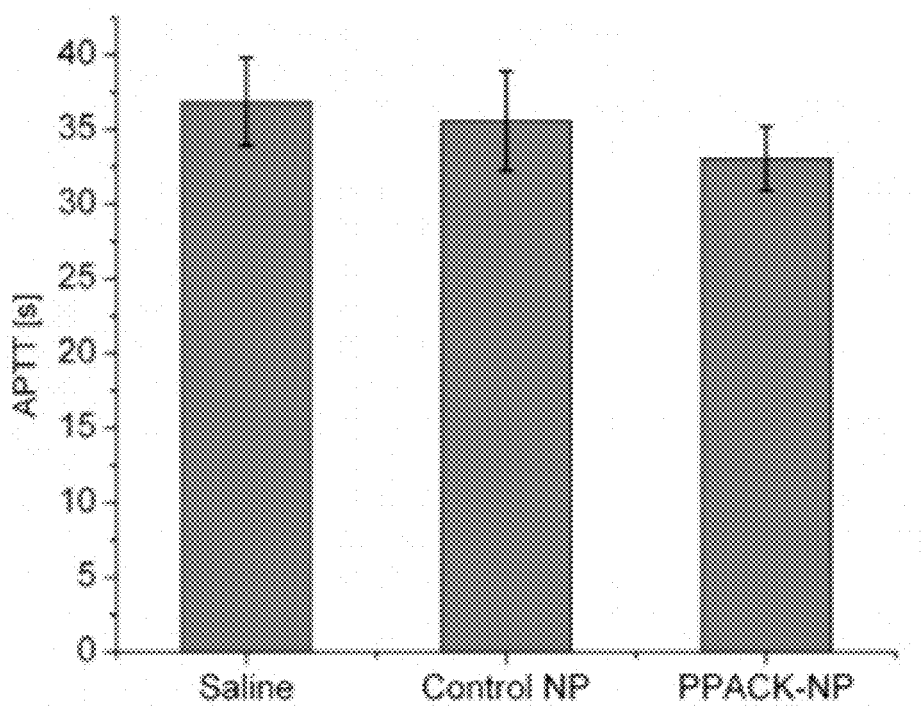
Figure 23F:
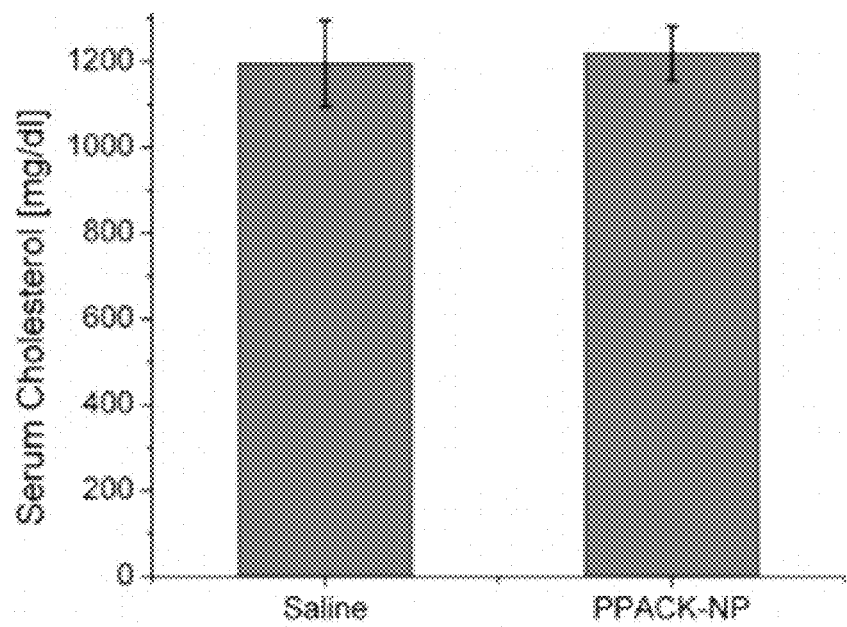

Systemic Responses to PPACK-NP:

APTT measurements conducted on serum collected at the time of sacrifice indicated no persistent non-specific effects of PPACK-NP after the terminal treatment dose 2-3 days prior to sacrifice (FIG. 23E). Furthermore, no significant difference was observed in serum cholesterol following the PPACK-NP treatment regimen (FIG. 23F).

Figure 27:
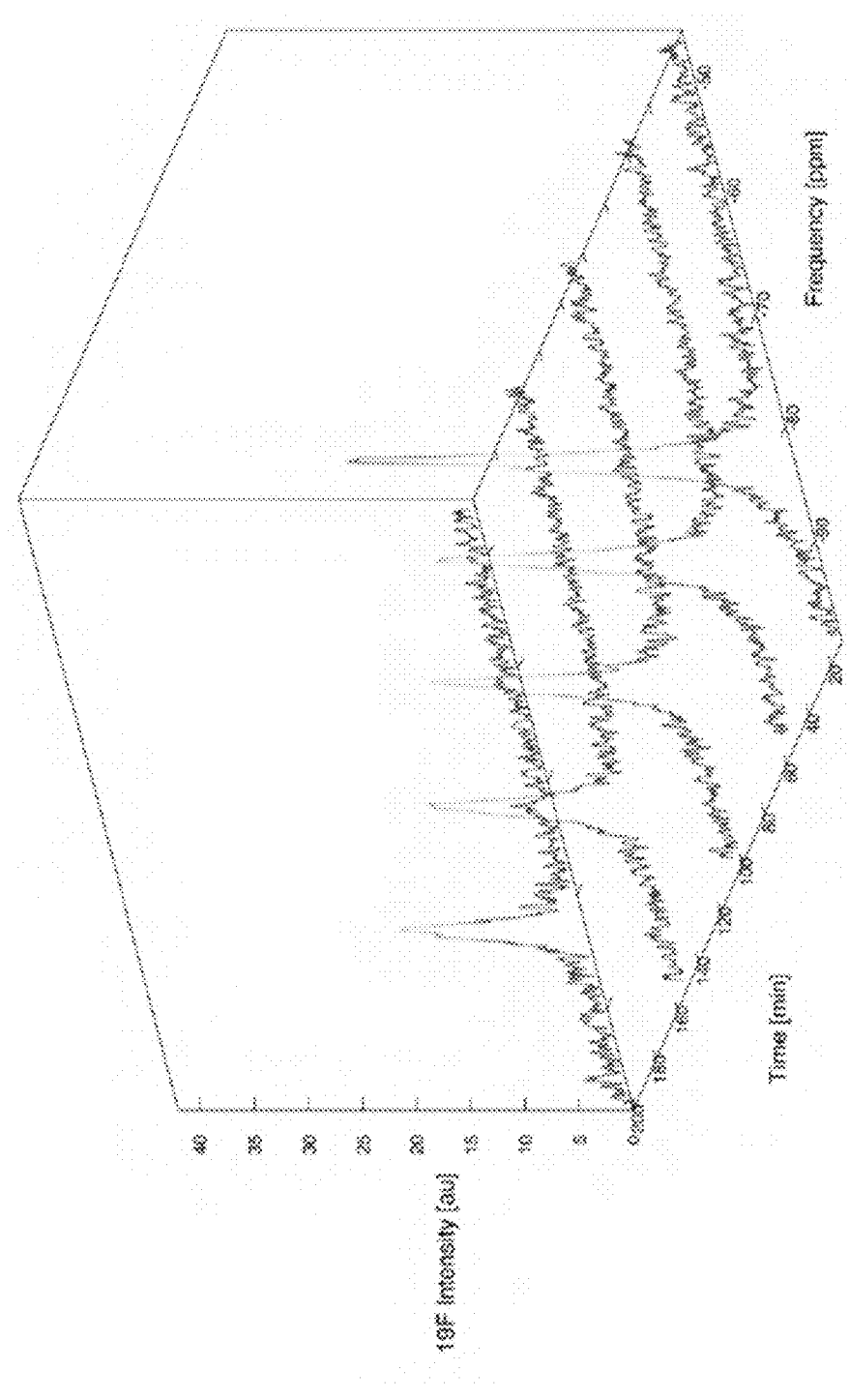
FIG. 27 is a representation of a temporal series of $^{19}$F spectra for one mouse at increasing times after a bolus dose of PFC-NP. Signal decay can be monitored through decrease in the $^{19}$F signal intensity and fit to a biexponential model to estimate clearance half-life. Depicted spectra reflect an arbitrary scale for signal strength. Frequencies are given as PPM (parts per million) assuming a 190 MHz spectrometer frequency.
Figure 28:
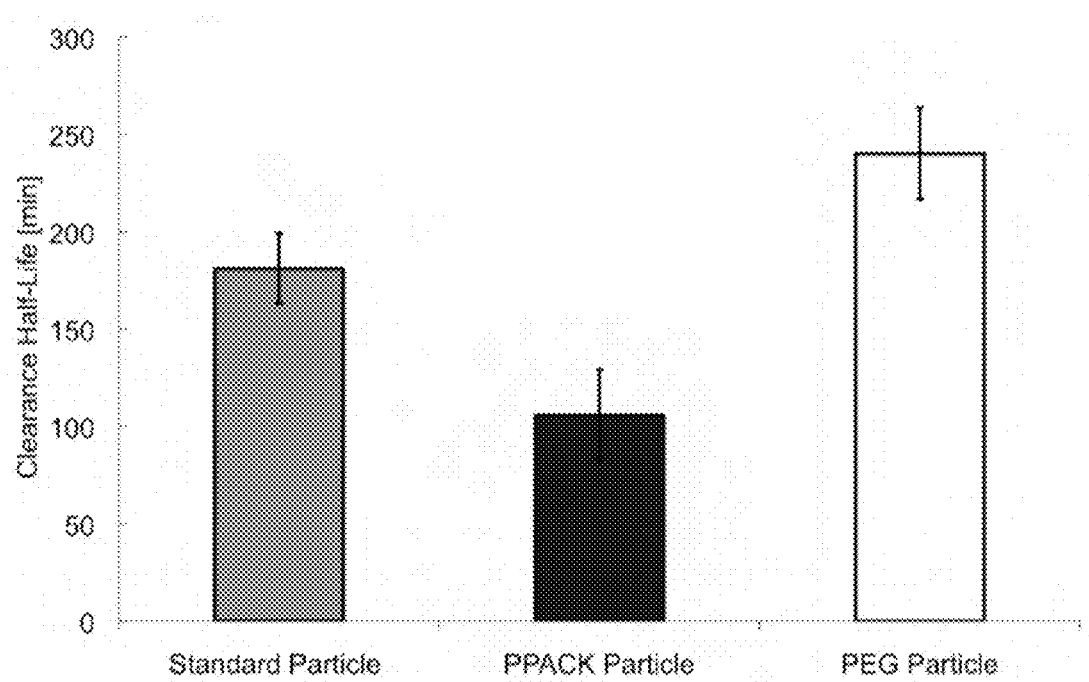
FIG. 28 is a graph depicting clearance half-life for selected nanoparticles. $^{19}$F MRS determined clearance half-lives for PPACK-functionalized PFC nanoparticles (105.87±23.38 minutes), PFC nanoparticles with a surface conjugated carboxy-PEG spacer (240.16±23.42 minutes), and non-functionalized PFC nanoparticles (181.3±40.7 minutes).
Figure 29:
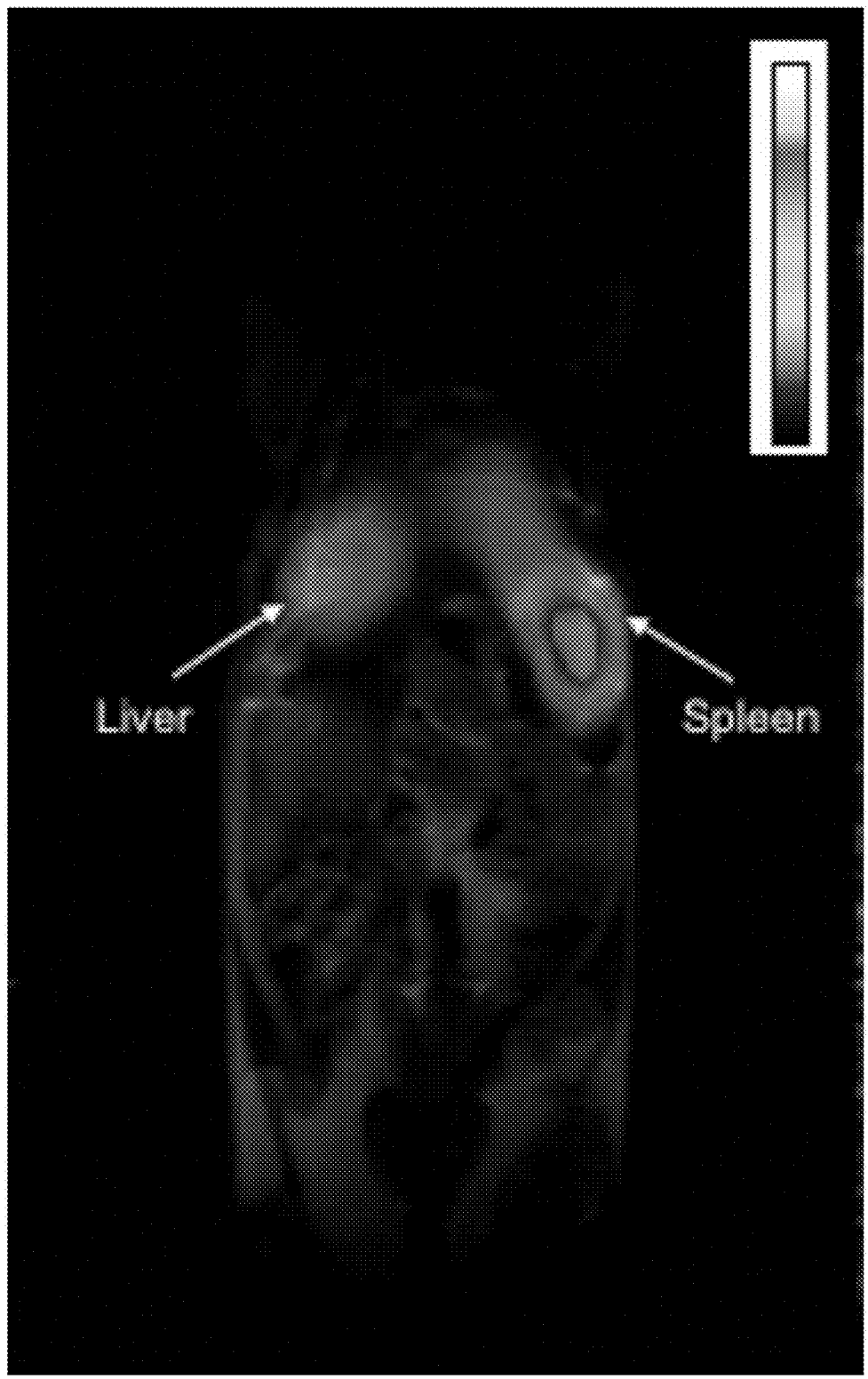
FIG. 29 is a $^{19}$F spin echo coronal projection image (false color) overlaid on a proton spin echo coronal slice image (grayscale). The image, demonstrating nanoparticle accumulation in the spleen and liver, was acquired post-mortem in a mouse sacrificed two hours after injection.
Figure 30:
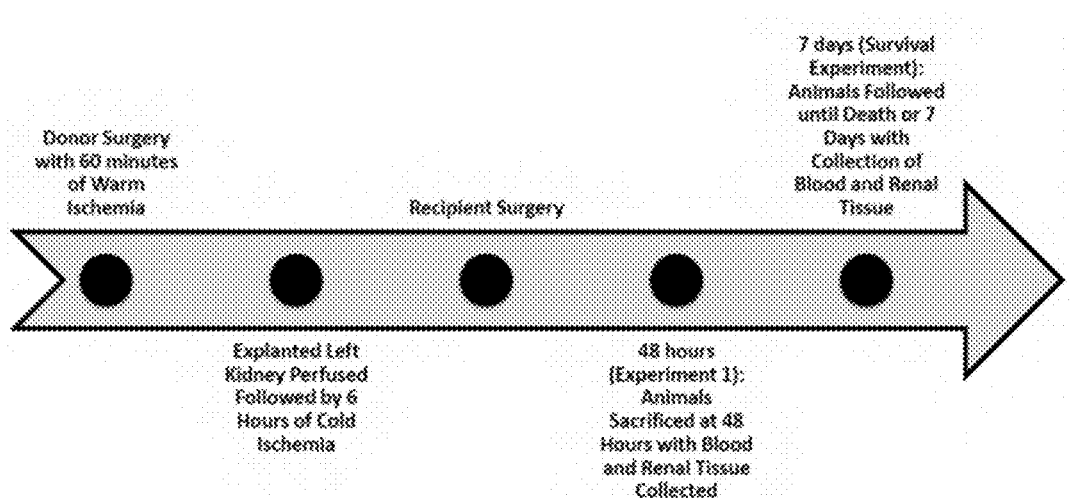
FIG. 30 depicts of timeline of experiments performed in Example 6.

Pharmacokinetics:

Quantitative $^{19}$F spectroscopy was used to estimate the clearance half-life of PPACK-NP in vivo. The half-life of the nanoparticles was determined by measuring the exponential decay of $^{19}$F signal intensity emanating regionally from the tail blood pool (FIG. 27) and fitting the data to a bi-exponential, two compartment model. PPACK-NP exhibited a mean clearance half-life (FIG. 28) of 105.87±23.38 min (N=3), compared to clearance half-lives for plain PFC-NP (181.3±40.7 min, N=3) and PEGylated PFC-NP (240.16±23.42 min, N=3), indicative of only modest effects on pharmacokinetics with selected particle surface modifications. The anticipated clearance mechanism for PFC-NP was the reticuloendothelial system as demonstrated by $^{19}$F-MR imaging of mice post-mortem, which depicted accumulation of nanoparticles in the liver and spleen following 2 hours of nanoparticle circulation prior to sacrifice (FIG. 29).

Discussion of the Results.

The principal new observation in this work is that focal inhibition of plaque thrombin in fat-fed ApoE-null mice results in rapid recovery of damaged endothelial barriers and attenuated vascular procoagulant activity in spite of a continued Western diet. These beneficial outcomes were achieved with the use of anti-thrombin nanoparticles that passively permeated plaque intimal regions after i.v. injection and were focally retained to exert sustained pleiotropic anti-inflammatory effects. Additionally, the progression of atherosclerotic plaque in lesion-prone areas of the ascending aorta was forestalled during the 1 month treatment period. Potential mechanisms for promoting quiescence in activated endothelium related to downregulation of inflammatory NFkB signaling activity through inhibition of the thrombin-PAR1 signaling are illustrated in FIG. 24.

The direct relationship between thrombotic risk and endothelial barrier disruption (FIG. 25 and FIG. 1D in [11]) according to the metrics employed in these models confirms a primary role for intact endothelium in maintaining vascular homeostasis in atherosclerosis. Recent reports of the relationship between endothelial damage/sloughing and acute coronary syndromes in patients[24] recalls original descriptions of hypercoagulable vascular erosions by the Virmani group[25] and focuses attention on ways to measure and preserve endothelial integrity as a strategic path to the detection and reduction of thrombotic risk. Prior work in our lab indicates that the effects of cholesterol feeding elicit both procoagulant effects and barrier disruption only after some time on a sustained high fat diet: >3 months in ApoE-null mice[11] and >6 months in NZW rabbits[10]). In ApoE-null mice, barrier disruption worsens progressively over time on a high fat diet, but can resolve rapidly within 2 months after switching to normal chow.[11] Although leaky vasculature and reduced vasodilatory capacity associated with endothelial dysfunction may occur within weeks of inception of an atherogenic diet in the ApoE-null model[26], the barrier disruption and procoagulant activity identified by our nanoparticle permeability metrics emerge later and may serve as more direct harbingers of thrombotic risk.

Figure 24:
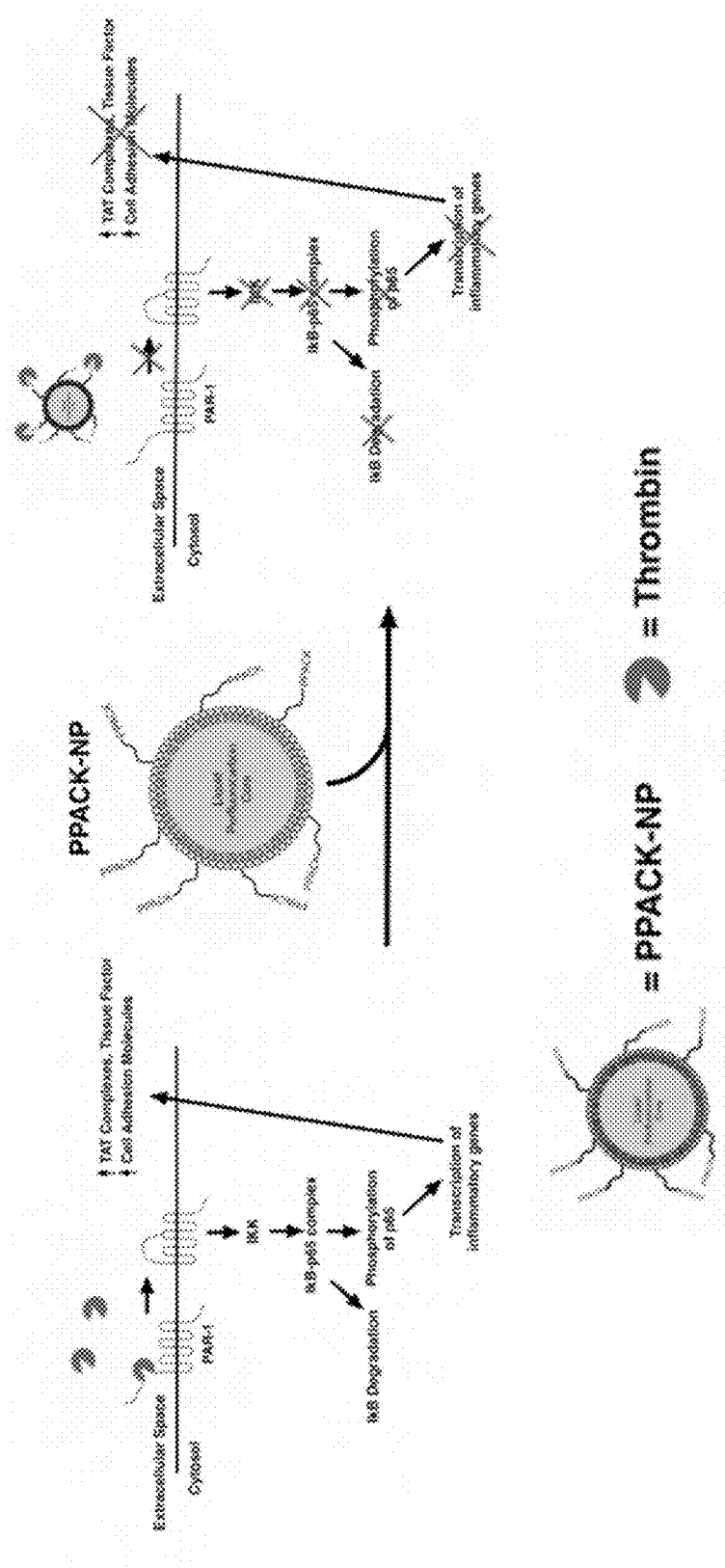
FIG. 24 is a schematic depicting the effect of PPACK-NP on reducing the inflammatory effects of thrombin. Thrombin promotes the release of inflammatory molecules (cell adhesion molecules) and procoagulant molecules (TAT complexes, tissue factor) through the activation of the NF-κB pathway as measured through IκB degradation and phosphorylation of p65.

With respect to the underlying mechanisms responsible for endothelial damage, inflammatory signaling and immunomodulatory events orchestrated by various plaque cell types interacting with activated endothelium have been described in detail.[6] Here we have focused on thrombin as a key instigator of plaque growth and instability contributing to endothelial activation, vessel inflammation, and hypercoagulability, as summarized in FIG. 24. Surprisingly, after an aggressive one-month treatment period with PPACK-NP following 3 months of initial cholesterol feeding, marked benefits were observed even in the face of persistently elevated serum cholesterol. The role of thrombin not only as a principal prothrombotic agent, but also as an atherogenic molecule is not unexpected given that it drives many of the inflammatory molecules that participate in plaque growth such as NFkB[21], NADPH oxidase[27], VCAM-1[28], PDGF[29], among many others.[6] Thrombin's role as a proinflammatory molecule through the activation of the NF-kB pathway results in numerous downstream effects that accelerate plaque development, cell infiltration, expression of inflammatory molecules, and promotion of hypercoagulability through stimulation and secretion of procoagulant enzymes.[30]

Figure 22B:
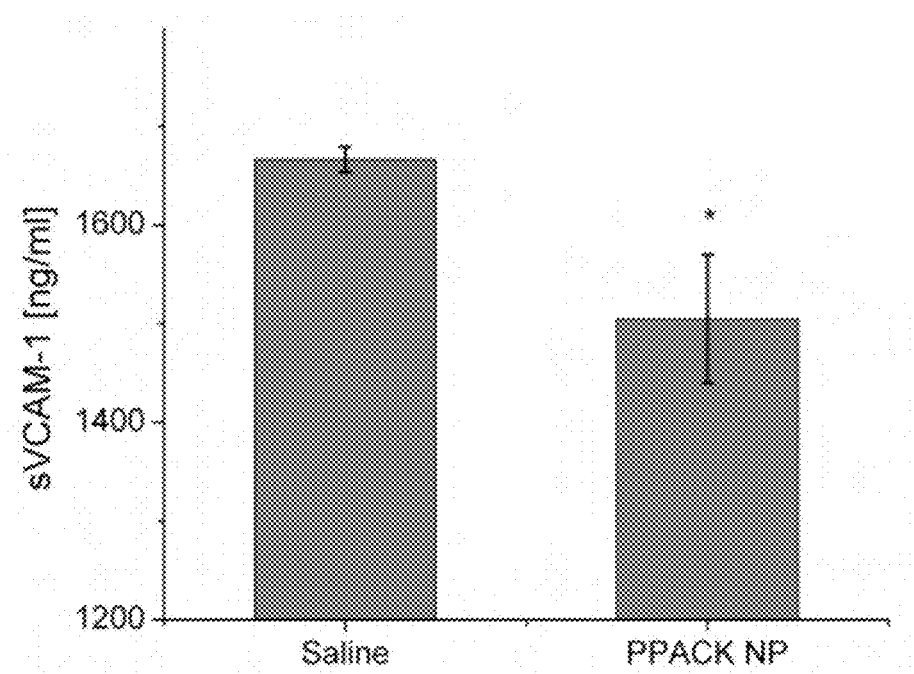

Of particular interest is the role of endothelial-specific NFkB activation in atherogenesis as demonstrated by Gareus et al. with the use of genetically engineered conditional knockouts of endothelial NFkB that markedly suppressed plaque formation in fat-fed ApoE−/− mice.[31] The seminal observations of very early upregulation of NFkB in lesion prone aortic arch regions by Cybulsky's group[32] raises the interesting speculation of a role for thrombin even at these incipient time points, particularly in the context of previously documented clusters of intense, albeit small, clusters of endothelial apoptosis and replication in these aortic arch regions even in normal subjects.[33,34] The ability to achieve focal suppression of NFkB with nanoparticle delivery systems that might abrogate endothelial PAR-1 activation could help to maintain a more quiescent endothelial phenotype (e.g., reduced sVCAM: FIG. 22B), preserve barrier integrity, and simultaneously reduce paracrine crosstalk with other inflammatory plaque components.

A pleiotropic response to the suppression of thrombin signaling in diverse cell types that participate in atherogenesis is evidenced by modulation of NFkB in THP-1 as well as HAEC cells (FIG. 21A-J, and FIG. 26), and our previous reports of reduced platelet content in clots that are produced by vessel injury.[12,13] Regarding platelet activation, synergistic benefits also could accrue by local inhibition of thrombin-PAR-1 signaling through the NFkB axis.[35] However, as a potential caveat, it is interesting to note that selective inhibition of NFkB in macrophage populations has been associated with increased atherosclerosis as contrasted with more specific inhibition of endothelial NFkB.[36] Although we show that NFkB may be downregulated in representative human monocyte cell lines in vitro by interrupting thrombin/PAR-1 activation (FIG. 20A) and in vivo through quantification of pp65 staining in PPACK-NP treated mice, the exact relationships between macrophages and endothelial signaling and responses to this intervention remain to be defined.

Recent experimental reports have explored the role of thrombin and related coagulation enzymes in promoting atherosclerosis with the use of orally administered anti-thrombotic agents or genetically modified mice for primary prevention of atherosclerosis.[37-39] All such studies report significant decreases in overall plaque extent and reduced expression of inflammatory mediators. Secondary prevention clinical trials in patients with acute coronary syndromes using oral anti-thrombotic agents have shown very modest effects on subsequent clinical events related to atherosclerosis progression, but at the risk of significantly increased bleeding.[9] Interestingly, nanoparticle-based thrombin inhibition exhibits similar therapeutic effects to that of the experimental studies mentioned above, but with significantly fewer treatments (12 doses over 4 weeks), no requirement for cholesterol reduction (FIG. 23F), and a more promising safety profile as coagulation parameters and bleeding times have been shown to normalize within 3060 minutes after i.v. injection.[12]

We observed no significant change in plaque macrophage content between treatment groups (FIG. 23A-D) in contrast to the 50% decrease in plaque macrophages reported by Hara et al. after 5 months of Xa inhibition.[40] However, despite our shorter 1-month time window of therapeutic intervention that may not have allowed for reduced plaque macrophage content, our observations of rapid downregulation of NF-kB and downstream inflammatory markers (TF, TAT complexes, sVCAM) (FIG. 21E-H), is consistent with the similar observations of Kadoglou et al in dabigatran-treated ApoE-null mice.[38] These results also accord with previously published date demonstrating the effect of thrombin and PPACK-thrombin in modulating the expression of TF in human saphenous vein endothelial cells, which is thought to be due to activation of NF-kB.

The optimal dosing interval for this therapy and the duration of the local effect on barrier integrity and procoagulant activity remain to be defined. Fortunately, the pharmacokinetics (nanoparticle clearance half life: ~2 hours, FIG. 27) is dominated primarily by the nanoparticle itself, with only modest alterations induced by conjugation of the active pharmacological ingredient (FIG. 28) or other surface constituents. This minor difference in PK may allow for convenient swapping of alternative anticoagulants such as bivalirudin as we have shown previously.[13] These PK parameters are advantageous for potential clinical applications, as we have shown in mice that nanoparticle clearance through the RES (FIG. 29) results in reduction of residual circulating (i.e., nontrapped) bioactive conjugated PPACK or bivalirudin moieties within 30-60 minutes to a level below that required to alter systemic clotting and bleeding parameters.[12,13] The potential disadvantage of intravenous nanotherapy also is notable, but there are a number of clinical scenarios that might benefit from early and aggressive treatment for a period of time before effective cholesterol control could be established. It is also important to note that the particular thrombin inhibitor PPACK may not be entirely specific to thrombin as a serine protease inhibitor, and that local inhibition of other coagulation proteases (e.g. Xa) may in fact exert a synergistic but still locally constrained effect in preventing the activation of thrombin.

1. Libby P P. Inflammation in atherosclerosis. *Arteriosclerosis, Thrombosis, and Vascular Biology* 2012; 32(9): 2045-2051.
2. Borissoff J I J, Spronk H M H H, Cate ten H H. The hemostatic system atherosclerosis. *N. Engl. J. Med.* 2011; 364(18):1746-1760.
3. Kalz J, Cate ten H, Spronk H M H. Thrombin generation and atherosclerosis. *J Thromb Thrombolysis* 2014; 37(1): 45-55.
4. Esmon C T. Crosstalk between inflammation and thrombosis. *Maturitas* 2004; 47(4):305-314.
5. Coughlin S R. How the protease thrombin talks to cells. *Proc. Natl. Acad. Sci. U.S.A.* 1999; 96(20):11023-11027.
6. Borissoff J I, Spronk H M H, Heeneman S, Cate ten H. Is thrombin a key player in the "coagulation-atherogenesis" maze? *Cardiovascular Research* 2009; 82(3):392-403.
7. Olson E S, Whitney M A, Friedman B, Aguilera T A, Crisp J L, Baik F M, Jiang T, Baird S M, Tsimikas S, Tsien R Y, Nguyen Q T. In vivo fluorescence imaging of atherosclerotic plaques with activatable cell-penetrating peptides targeting thrombin activity. *Integr Biol (Camb)* 2012; 4(6):595-605.
8. Borissoff J I, Heeneman S, Kilinç E, Kassák P, van Oerle R, Winckers K, Govers-Riemslag J W P, Hamulyák K, Hackeng T M, Daemen M J A P, Cate ten H, Spronk H M H. Early atherosclerosis exhibits an enhanced procoagulant state. *Circulation* 2010; 122(8):821-830.
9. Costopoulos C, Niespialowska-Steuden M, Kukreja N, Gorog D A. Novel oral anticoagulants in acute coronary syndrome. *Int J Cardiol* 2013; 167(6):2449-2455.
10. Zhang H, Zhang L, Myerson J, Bibee K, Scott M, Allen J, Sicard G, Lanza G, Wickline S. Quantifying the evolution of vascular barrier disruption in advanced atherosclerosis with semipermeant nanoparticle contrast agents. *PLoS ONE* 2011; 6(10):e26385-e26385.
11. Palekar R U, Jallouk A P, Goette M J, Chen J, Myerson J W, Allen J S, Akk A, Yang L, Tu Y, Miller M J, Pham C T N, Wickline S A, Pan H. Quantifying progression and regression of thrombotic risk in experimental atherosclerosis. *FASEB J* 2015; 29(7):3100-3109.
12. Myerson J, He L, Lanza G, Tollefsen D, Wickline S. Thrombin-inhibiting perfluorocarbon nanoparticles provide a novel strategy for the treatment and magnetic resonance imaging of acute thrombosis. *J. Thromb. Haemost.* 2011; 9(7):1292-1300.
13. Myerson J W, He L, Allen J S, Williams T, Lanza G, Tollefsen D, Caruthers S, Wickline S. Thrombin-inhibiting nanoparticles rapidly constitute versatile and detectable anticlotting surfaces. *Nanotechnology* 2014; 25(39): 395101-395101.
14. Morawski A M, Winter P M, Yu X, Fuhrhop R W, Scott M J, Hockett F, Robertson J D, Gaffney P J, Lanza G M, Wickline S A. Quantitative "magnetic resonance immunohistochemistry" with ligand-targeted (19)F nanoparticles. *Magn Reson Med* 2004; 52(6):1255-1262.
15. Chen J, Vemuri C, Palekar R U, Gaut J P, Goette M, Hu L, Cui G, Zhang H, Wickline S A. Antithrombin nanoparticles improve kidney reperfusion and protect kidney function after ischemia-reperfusion injury. *Am. J. Physiol. Renal Physiol.* 2015; 308(7):F765-F773.

16. Tull S P, Bevins A, Kuravi S J, Satchell S C, Al-Ani B, Young S P, Harper L, Williams J M, Rainger G E, Savage C O S. PR3 and elastase alter PAR1 signaling and trigger vWF release via a calcium-independent mechanism from glomerular endothelial cells. *PLoS ONE* 2012; 7(8): e43916.
17. Takeya H, Gabazza E C, Aoki S, Ueno H, Suzuki K. Synergistic effect of sphingosine 1-phosphate on thrombin-induced tissue factor expression in endothelial cells. *Blood* 2003; 102(5):1693-1700.
18. Eitzman D T, Westrick R J, Xu Z, Tyson J, Ginsburg D. Hyperlipidemia promotes thrombosis after injury to atherosclerotic vessels in apolipoprotein E-deficient mice. *Arteriosclerosis, Thrombosis, and Vascular Biology* 2000; 20(7):1831-1834.
19. Westrick R J, Winn M E, Eitzman D T. Murine models of vascular thrombosis. *Arteriosclerosis, Thrombosis, and Vascular Biology* 2007; 27(10):2079-2093.
20. Maganto-Garcia E, Tarrio M, Lichtman A H. Mouse models of atherosclerosis. *Curr Protoc Immunol* 2012; Chapter 15:Unit 15.24.1-23.
21. Rahman A, Fazal F. Blocking NF-KB: an inflammatory issue. *Proceedings of the American Thoracic Society* 2011; 8(6):497.
22. Nylaende M, Kroese A, Stranden E, Morken B, Sandbaek G, Lindahl A K, Arnesen H, Seljeflot I. Prothrombotic activity is associated with the anatomical as well as the functional severity of peripheral arterial occlusive disease. *Thromb. Haemost.* 2006; 95(4):702-707.
23. Blankenberg S, Barbaux S, Tiret L. Adhesion molecules and atherosclerosis. *Atherosclerosis* 2003; 170(2):191-203.
24. Lampka M, Grąbczewska Z, Jendryczka-Maćkiewicz E, Holyńska-Iwan I, Sukiennik A, Kubica J, Halota W, Tyrakowski T. Circulating endothelial cells in coronary artery disease. *Kardiol Pol* 2010; 68(10):1100-1105.
25. Farb A, Burke A P, Tang A L, Liang Y, Mannan P, Smialek J, Virmani R. Coronary Plaque Erosion Without Rupture Into a Lipid Core: A Frequent Cause of Coronary Thrombosis in Sudden Coronary Death. *Circulation* 1996; 93(7):1354-1363.
26. Meyrelles S S, Peotta V A, Pereira T M, Vasquez E C. Endothelial Dysfunction in the Apolipoprotein E-deficient Mouse: insights into the influence of diet, gender and aging. *Lipids Health Dis* 2011; 10(1):211.
27. Jagadeesha D K, Takapoo M, Banfi B, Bhalla R C, Miller F J. Nox1 transactivation of epidermal growth factor receptor promotes N-cadherin shedding and smooth muscle cell migration. *Cardiovascular Research* 2012; 93(3):406-413.
28. Ley K, Huo Y. VCAM-1 is critical in atherosclerosis. *Journal of Clinical Investigation* 2001; 107(10):1209-1210.
29. Bowen-Pope D F, Raines E W. History of discovery: platelet-derived growth factor. *Arteriosclerosis, Thrombosis, and Vascular Biology* 2011; 31(11):2397-2401. doi:10.1161/ATVBAHA.108.179556.
30. Steffel J, Lüscher T F, Tanner F C. Tissue factor in cardiovascular diseases: molecular mechanisms and clinical implications. *Circulation* 2006; 113(5):722-731.
31. Gareus R, Kotsaki E, Xanthoulea S, van der Made I, Gi]bels M J J, Kardakaris R, Polykratis A, Kollias G, de Winther M P J, Pasparakis M. Endothelial Cell-Specific NF-κB Inhibition Protects Mice from Atherosclerosis. *Cell Metabolism* 2008; 8(5):372-383.
32. Ha]ra L, Evans A I, Chen M, Hyduk S J, Collins T, Cybulsky M I. The NF-kappa B signal transduction pathway in aortic endothelial cells is primed for activation in regions predisposed to atherosclerotic lesion formation. *Proc. Natl. Acad. Sci. U.S.A.* 2000; 97(16):9052-9057.
33. Hansson G, Chao S, Schwartz S M, Reidy M A. Aortic endothelial cell death and replication in normal and lipopolysaccharide-treated rats. *The American Journal of Pathology* 1985; 121(1):123-127.
34. Bombeli T, Karsan A, Tait J F, Harlan J M. Apoptotic vascular endothelial cells become procoagulant. *Blood* 1997; 89(7):2429-2442.
35. MALAVER E, ROMANIUK M A, D'ATRI L P, POZNER R G, NEGROTTO S, BENZADÓN R, SCHATTNER M. NF-kappaB inhibitors impair platelet activation responses. *J. Thromb. Haemost.* 2009; 7(8): 1333-1343.
36. Kanters E, Pasparakis M, Gi]bels M J J, Vergouwe M N, Partouns-Hendriks I, Fi]neman R J A, Clausen B E, Förster I, Kockx M M, Ra]ewsky K, Kraal G, Hofker M H, de Winther M P J. Inhibition of NF-kappaB activation in macrophages increases atherosclerosis in LDL receptor-deficient mice. *Journal of Clinical Investigation* 2003; 112(8):1176-1185.
37. Pingel S, Tiyerili V, Mueller J, Werner N, Nickenig G, Mueller C. Thrombin inhibition by dabigatran attenuates atherosclerosis in ApoE deficient mice. *Arch Med Sci* 2014; 10(1):154-160.
38. Kadoglou N P E, Moustardas P, Katsimpoulas M, Kapelouzou A, Kostomitsopoulos N, Schafer K, Kostakis A, Liapis C D. The beneficial effects of a direct thrombin inhibitor, dabigatran etexilate, on the development and stability of atherosclerotic lesions in apolipoprotein E-deficient mice: dabigatran etexilate and atherosclerosis. *Cardiovasc Drugs Ther* 2012; 26(5):367-374.
39. Lee I-O, Kratz M T, Schirmer S H, Baumhäkel M, Böhm M. The effects of direct thrombin inhibition with dabigatran on plaque formation and endothelial function in apolipoprotein E-deficient mice. *Journal of Pharmacology and Experimental Therapeutics* 2012; 343(2):253-257.
40. Hara T, Fukuda D, Tanaka K, Higashikuni Y, Hirata Y, Nishimoto S, Yagi S, Yamada H, Soeki T, Wakatsuki T, Shimabukuro M, Sata M. Rivaroxaban, a novel oral anticoagulant, attenuates atherosclerotic plaque progression and destabilization in ApoE-deficient mice. *Atherosclerosis* March 2015.
41. Bartha K, Brisson C, Archipoff G, la Salle de C, Lanza F, Cazenave J P, Beretz A. Thrombin regulates tissue factor and thrombomodulin mRNA levels and activities in human saphenous vein endothelial cells by distinct mechanisms. *Journal of Biological Chemistry* 1993; 268 (1):421-429.

Example 6

Graft ischemia-reperfusion injury (IRI) continues to hinder acute and long-term organ function following transplantation. Thrombin is known to play a role in ischemia-reperfusion as well as more specifically in renal ischemic injury. Thrombin may adversely affect renal transplant outcomes through activation of the coagulation cascade and cause microvascular thrombosis. Furthermore, thrombin may activate protease-activated receptors, which are present throughout the kidney, resulting in a pro-inflammatory response.[5] Systemic thrombin inhibition has been shown to be effective in improving renal acute and chronic allograft function in animal models.[6] However, systemic thrombin inhibitors have systemic bleeding effects, limiting its adoption in the setting of major surgery such as renal transplantation. There is a clear clinical need for safe preventative therapeutics to enhance organ preservation. The results of this example demonstrate the beneficial effects of PFC-PPACK on both functional and structural measures of renal graft injury as well as improved overall survival. Similar results are expected in other models of organ transplant, and using other direct thrombin inhibitors.

BUN/Creatinine Functional Data.

Figure 31:
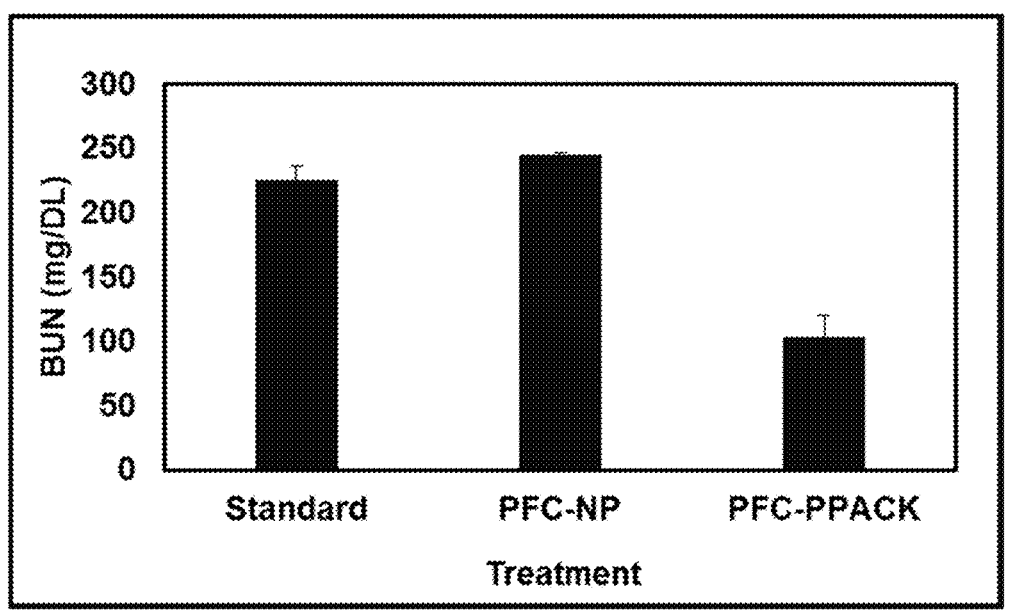
FIG. 31 is a graph depicting significant improvement in renal allograft function (BUN) in treatment (N=5) versus control groups (Standard N=3; PFC-NP N=5). The y-axis represents serum blood urea nitrogen level (BUN) and the x-axis is treatment group. *There was a statistically significant difference between PFC-PPACK and control groups by ANOVA (P<0.01).
Figure 32:
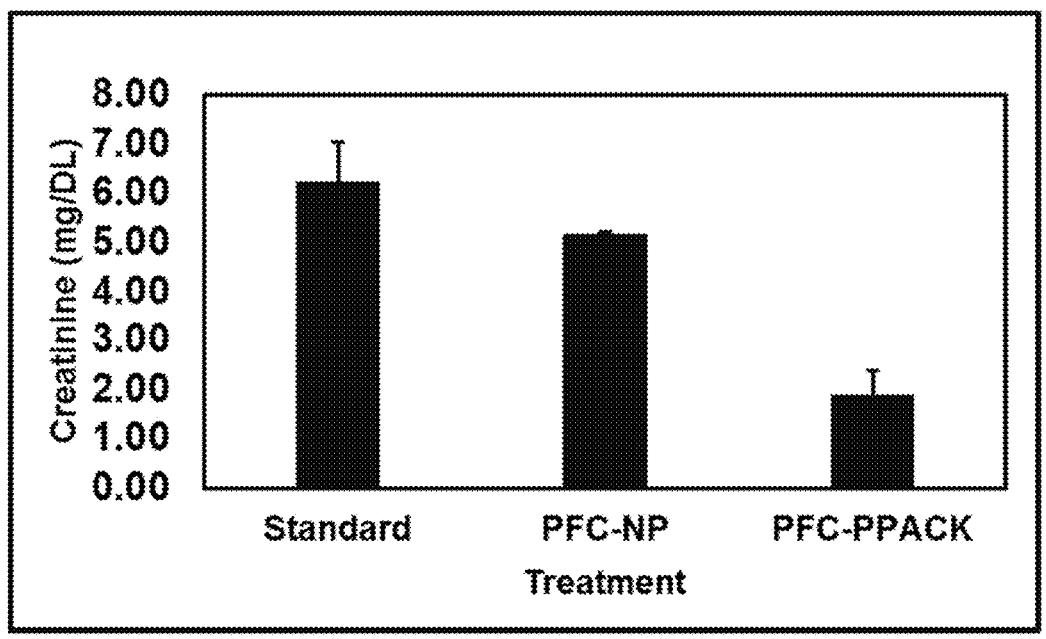
FIG. 32 is a graph depicting significant improvement in renal allograft function (Creatinine) in treatment (N=5) versus control groups (Standard N=3; PFC-NP N=5). The y-axis represents serum Creatinine and the x-axis is treatment group. *There was a statistically significant difference between PFC-PPACK and control groups by ANOVA (P<0.01)

The standard perfusate group exhibited a mean BUN (mg/dL) of 225.33+/−11.62, the PFC-NP a mean of 245.33+/−1.33, and the PFC-PPACK group a mean of 103.00+/−17.04. (FIG. 31) For creatinine (mg/dL), the standard perfusate group exhibited a mean of 6.25+/−0.70, the PFC-NP a mean of 5.16+/−0.06 and the PFC-PPACK group a mean of 1.89+/−0.50. (FIG. 32) By ANOVA analysis, a statistically significant difference was observed between treatment and control groups for both BUN and creatinine (P<0.05).

Renal Parenchymal and Vascular Injury Analysis.

Figure 33:
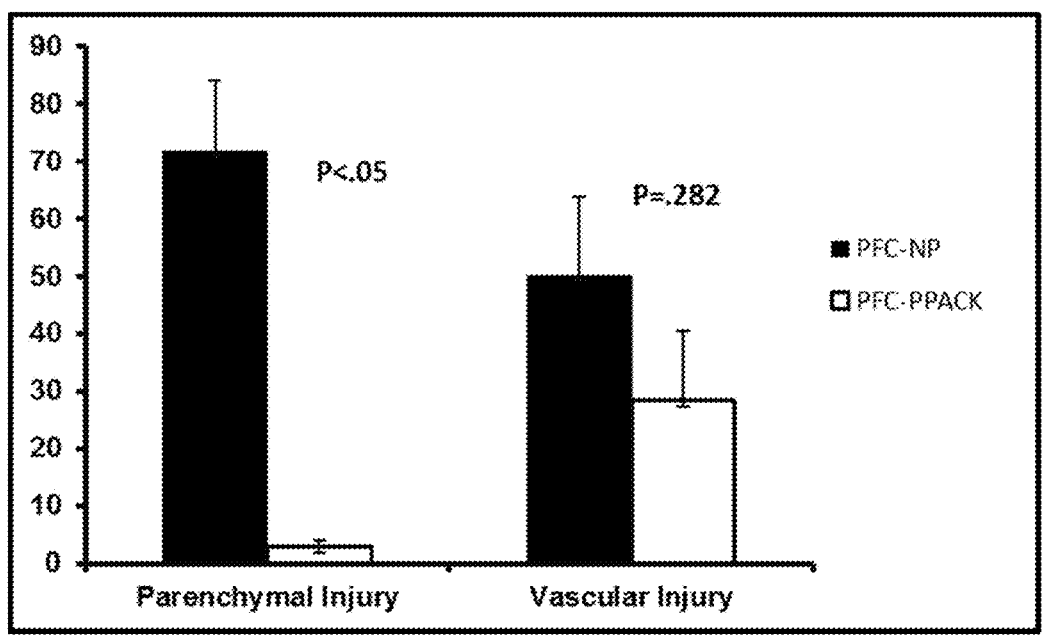
FIG. 33 is a graph depicting significant in parenchymal injury with a trend towards decreased vascular injury in treatment (N=6) versus control groups (N=3 per group). The y-axis represents percent injury and the x-axis is treatment group further grouped by analysis type. There was a statistically significant difference in parenchymal injury (P<0.05) and a matching trend towards a difference in vascular injury (P=0.282).

At 48 hours, the explanted kidney was formalin-fixed, paraffin embedded, sectioned, stained and then analyzed by a blinded, board-certified renal pathologist with expertise in renal pathology. Utilizing a ratio of necrotic to intact tubules as a metric, the degree of parenchymal tubular necrosis in the PFC-NP group was 71.9+/−2.8 versus 12.19+/−1.24 in the PFC-PPACK group (P<0.05; Student's t-test). With application of the same analytic technique, the vascular injury in the PFC-NP was 50.14+/−13.56 versus 28.4+/−12.04 in the PFC-PPACK group (P=0.282; Student's t-test). (FIG. 33)

Survival Data.

Figure 34A:
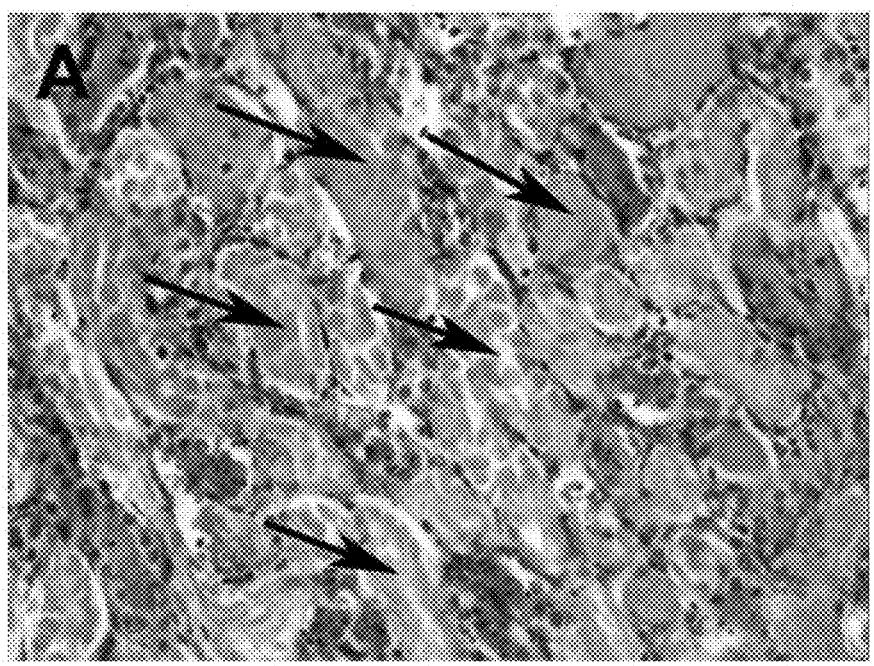
FIG. 34A-B are histology images from the control group demonstrating significant renal parenchymal and vascular injury. (A) is a representative image of a non-treated kidney demonstrating marked coagulative type acute tubular necrosis (arrows) (H&E, 400×). (B) is a representative image of a non-treated kidney with necrosis of the vascular wall (arrows). Acute tubular necrosis is also present (*) (H&E, 100×)
Figure 34B:
Figure 35A:
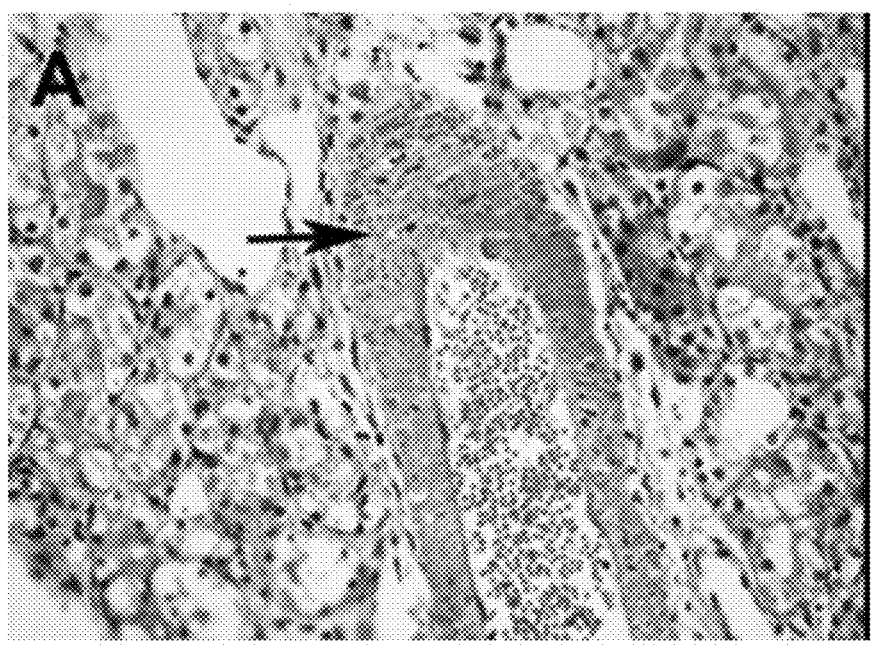
FIG. 35A-F are micrographs that show marked vascular injury in the control group compared to less injury in the treatment group. Representative images demonstrating greater renal vascular injury in the PFC-NP (A-C) group compared to PFC-PPACK (D-F).
Figure 35B:
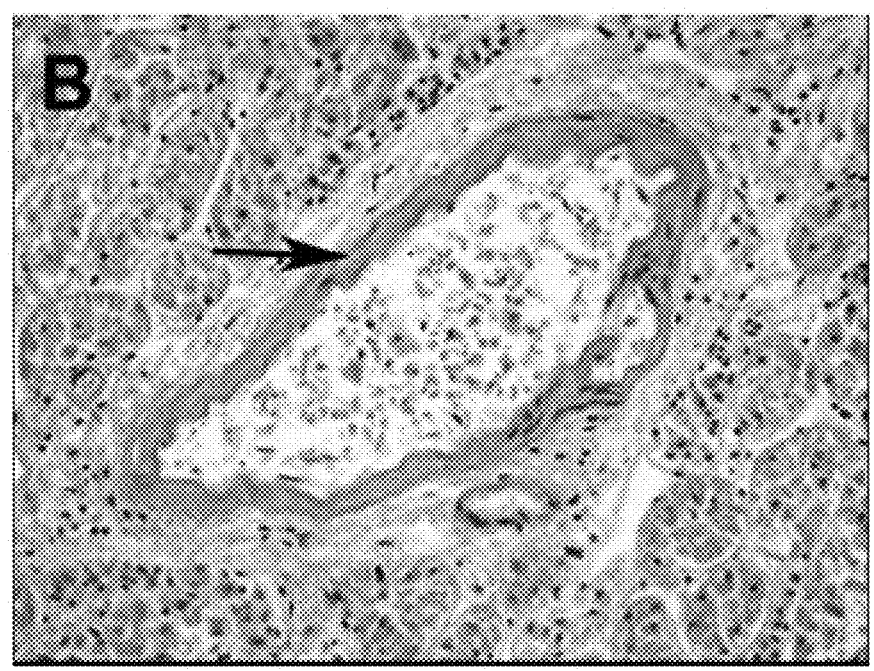
Figure 35C:
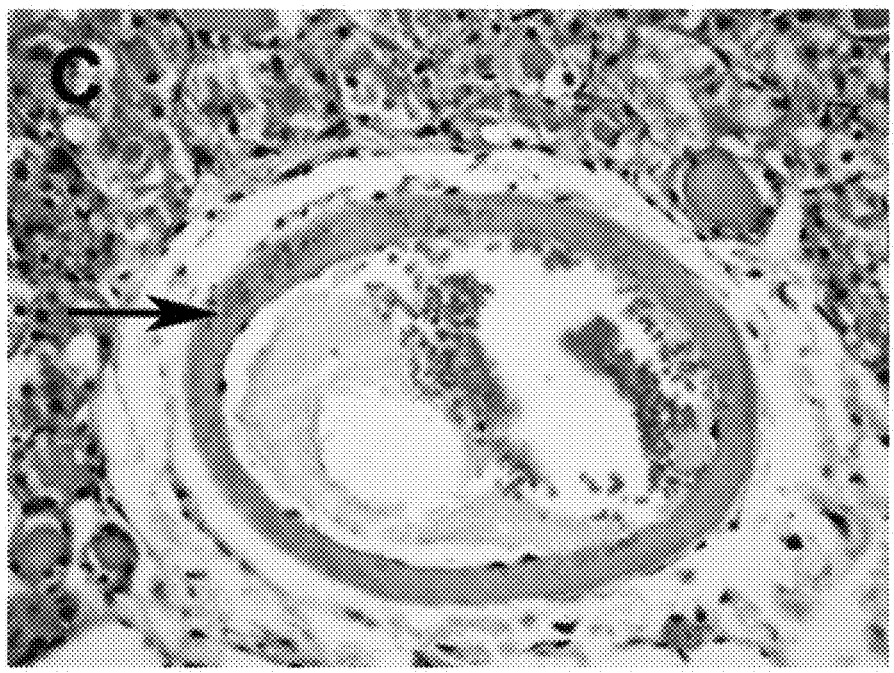
Figure 35D:
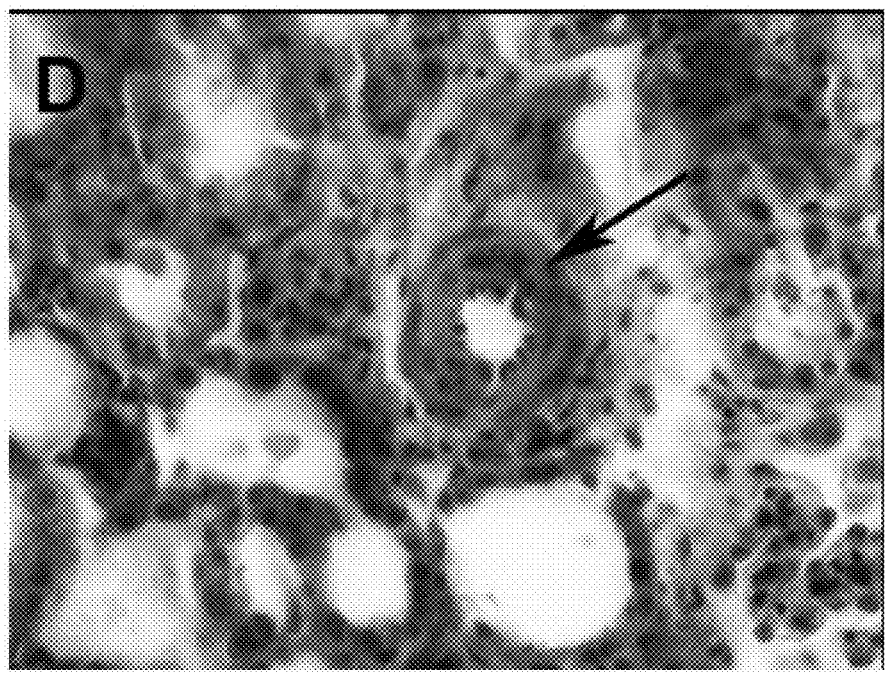
Figure 35E:
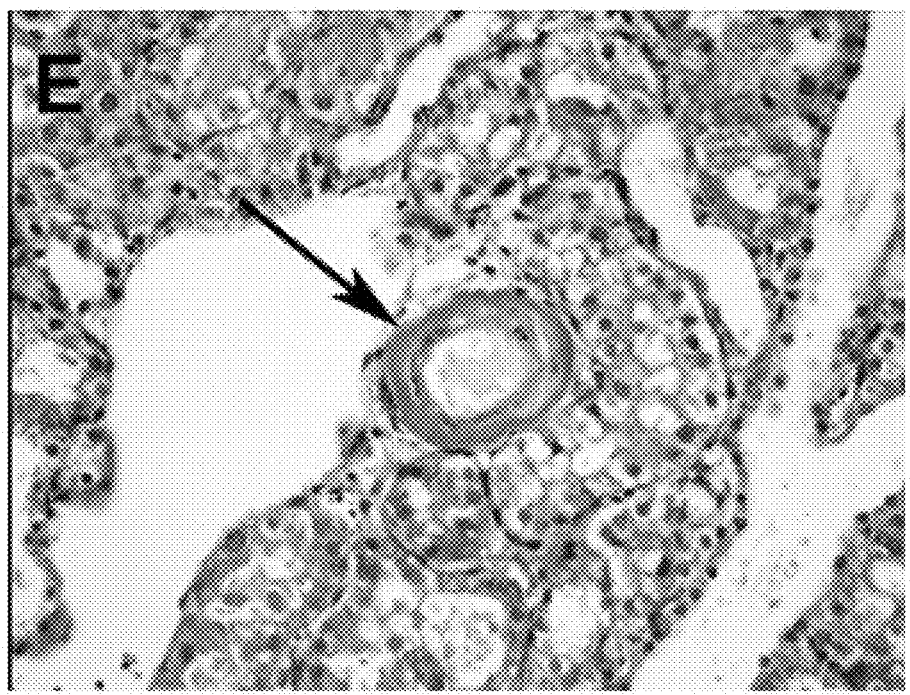
Figure 35F:
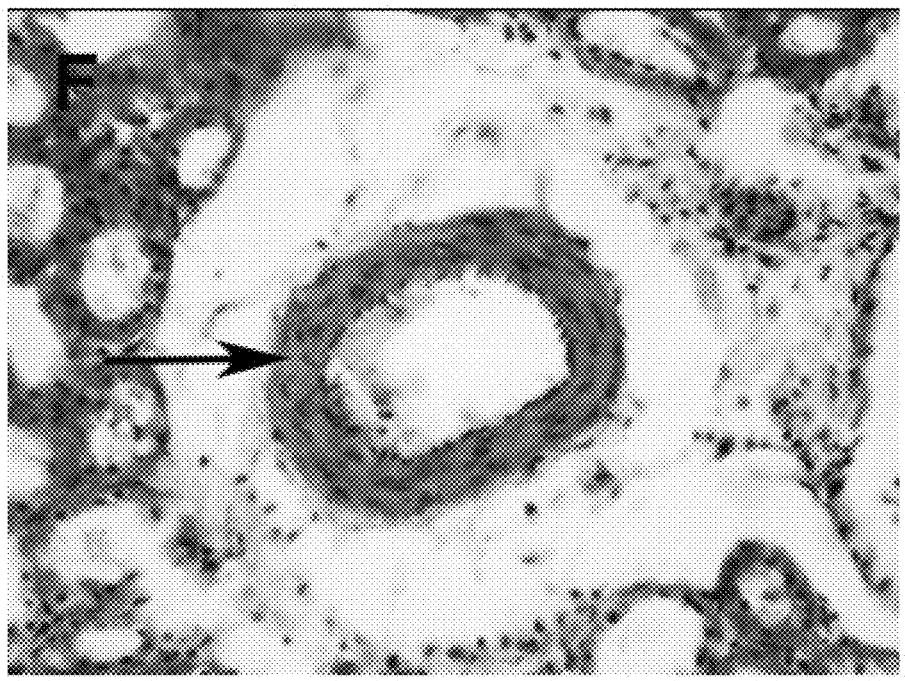
Figure 36:
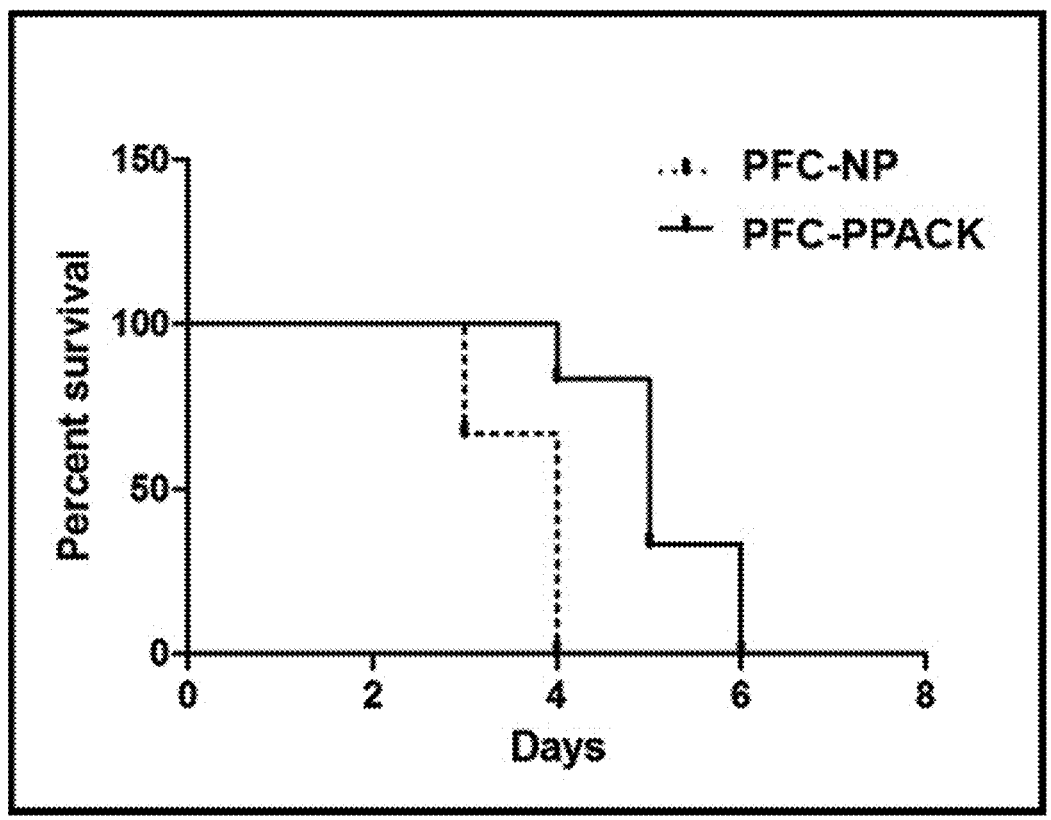
FIG. 36 is a graph showing survival data following DCD renal transplant which revealed a significant improvement in animal survival with PFC-PPACK allograft treatment versus PFC-NP. Male Lewis Rats underwent left renal explantation followed by perfusion of standard PFC-NP (N=4) or PFC-PPACK (N=4). Kidneys then underwent 60 minutes of warm ischemia and 6 hours of cold incubation, followed by transplantation into recipients and native nephrectomy. The y-axis represents percent survival and the x-axis represents days post-transplant. The treatment group had a significantly longer survival than the control group (P<0.05 by log-rank analysis)

To assess survival benefit, the protocol described above was used and the animals were followed until death. The mean survival in the group treated with PFC-PPACK was 6 days versus 4 days for the control PFC-NP group (FIG. 34), statistically significant by log-rank survival analysis (P<0.05). Given the severe nature of the renal injury, all subjects expectedly died from renal failure, although longevity was lengthened in the treated group.

DISCUSSION

The incidence of end-stage renal disease requiring transplant continues to rise with a progressively worsening shortage of organs. Compounding this shortage is the persistent issue of acute and delayed graft function. Furthermore, patients with poor graft function expectedly have worse outcomes in regards to the transplanted organ and overall survival. Improvements in surgical technique and immunosuppression therapies have dramatically improved outcomes, but transplanted organs suffer significant IRI following the pre-transplant period of warm and/or cold ischemia.[1-3] There are no novel therapeutics currently in clinical use to address IRI in renal transplant during renal preservation.

Following transient ischemia, reperfusion results in immediate renal injury due to a combination of microvascular thrombosis and inflammation which then synergistically compound renal injury during the extension phase.[13] Thrombin is known to be involved in IRI both in regards to microvascular thrombosis and through activation of pro-inflammatory pathways via activation of renal protease activated receptors.[5] Other groups have published on improved acute and chronic graft function of renal allografts in pigs systemically treated with the intravenous thrombin inhibitor Megalatran.[6] However, this therapy has not translated into modern patient care as recent data has established the risk of glomerular hemorrhage and tubular obstruction with Dabigtran.[14]

Therefore there is a clear clinical need for targeted therapeutics to address IRI in renal grafts. To this end, the PFC-NP of this example is a safe and effective option. PFC-NPs in this example consist of a liquid perfluorocarbon core encapsulated by an outer phospholipid shell and range 160-300 nm in diameter. These particles can be functionalized through covalent surface modifications through incorporation of molecules into the lipid shell. PPACK is an irreversible inhibitor of thrombin plagued by a short half-life rendering it clinically ineffective. However, PFC-PPACK NP allowed targeted delivery of PPACK to the site of vascular thrombosis while both limiting systemic effects and extending its therapeutic effects. The ability of PFC-PPACK to decrease time to occlusion in a murine model of arterial thrombosis has been published.[9] Furthermore, it has been shown that PFC-PPACK can attenuate renal injury following transient warm ischemia in a murine model of renal ischemia.[15]

Thus, PFC-PPACK is an ideal nanotherapeutic to address the issue of IRI in renal transplantation. It is hypothesized that perfusing explanted organs with PFC-PPACK would improve acute graft function, prevent renal parenchymal and vascular injury and thereby improve animal survival. Although PPACK itself is not necessarily entirely specific for thrombin as compared to other serum proteases, it is clearly useful in this ex vivo application. However, if more selective inhibition of thrombin were desirable, bivalirudin can be substituted easily as a more specific protease inhibitor as shown previously.[9] Moreover, these antithrombin nanoparticles do not affect systemic clotting and bleeding times after 30-60 min when given directly into the circulation in larger doses intravenously, which attests to their excellent safety margin in vivo.[9]

The results of this work demonstrated significant improvement in acute graft function assessed by BUN and creatinine in renal allografts pre-treated with PFC-PPACK compared to controls. Blinded histologic analysis revealed significantly decreased renal tubular necrosis and trended toward reduced vascular injury in the treatment groups compared to control. Additionally, despite the severe injury imposed by this murine DCD renal transplant model, the PFC-PPACK treatment extended survival from 4 to 6 days compared to standard therapy. Importantly, there were no bleeding or inflammatory complications.

What is claimed is:

1. A method of inhibiting thrombin activation of a protein-activated receptor (PAR) in a subject, the method comprising administering to the subject an antithrombotic nanoparticle comprising a core and an outer layer,
    wherein the core of the antithrombotic nanoparticle comprises a perfluorocarbon that is a liquid at about 37° C. and the outer layer comprises a mixture of a lipid and a surfactant;
    wherein the exterior of the antithrombotic nanoparticle comprises a direct thrombin inhibitor covalently conjugated to the exterior via the lipid component of the nanoparticle's outer layer, such that the antithrombotic nanoparticle has a second order kinetic constant for the direct thrombin inhibitor-thrombin interaction that is greater than the same kinetic constant of the direct thrombin inhibitor by itself; and
    wherein the antithrombotic nanoparticle is antithrombotic but does not substantially alter the clotting time of a subject's blood plasma.

2. The method of claim 1, wherein the nanoparticle further comprises an anti-platelet agent.

3. The method of claim 1, wherein the direct thrombin inhibitor is bivalirudin.

4. The method of claim 1, wherein the direct thrombin inhibitor is D-phenylalyl-L-prolyl-L-arginyl-chloromethyl ketone (PPACK).

5. The method of claim 1, wherein the PAR is PAR-1, PAR-3, or PAR-4.

6. The method of claim 1, wherein the PAR is PAR-1.

7. A method of inhibiting thrombin activation of a protein-activated receptor (PAR) in an organ, the method comprising contacting the organ with an antithrombotic nanoparticle comprising a core and an outer layer,
wherein the core of the antithrombotic nanoparticle comprises a perfluorocarbon that is a liquid at about 37° C. and the outer layer comprises a mixture of a lipid and a surfactant;
wherein the exterior of the antithrombotic nanoparticle comprises a direct thrombin inhibitor covalently conjugated to the exterior via the lipid component of the nanoparticle's outer layer, such that the antithrombotic nanoparticle has a second order kinetic constant for the direct thrombin inhibitor-thrombin interaction that is greater than the same kinetic constant of the direct thrombin inhibitor by itself; and
wherein the antithrombotic nanoparticle is antithrombotic but does not substantially alter the clotting time of a subject's blood plasma.

8. The method of claim 7, wherein the nanoparticle further comprises an anti-platelet agent.

9. The method of claim 7, wherein the direct thrombin inhibitor is bivalirudin.

10. The method of claim 7, wherein the direct thrombin inhibitor is D-phenylalyl-L-prolyl-L-arginyl-chloromethyl ketone (PPACK).

11. The method of claim 7, wherein the PAR is PAR-1, PAR-3, or PAR-4.

12. The method of claim 7, wherein the PAR is PAR-1.

* * * * *